US012790299B2

(12) United States Patent
Ford et al.

(10) Patent No.: US 12,790,299 B2
(45) Date of Patent: Nov. 10, 2026

(54) BETA ADRENERGIC AGONIST AND METHODS OF USING THE SAME

(71) Applicant: Curasen Therapeutics, Inc., San Carlos, CA (US)

(72) Inventors: Anthony P. Ford, San Carlos, CA (US); Jiaxin Yu, San Carlos, CA (US); David Scott Carter, San Carlos, CA (US); Wei Chen, San Carlos, CA (US)

(73) Assignee: CuraSen Therapeutics, Inc., San Carlos, CA (US)

( * ) Notice: Subject to any disclaimer, the term of this patent is extended or adjusted under 35 U.S.C. 154(b) by 181 days.

(21) Appl. No.: 17/620,065

(22) PCT Filed: Jun. 30, 2020

(86) PCT No.: PCT/US2020/040308

§ 371 (c)(1),
(2) Date: Dec. 16, 2021

(87) PCT Pub. No.: WO2021/003161

PCT Pub. Date: Jan. 7, 2021

(65) Prior Publication Data

US 2022/0315534 A1 Oct. 6, 2022

Related U.S. Application Data

(63) Continuation-in-part of application No. 16/831,370, filed on Mar. 26, 2020, now Pat. No. 10,947,196, and a continuation-in-part of application No. 16/831,285, filed on Mar. 26, 2020, now Pat. No. 11,040,944.

(60) Provisional application No. 63/018,431, filed on Apr. 30, 2020, provisional application No. 62/934,482,
(Continued)

(51) Int. Cl.

| | |
|---|---|
| ***C07D 213/73*** | (2006.01) |
| ***C07D 209/08*** | (2006.01) |
| ***C07D 209/86*** | (2006.01) |
| ***C07D 213/64*** | (2006.01) |
| ***C07D 215/14*** | (2006.01) |
| ***C07D 215/227*** | (2006.01) |
| ***C07D 223/16*** | (2006.01) |
| ***C07D 231/56*** | (2006.01) |
| ***C07D 235/14*** | (2006.01) |
| ***C07D 237/20*** | (2006.01) |
| ***C07D 241/20*** | (2006.01) |
| ***C07D 261/20*** | (2006.01) |
| ***C07D 263/58*** | (2006.01) |
| ***C07D 265/36*** | (2006.01) |
| ***C07D 277/68*** | (2006.01) |
| ***C07D 309/38*** | (2006.01) |
| ***C07D 471/04*** | (2006.01) |
| ***C07D 491/056*** | (2006.01) |
| ***C07D 498/04*** | (2006.01) |

(52) U.S. Cl.
CPC ......... *C07D 213/73* (2013.01); *C07D 209/08* (2013.01); *C07D 209/86* (2013.01); *C07D 213/64* (2013.01); *C07D 215/14* (2013.01); *C07D 215/227* (2013.01); *C07D 223/16* (2013.01); *C07D 231/56* (2013.01); *C07D 235/14* (2013.01); *C07D 237/20* (2013.01); *C07D 241/20* (2013.01); *C07D 261/20* (2013.01); *C07D 263/58* (2013.01); *C07D 265/36* (2013.01); *C07D 277/68* (2013.01); *C07D 309/38* (2013.01); *C07D 471/04* (2013.01); *C07D 491/056* (2013.01); *C07D 498/04* (2013.01)

(58) Field of Classification Search
CPC .. C07D 213/73; C07D 209/08; C07D 209/86; C07D 213/64; C07D 215/14; C07D 215/227; C07D 223/16; C07D 231/56; C07D 235/14; C07D 237/20; C07D 241/20; C07D 261/20; C07D 263/58; C07D 265/36; C07D 277/68; C07D 309/38; C07D 471/04; C07D 491/056; C07D 498/04; C07D 213/85; C07D 215/48; C07D 215/50; C07D 235/06; C07D 241/42; C07D 249/18; C07D 209/34; C07D 209/88; C07D 209/96; C07D 215/60; C07D 217/16; C07D 221/04; C07D 237/28; C07D 311/18; C07C 215/08
See application file for complete search history.

(56) References Cited

U.S. PATENT DOCUMENTS

| | | | |
|---|---|---|---|
| 3,952,101 | A | 4/1976 | Yu-Wen et al. |
| 3,975,391 | A | 8/1976 | Nakagawa et al. |
| 4,082,847 | A | 4/1978 | Arnett et al. |

(Continued)

FOREIGN PATENT DOCUMENTS

| | | | | |
|---|---|---|---|---|
| CN | 105121418 A | 12/2015 | | |
| DE | 210031 A5 * | 5/1984 | .......... | C07C 215/20 |

(Continued)

OTHER PUBLICATIONS

Chan, H.C.S., "The Principles of Ligand Specificity on beta-2-adrenergic receptor." Scientific Reports 6.1 (2016): 34736.*

(Continued)

*Primary Examiner* — Renee Claytor
*Assistant Examiner* — Christopher Lindsay Johnson
(74) *Attorney, Agent, or Firm* — DLA Piper LLP (US)

(57) ABSTRACT

The present disclosure is directed to chemical compounds and to the use of such compounds in the treatment of diseases associated with an adrenergic receptor.

9 Claims, No Drawings

Related U.S. Application Data filed on Nov. 12, 2019, provisional application No. 62/869,448, filed on Jul. 1, 2019.

(56) References Cited

U.S. PATENT DOCUMENTS

| | | | | | |
|---|---|---|---|---|---|
| 4,460,581 | A | | 7/1984 | Schromm et al. | |
| 4,600,710 | A | | 7/1986 | Liang et al. | |
| 4,800,206 | A | | 1/1989 | Alig et al. | |
| 4,835,175 | A | | 5/1989 | Heindl et al. | |
| 4,853,381 | A | * | 8/1989 | Finch | C07C 45/68 514/218 |
| 4,920,136 | A | * | 4/1990 | Lindel | A61P 15/00 546/310 |
| 4,960,783 | A | | 10/1990 | Bonse et al. | |
| 5,019,578 | A | | 5/1991 | Fisher et al. | |
| 5,264,459 | A | | 11/1993 | Chelmicka-Schorr et al. | |
| 5,462,965 | A | * | 10/1995 | Roba | A61K 31/135 514/254.02 |
| 5,786,356 | A | | 7/1998 | Bell et al. | |
| 5,977,124 | A | | 11/1999 | Dow | |
| 6,277,835 | B1 | | 8/2001 | Brown | |
| 6,291,491 | B1 | | 9/2001 | Weber et al. | |
| 7,528,175 | B2 | | 5/2009 | Bond | |
| 9,539,221 | B2 | | 1/2017 | Bond | |
| 9,730,929 | B2 | | 8/2017 | Eis et al. | |
| 2014/0194430 | A1 | | 7/2014 | Eis et al. | |
| 2015/0011630 | A1 | | 1/2015 | Goldstein et al. | |

FOREIGN PATENT DOCUMENTS

| | | | | | |
|---|---|---|---|---|---|
| EP | 0099766 | A1 | | 2/1984 | |
| EP | 0195397 | A1 | | 9/1986 | |
| EP | 0318092 | A2 | | 5/1989 | |
| EP | 0379928 | A2 | | 8/1990 | |
| EP | 2657227 | A1 | | 10/2013 | |
| GB | 979389 | A | | 1/1965 | |
| GB | 998524 | A | | 7/1965 | |
| GB | 1559915 | A | * | 1/1980 | C07D 235/06 |
| GB | 2305665 | A | | 4/1997 | |
| GB | 2356197 | A | | 5/2001 | |
| JP | S51136684 | A | | 11/1976 | |
| JP | S52283 | A | | 1/1977 | |
| JP | S5350182 | A | | 5/1978 | |
| JP | S53-71074 | A | | 6/1978 | |
| JP | S5742673 | A | | 3/1982 | |
| JP | H01-186867 | A | | 7/1989 | |
| JP | H02235866 | A | | 9/1990 | |
| TW | I877182 | B | | 3/2025 | |
| WO | WO-9318007 | A1 | | 9/1993 | |
| WO | WO 2002/32897 | A1 | | 4/2002 | |
| WO | WO-2004009090 | A1 | | 1/2004 | |
| WO | WO-2004087142 | A1 | | 10/2004 | |
| WO | WO 2007/102771 | A1 | | 9/2007 | |
| WO | WO-2007106016 | A1 | * | 9/2007 | A61K 31/428 |
| WO | WO-2010132015 | A1 | | 11/2010 | |
| WO | WO 2013159064 | A1 | | 10/2013 | |
| WO | WO 2015/042397 | A1 | | 3/2015 | |
| WO | WO 2017012576 | A1 | | 1/2017 | |
| WO | WO 2019/053427 | A1 | | 3/2019 | |

OTHER PUBLICATIONS

Chemical Abstract Service CAS Registry No. 2184735-03-1 (entered into CAS database Mar. 5, 2018), 1 p.*

Petta, V., "Therapeutic effects of the combination of inhaled beta2-agonists and beta-blockers in COPD patients with cardiovascular disease." Heart failure reviews 22 (2017): 753-763.*

17620065 CAS Registry Compound 1502090-96-1 Dec. 24, 2013; 1p.*

Sabbagh, J. J., Kinney, J. W., & Cummings, J. L. (2013). Animal systems in the development of treatments for Alzheimer's disease: challenges, methods, and implications. Neurobiology of aging, 34(1), 169-183. https://doi.org/10.1016/j.neurobiolaging.2012.02.027 (Year: 2013).*

Gutiérrez, I. L., Dello Russo, C., Novellino, F., Caso, J. R., García-Bueno, B., Leza, J. C., & Madrigal, J. L. M. (2022). Noradrenaline in Alzheimer's Disease: A New Potential Therapeutic Target. International journal of molecular sciences, 23(11), 6143. https://doi.org/10.3390/ijms23116143 (Year: 2022).*

Dongdem, J., Etornam, A., Beletaa, S., Alidu, I., Kotey, H., Wezena, C., The β3-Adrenergic Receptor: Structure, Physiopathology of Disease, and Emerging Therapeutic Potential, Advances in Pharmacological and Pharmaceutical Sciences, 2024, 2005589, 32 pages, 2024. https://doi.org/10.1155/2024/2005589 (Year: 2024).*

Kolmus, K., Tavernier, J., & Gerlo, S. (2015). β2-Adrenergic receptors in immunity and inflammation: Stressing NF-κB. Brain, Behavior, and Immunity, 45, 297-310. https://doi.org/10.1016/j.bbi.2014.10.007 (Year: 2015).*

Rowe, R.C., Sheskey, P.J. and Quinn, M.E. (2009) Water. Handbook of Pharmaceutical Excipients. 6th Edition, Pharmaceutical Press, 766-770. (Year: 2009).*

EP Extended Search Report in European Application No. EP20779258, dated Oct. 25, 2022, 10 pages.

PubChem-CID-522893, Create Date: Mar. 27, 2005, p. 2, Figure.

PubChem-CID-82313562, Create Date: Oct. 20, 2014, p. 2, Figure.

PubChem-CID-84671569, Create Date: Oct. 21, 2014, p. 2, Figure.

Alzheimer's Disease Prevention: 7 Tips to Lower Your Risk of Getting Alzheimer's, 2020 (https://www.webmd.com/alzheimers/quide/understandinchalzheimers-diseaseprevention#1).

Down Syndrome Management and Treatment—Cleveland Clinic 2020 (https://my.clevelandclinic.orq/health/diseases/17818-down-syndrome/management-andtreatment).

Down Syndrome Prevention—Cleveland Clinic 2020 (https://my.clevelandclinic.orq/health/diseases/1 781 8-down-syndrome/prevention).

Dryuk et al.' "Synthesis and pesticidal activity of 2-methyl-5-oxiranylpyridine derivatives", Fiziologicheski Aktivaye Veshchestva, 1991, vol. 23, pp. 53-58.

Fragile X Syndrome—Harvard Health 2010 (https://www.health.harvard.edu/a to z/frapile-x-syndrome-a-to-z).

Mayo Clinic Patient Care & Health information Diseases & Conditions Parkinson's Disease 2020 (https://www.mayoclinic.orq/diseases-conditions/parkinsons-disease/symptomscauses/syc-20376055).

PCT International Search Report and Written Opinion in International Application No. PCT/US2020/024948, dated Jul. 24, 2020, 12 pages.

PubChem, Substance Record for SID 33009977, Available Date: Dec. 5, 2007 [retrieved on May 11, 2020]. Retrieved from the Internet: <URL: https://pubchem.ncbi.nlm.nih.gov/substance/33009977>. entire document.

Pubchem, Substance Record for SID 35557804, Available Date: Dec. 5, 2007 [retrieved on Jun. 30, 2020]. Retrieved from the Internet: <URL: https://pubchem.ncbi.nlm.nih.gov/substance/35557804>. entire document.

Chodnekar et al., "Beta-Adrenergic Blocking Agents. 11. Heterocyclic Analogs of Pronethalol [2-Isopropylamino-1-(2-naphthyl)ethanol]", Journal of Medicinal Chemistry, Jan. 1971, 15(1): 49-57.

EP Search Report in European Application No. 20835619.6, dated Jul. 10, 2023, 18 pages.

Meyer et al., "Beta-Adrenergic Blocking Agents. Nitrogen Heteroaryl-Substituted 2-Propanolamines and Ethanolamines", Journal of Medicinal Chemistry, Jan. 1973, 16(10): 1113-1116.

EP Extended Search report in European Application No. 20835619.6, dated Oct. 10, 2023, 21 pages.

Examination Report for Indian Patent Application No. 202217004213, dated May 13, 2024, 7 pages.

Extended European Search Report for Application No. 20878218.5, dated Oct. 17, 2023, 8 Pages.

International Search Report and Written Opinion for International Application No. PCT/US2020/040308, mailed Nov. 19, 2020, 11 Pages.

Office Action and Search Report for Taiwan Patent Application No. 109122042, dated May 2, 2024, 10 pages.

(56) References Cited

OTHER PUBLICATIONS

Office Action for Chinese Patent Application No. 202080054317.7, mailed Jun. 8, 2024, 44 pages.
Office Action for Taiwan Patent Application No. 109110283, dated Apr. 26, 2024, 9 pages.
Schultz O.E., et al., "Synthesis of 1-(4-Quinolyl)-2-(Alkylamino)Ethanols," Archiv der Pharmazie und Berichte der Deutschen Pharmazeutischen Gesellschaft, Dec. 31, 1972, vol. 305, No. 4, pp. 244-248 (with English abstract).
Stanek M., et al., "Hybridization of Beta-adrenergic Agonists and Antagonists Confers G Protein Bias," Journal of Medicinal Chemistry, May 1, 2019, vol. 62, pp. 5111-5131.
STNext, "STNext-RN 1781001-83-9, RN 1514877-40-7, RN 1521969-56-1, RN 1347813-01-7, RN 1897196-64-3, RN 1894916-72-3 et al," STNext REG Database, Jun. 15, 2015, pp. 1-15.
STNext, "STNext-RN 2227683-67-0, RN 1897213-04-5, RN 1784164-20-0, RN 1780138-65-9, RN 1784979-63-0, RN 1554253-33-6, RN 1550887-28-9 et al," STNext REG Database, Mar. 17, 2019, pp. 1-290.
Vaccher M.P., et al., "Benzoxazolinone Phenylethanolamines: Adrenergic Receptor Antagonists Chemical and Pharmacodynamic Study," Farmaco Edizione Scientifica, Dec. 31, 1986, vol. 41, No. 4, pp. 257-269.
CAS Registration No. 2164555-00-2, Registry (STN) [online], Dec. 25, 2017 [Retrieved on Dec. 15, 2023], 1 page.
CAS Registry No. 2025133-26-8; CA Index Name: 3-Pyridinemethanol, 2-bromoalpha-[[(1,1-dimethylethyl)amino]methy1]-; Entered STN: Nov. 4, 2016. Chemical Abstract Services. Source of registration: Chemical Catalog, Supplier: Ukrorgsyntez Ltd.
CAS Registry No. 2279976-24-6; CA Index Name: 3-Pyridinemethanol, alpha-[[(1,1-dimethylethyl)amino]methy1]-2-methyl-; Entered STN: Mar. 6, 2019. Chemical Abstract Services. Source of registration: Chemical Catalog, Supplier: Ukrorgsyntez Ltd.
Kikkawa H., et al., "The Role of the Seventh Transmembrane Region in High Affinity Binding of a Beta2-Selective Agonist Ta-2005," Molecular Pharmacology, 1998, vol. 53, pp. 128-134.
Office Action for Chinese Patent Application No. 202080054317.7, mailed Nov. 23, 2024, 25 pages.
Office Action for Chinese Patent Application No. 2020800543177, mailed Jan. 9, 2024, 30 pages.
Office Action for Chinese Patent Application No. 2020800543177, mailed Jun. 8, 2024, 39 pages.
Office Action for Israel Patent Application No. 285759, mailed Dec. 1, 2024, 7 pages.
Office Action for Israel Patent Application No. 285759, mailed Apr. 17, 2024, 7 pages.
Office Action for Japanese Patent Application No. 2021-557367, mailed Jan. 9, 2024, 11 pages.
Office Action for Japanese Patent Application No. 2022500006, mailed Jul. 8, 2024, 15 pages.
Peterson L., et al., "Potential Benefits of Therapeutic Use of Beta2Adrenergic Receptor Agonists in Neuroprotection and Parkinson's Disease," Journal of Immunology Research, 2014, vol. 2014, 8 pages.
PubChem: "(1R)-2-(Methylamino)-1-Pyrazin-2-Ylethanol," Compound Summary, CID 10285809; IUPAC Name: National Center for Biotechnology Information, Create date: Oct. 25, 2006, 9 pages, Retrieved from URL: https://pubchem.ncbi.nlm.nih.gov/compound/10285809.
Registry (STN) [online], Apr. 19, 1998, 13 pages, [Date of retrieval Jun. 11, 2024], CAS Registry Nos. 204321-34-6, 1535384-03-2, 1501328-76-2, and 779985-59-0.
STNext, STNext, STNext RN 1535384-03-2, RN 1523264-53-0, RN 1501328-76-2, RN 779985-59-0, RN 690202-87-0, RN 204321-34-6, etc., STNext Reg Database, Feb. 2014, 33 pages.
Vaccher M.P., et al., "Phenylethanolamines Benzoxazolinoniques Antagonistes Ded Recepteurs Adrenergiques. Etude Chimique Et Pharmacodynamique," IL Farmaco Edizione Scientifica, 1986, vol. 41, No. 4, pp. 257-269.
Yoshizaki S., et al., "Sympathomimetic Amines Having a 3,4-Dihydrocarbostyril Nucleus," Chemical and Pharmaceutical Bulletin, 1978, vol. 26, No. 5, pp. 1611-1614.
Database Registry [Online], CAS Registry No. 2293894-53-6 (Publication Date: Mar. 26, 2019).
Database Registry [Online], CAS Registry No. 2293781-15-2 (Publication Date: Mar. 26, 2019.).
Database Registry [Online], CAS Registry No. 2107182-82-9 (Publication Date: Aug. 2, 2017).
Database Registry [Online], CAS Registry No. 1784309-13-2 (Publication Date: Jun. 19, 2015).
Database Registry [Online], CAS Registry No. 2293587-35-4 (Publication Date: Mar. 26, 2019).
Database Registry [Online], CAS Registry No. 2280063-43-4 (Publication Date: Mar. 7, 2019).
Notice of Preliminary Rejection for Korean Patent Application No. 10-2021-7030777 issued Apr. 7, 2025, 30 pages.
Notice of Reasons for Rejection for Japanese Patent Application No. 2022-500006 issued Feb. 3, 2025, 8 pages.
Registry (STN)[online], [date of retrieval Jan. 29, 2025], Jul. 5, 2019, CAS Registry Nos. 2351547-34-5, 2111714-32-8, 2107540-34-9, 2103961-68-6, and 2103960-90-1.
Registry (STN)[online], [date of retrieval Jan. 29, 2025], Jun. 27, 2018, CAS Registry Nos. 2227677-60-1, 1897213-04-5, 1891850-72-8, 1891831-77-8, 1784209-85-3, 1784209-34-2, 1784188-18-6, 1784164-20-0, 1783978-94-8, and 1782863-10-8.
Office Action for TW109122042, mailed Nov. 5, 2025, 12 pages.
CAS RN 1784209-34-2; Name: 3-Bromo-alpha-[(methylamino)methyl]-1H-indazole-4-methanol. Entered STN: Jun. 19, 2015. Chemical catalog supplier: Aurora Fine Chemicals.
CAS RN 1784188-18-6; Name: 3-Chloro-alpha-[(methylamino)methyl]-1H-indazole-4-methanol. Entered STN: Jun. 19, 2015. Chemical catalog supplier: Aurora Fine Chemicals.
CAS RN 690202-87-0; IUPAC 8-[2-[(1,1-Dimethylethyl)amino]-1-hydroxyethyl]-2H-1,4-benzoxazin-3(4H)-one. Entered STN: Jun. 6, 2004 Source: CA.
Sharma, Monika, and Patrick M. Flood. "Adrenergic receptors as pharmacological targets for neuroinflammation and neurodegeneration in Parkinson's disease." Neuroprotection. IntechOpen, 2018. Published: Nov. 26, 2018 DOI: 10.5772/intechopen.81343, 23 pages.
CAS REG No. 2228123-82-6, Date entered STN: Jun. 28, 2018, α-Amino-β-hydroxy-1-methyl-1H-indole-4-propanoic acid.
CAS REG No. 2228112-52-3, Date entered STN: Jun. 28, 2018, α-Amino-β-hydroxy-1-methyl-1H-indole-7-propanoic acid.
CAS REG No. 2168870-55-9, Date entered STN: Jan. 3, 2018 α-(1-Aminobutyl)-1H-indole-4-methanol [2].
CAS REG No. 2168264-10-4, Date entered STN: Jan. 2, 2018, 2-Amino-1-(1H-indol-6-yl)-1,3-propanediol.
CAS REG No. 2110956-62-0, Date entered STN: Aug. 9, 2017, 1H-Indole-5-methanol, α-(1-aminoethyl)-3-bromo.
CAS REG No. 2110707-92-9, Date entered STN: Aug. 9, 2017, α-(1-Aminopropyl)-1,7-dimethyl-1H-indole-6-methanol.
CAS REG No. 2111006-81-4, Date entered STN: Aug. 9, 2017, α-(1-Aminobutyl)-5-fluoro-1H-indole-6-methanol.
CAS REG No. 2111008-28-5, Date entered STN: Aug. 9, 2017, 1H-Indole-6-methanol, α-(1-aminopropyl)-7-methoxy-1-methyl.
Examination Report for AU2020300999 mailed Nov. 5, 2025, 9 pages.
Examination Report for IL289350 mailed Sep. 10, 2025, 9 pages.
Examination Report for Indian Application No. 202117048970 mailed Jun. 9, 2026, 8 pages.

* cited by examiner

BETA ADRENERGIC AGONIST AND METHODS OF USING THE SAME

CROSS-REFERENCE TO RELATED APPLICATIONS

This application is a 35 USC § 371 National Stage application of International Application No. PCT/US2020/040308 filed Jun. 30, 2020, now pending; which is a continuation-in-part application of U.S. application Ser. No. 16/831,370 filed Mar. 26, 2020, now issued as U.S. patent Ser. No. 10/947,196; and to U.S. application Ser. No. 16/831,285 filed Mar. 26, 2020, now issued as U.S. patent Ser. No. 11/040,944. International Application No. PCT/US2020/040308 filed Jun. 30, 2020, now pending, also claims the benefit under 35 USC § 119(e) to U.S. Application Ser. No. 63/018,431 filed Apr. 30, 2020, U.S. Application Ser. No. 62/934,482 filed Nov. 12, 2019 and to U.S. Application Ser. No. 62/869,448 filed Jul. 1, 2019, all now expired. The disclosure of each of the prior applications is considered part of and is incorporated by reference in the disclosure of this application.

FIELD

The present disclosure relates generally to chemical compounds and, in some embodiments, to beta adrenergic agonists and uses in the treatment of diseases associated with an adrenergic receptor.

BACKGROUND

PCT Application Publication Number WO2017197324 discloses "[a]drenergic receptor modulating compounds and methods of treating a subject for a disease or condition associated with an adrenergic receptor including administering a therapeutically effective amount of the subject compound."

United States Patent Application Publication Number 20130096126 discloses "a method for enhancing learning or memory of both in a mammal having impaired learning or memory or both from a neuro-degenerative disorder, which entails the step of administering at least one compound or a salt thereof which is a β1-adrenergic receptor agonist, partial agonist or receptor ligand in an amount effective to improve the learning or memory or both of said mammal."

United States Patent Application Publication Number 20140235726 discloses "a method of improving cognition in a patient with Down syndrome, which entails administering one or more β2 adrenergic receptor agonists to the patient in an amount and with a frequency effective to improve cognition of the patient as measured by contextual learning tests."

United States Patent Application Publication Number 20160184241 discloses "a method of improving cognition in a patient with Down syndrome, which entails intranasally administering one or more β2-ADR agonists or pharmaceutically-acceptable salts of either or both to the patient in an amount and with a frequency effective to improve cognition of the patient as measured contextual learning tests."

SUMMARY

The present disclosure is based at least in part on the identification of compounds that modulate adrenergic receptor and methods of using the same to treat diseases associated with an adrenergic receptor. Disclosed herein is a compound according to Formula (I) or an optically pure stereoisomer, pharmaceutically acceptable salt, solvate, or prodrug thereof Formula (I)

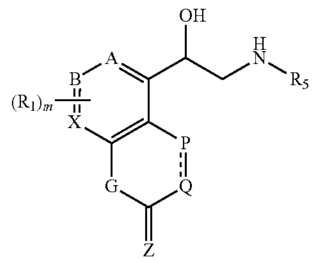

In some embodiments of Formula (I), each $R_1$ is independently selected from the group consisting of hydrogen, halogen, cyano, nitro, unsubstituted or substituted amino, pentafluorosulfanyl, unsubstituted or substituted sulfonyl, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl.

In some embodiments of Formula (I), m is an integer selected from 0 to 3.

In some embodiments of Formula (I), each A, B, and X is independently a nitrogen or carbon.

In some embodiments of Formula (I), P is N, O, or $CR_2$; Q is N, O, or $CR_2$; G is $NR_5$ or O; and/or Z is $NR_5$, O, S, or $CR_3R_4$. In some embodiments, $R_2$ is selected from the group consisting of hydrogen, halogen, cyano, nitro, hydroxyl, unsubstituted or substituted amino, unsubstituted or substituted alkyl, and unsubstituted or substituted alkoxy. In certain embodiments, each $R_3$ and $R_4$ is selected from the group consisting of hydrogen, halogen, cyano, nitro, hydroxyl, unsubstituted or substituted amino, unsubstituted or substituted alkyl, and unsubstituted or substituted alkoxy.

In some embodiments of Formula (I), $R_5$ is one or more selected from the group consisting of H, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

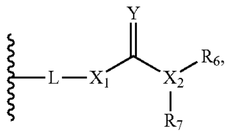

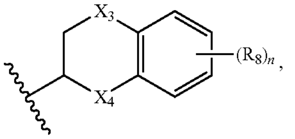

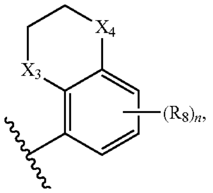

-continued

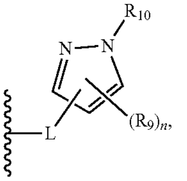

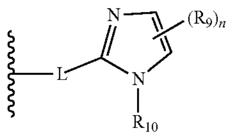

,

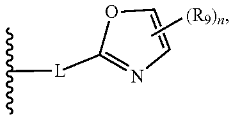

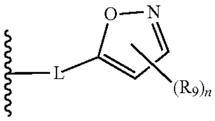

,

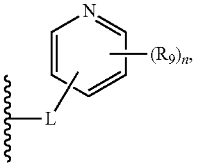

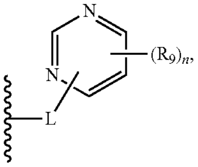

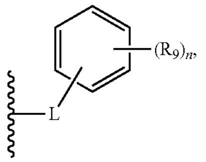

and

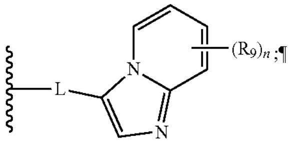

L is a C1-C5 alkyl linker optionally substituted; each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl; Y is O or S; $R_6$ and $R_7$ are independently selected from hydrogen, unsubstituted or substituted alkyl, or $R_6$ and $R_7$ are cyclically linked and together with $X_2$ to form an optionally substituted cycloalkyl or heterocycle; each $R_8$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl; n is an integer selected from 0 to 4; $R_9$ is selected from the group consisting of hydrogen, halogen, cyano, unsubstituted or substituted alkyl, unsubstituted or substituted alkoxy, and unsubstituted or substituted amino; and $R_{10}$ is selected from the group consisting of hydrogen, cyano, unsubstituted or substituted alkyl, and unsubstituted or substituted alkoxy.

Also disclosed herein is a compound according to Formula (II) or an optically pure stereoisomer, pharmaceutically acceptable salt, solvate, or prodrug thereof Formula (II)

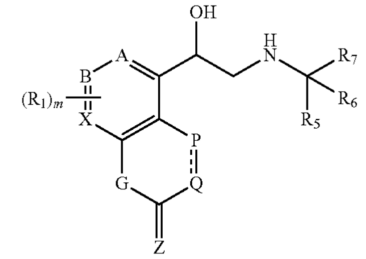

In some embodiments of Formula (II), each $R_1$ is independently selected from the group consisting of hydrogen, halogen, cyano, nitro, unsubstituted or substituted amino, pentafluorosulfanyl, unsubstituted or substituted sulfonyl, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl.

In some embodiments of Formula (II), m is an integer selected from 0 to 3.

In some embodiments of Formula (II), each A, B, and X is independently a nitrogen or carbon.

In some embodiments of Formula (II), P is N, O, or $CR_2$; Q is N, O, or $CR_2$; G is $NR_5$ or O; and/or Z is $NR_5$, O, S, or $CR_3R_4$.

In some embodiments of Formula (II), $R_2$ is selected from the group consisting of hydrogen, halogen, cyano, nitro, hydroxyl, unsubstituted or substituted amino, unsubstituted or substituted alkyl, and unsubstituted or substituted alkoxy.

In some embodiments of Formula (II), each $R_3$ and $R_4$ is selected from the group consisting of hydrogen, halogen, cyano, nitro, hydroxyl, unsubstituted or substituted amino, unsubstituted or substituted alkyl, and unsubstituted or substituted alkoxy.

In some embodiments of Formula (II), $R_5$, $R_6$, and $R_7$ are independently selected from the group consisting of H, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

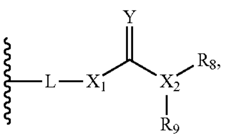

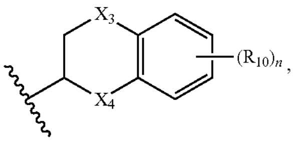

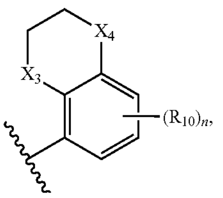

-continued

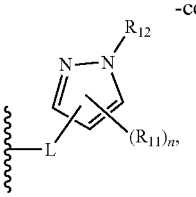
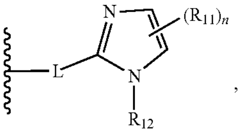
,
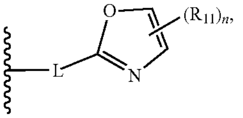
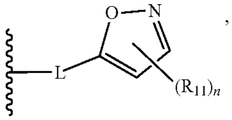
,
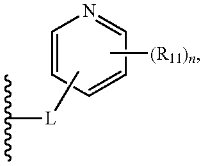
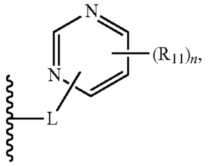
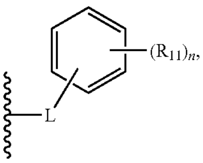
and
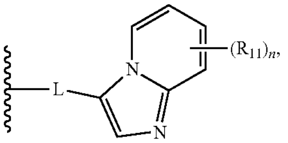

or $R_5$ and $R_6$ together with the carbon form an unsubstituted or substituted 3-7 membered cycloalkyl or heterocycle ring; L is a C1-C5 alkyl linker optionally substituted; each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl; Y is O or S; $R_8$ and $R_9$ are independently selected from hydrogen, unsubstituted or substituted alkyl, or $R_8$ and $R_9$ are cyclically linked and together with $X_2$ to form an optionally substituted cycloalkyl or heterocycle; each $R_{10}$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl; n is an integer selected from 0 to 4; $R_{11}$ is selected from the group consisting of hydrogen, halogen, cyano, unsubstituted or substituted alkyl, unsubstituted or substituted alkoxy, and unsubstituted or substituted amino; and $R_{12}$ is selected from the group consisting of hydrogen, cyano, unsubstituted or substituted alkyl, and unsubstituted or substituted alkoxy.

Also disclosed herein is a compound according to Formula (I'):

Formula (I')

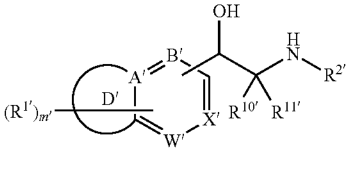

or a pharmaceutically acceptable salt, wherein:

A', B', W', and X' are each independently a nitrogen atom or carbon atom;

Ring D' is a fused ring selected from benzo, 5-9 membered monocyclic or bicyclic heteroaryl containing 1-4 heteroatoms independently selected from nitrogen, oxygen, or sulfur, and a 5 to 7-membered saturated or partially unsaturated carbocyclyl or heterocyclyl having 1-3 heteroatoms independently selected from nitrogen, oxygen, or sulfur;

each $R^{1'}$ is independently hydrogen, halogen, $R^A$, —CN, —$NO_2$, —$SF_5$, —O—, —OR', —NR'$_2$, —$SO_2$R', —C(O)R', —C(O)NR'$_2$, —NR'C(O)R', —NR'$CO_2$R', or —$CO_2$R';

each $R^A$ is independently an optionally substituted group selected from C1-6 aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two $R^A$ groups on the same carbon or are optionally taken together with their intervening atoms to form an optionally substituted 3-6 membered saturated or partially unsaturated carbocyclic or heterocyclic ring having 1-3 heteroatoms, in addition to the carbon from which the two $R^A$ groups are attached, independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{2'}$ is selected from hydrogen, $R^A$, —OR',

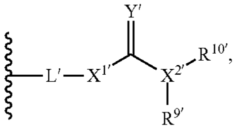
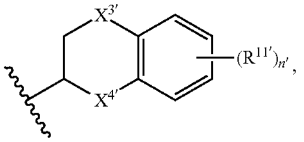
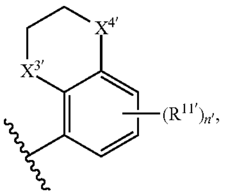
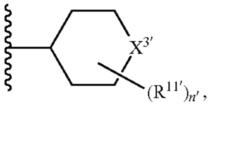

-continued

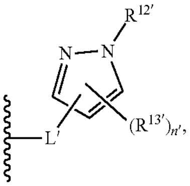 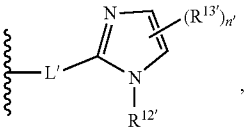,

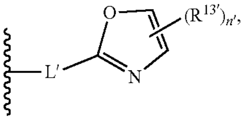 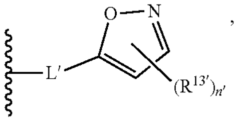,

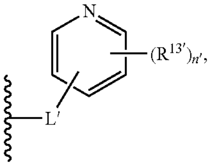 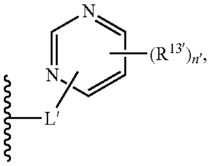

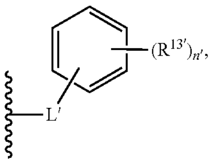 and

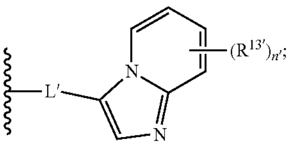

L' is an optionally substituted $C_{1-5}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^2$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12'}$ is hydrogen, $R^A$, or —CN;

each $R^{13'}$ is independently hydrogen, halogen, $R^A$, —CN, —OR', or —$NR'_2$; and $R^{7'}$ and $R^{8'}$ are each independently hydrogen or optionally substituted $C_{1-2}$ aliphatic.

As described herein, a structure depicted as

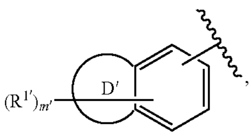, includes for example, structures

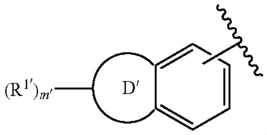, 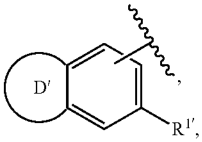, and

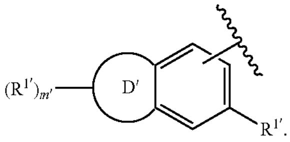.

Also disclosed herein is a compound according to Formula (II'):

Formula (II')

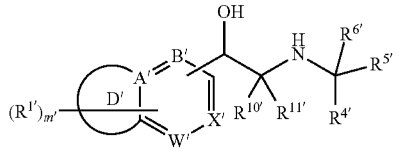

or a pharmaceutically acceptable salt, wherein:

A', B', W', and X' are each independently a nitrogen atom or carbon atom;

Ring D' is a fused ring selected from benzo, 5-9 membered monocyclic or bicyclic heteroaryl containing 1-4 heteroatoms independently selected from nitrogen, oxygen, or sulfur, and a 5 to 7-membered saturated or partially unsaturated carbocyclyl or heterocyclyl having 1-3 heteroatoms independently selected from nitrogen, oxygen, or sulfur;

each $R^{1'}$ is independently hydrogen, halogen, $R^A$, —CN, —$NO_2$, —$SF_5$, —O—, —OR', —$NR'_2$, —$SO_2R'$, —C(O)R', —C(O)$NR'_2$, —NR'C(O)R', —$NR'CO_2R'$, or —$CO_2R'$;

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two $R^A$ groups on the same carbon or are optionally taken together with their intervening atoms to form an optionally substituted 3-6 membered saturated or partially unsaturated carbocyclic or heterocyclic ring having 1-3 heteroatoms, in addition to the carbon from which the two $R^A$ groups are attached, independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{4'}$, $R^{5'}$, and $R^{6'}$ are each independently selected from hydrogen, halogen, $R^A$, —CN, —$NO_2$, —OR', —$NR'_2$,

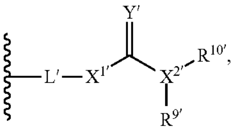

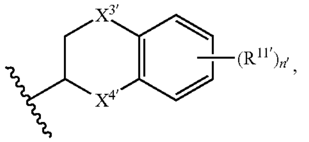

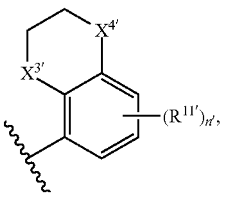

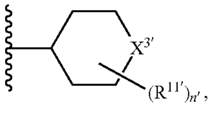

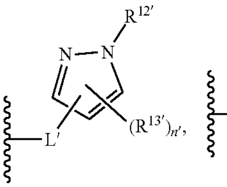

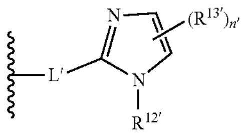

,

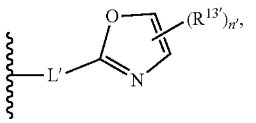

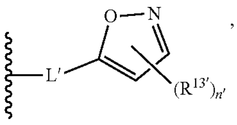

,

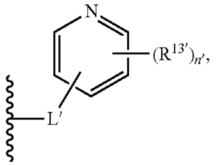

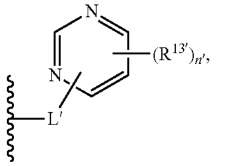

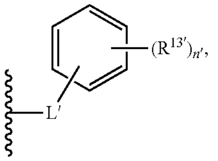

and

-continued

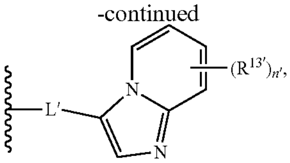

or:

$R^{4'}$ and $R^{5'}$ are optionally taken together with the carbon to which they are attached to form an optionally substituted ring selected from 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is an optionally substituted $C_{1-5}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^2$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12'}$ is hydrogen, $R^A$, or —CN;

each $R^{13'}$ is independently hydrogen, halogen, $R^A$, —CN, —OR', or —$NR'_2$; and $R^{7'}$ and $R^{8'}$ are each independently hydrogen or optionally substituted $C_{1-2}$ aliphatic.

Also disclosed herein is a compound according to Formula (III'):

Formula (III')

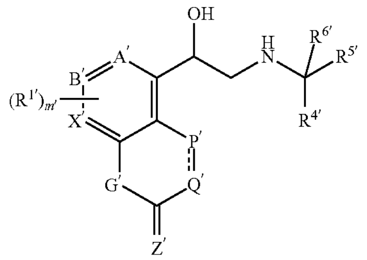

or a pharmaceutically acceptable salt thereof, wherein:

A', B', and X' are each independently a nitrogen atom or carbon atom;

P' and Q' are each independently —N═, —NR'—, —CR'═, or —$CR'_2$—;

G' is —NR'— or —O—;

Z' is ═NR', ═O, ═S, or ═$CR'_2$;

═ ═ is a single bond or double bond;

each $R^{1'}$ is independently hydrogen, halogen, $R^A$, —CN, —$NO_2$, —$SF_5$, —OR', —$NR'_2$, —$SO_2R'$, —C(O)R', —C(O)$NR'_2$, —NR'C(O)R', —NR'$CO_2$R', or —$CO_2$R';

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R groups are attached, independently selected from nitrogen, oxygen, and sulfur;

m is an integer selected from 0 to 3;

$R^{4'}$, $R^{5'}$, and $R^{6'}$ are each independently selected from hydrogen, halogen, $R^A$, —CN, —$NO_2$, —OR', —$NR'_2$,

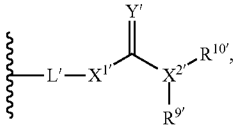

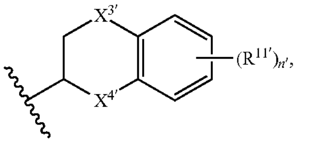

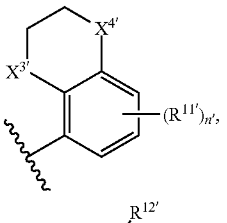

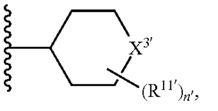

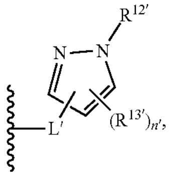

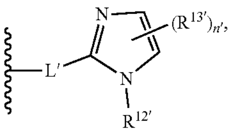

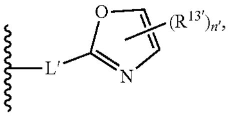

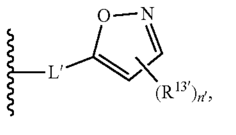

-continued

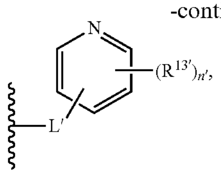

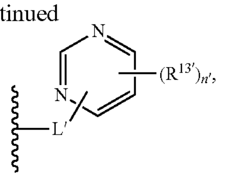

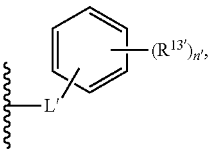

and

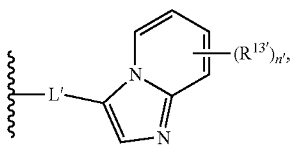

or:

$R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or a partially unsaturated monocyclic heterocyclic ring having 1-2 heteroatoms independently selected from nitrogen, oxygen, and sulfur;

L' is an optionally substituted $C_{1-5}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12'}$ is hydrogen, $R^A$, or —CN; and each $R^{13'}$ is independently hydrogen, halogen, $R^A$, —CN, —OR', or —$NR'_2$.

Further disclosed herein is a compound with the following structure:

Compound 04-1

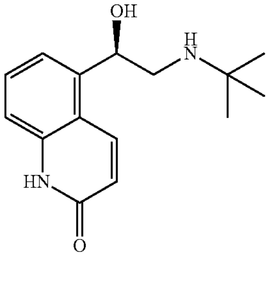

or an optically pure stereoisomer, pharmaceutically acceptable salt, solvate, or prodrug thereof.

Further disclosed herein is a compound with the following structure:

Compound 04-2

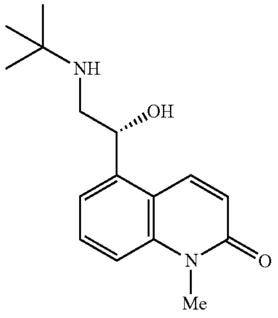

or an optically pure stereoisomer, pharmaceutically acceptable salt, solvate, or prodrug thereof.

Further disclosed herein is a compound with the following structure.

Compound 04-3

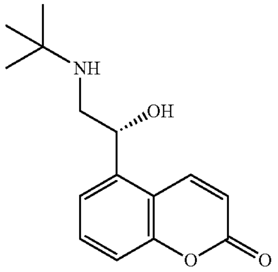

or an optically pure stereoisomer, pharmaceutically acceptable salt, solvate, or prodrug thereof.

Further disclosed herein is a compound with the following structure:

Compound 04-4

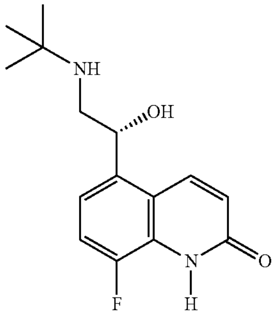

or an optically pure stereoisomer, pharmaceutically acceptable salt, solvate, or prodrug thereof.

Further disclosed herein is a compound with the following structure:

Compound 04-5

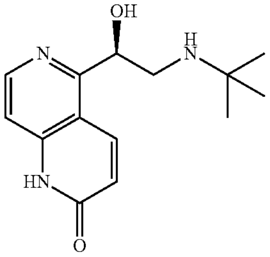

or an optically pure stereoisomer, pharmaceutically acceptable salt, solvate, or prodrug thereof.

Also disclosed herein is a compound according to Formula (IV'):

Formula (IV')

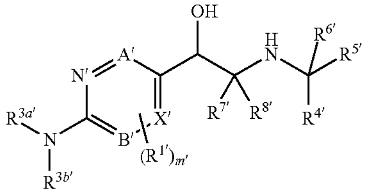

or a pharmaceutically acceptable salt thereof, wherein:

A', B', and X' are each independently a nitrogen atom or carbon atom;

each $R^{1'}$ is independently hydrogen, halogen, $R^A$, —CN, $—NO_2$, $—SF_5$, —O—, —OR', $—NR'_2$, $—SO_2R'$, —C(O)R', $—C(O)NR'_2$, —NR'C(O)R', $—NR'CO_2R'$, or $—CO_2R'$;

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{3a'}$ and $R^{3b'}$ are independently hydrogen, $R^A$, —OR', —C(O)R', —C(O)NR'$_2$, or —$CO_2$R', or:

$R^{3a'}$ and $R^{3b'}$ are optionally taken together with their intervening atoms to form an optionally substituted 4-10 membered saturated or partially unsaturated carbocyclic or heterocyclic ring having 1-3 heteroatoms, in addition to the nitrogen from which $R^{3a'}$ and $R^{3b'}$ are attached, independently selected from nitrogen, oxygen, and sulfur;

$R^{4'}$, $R^{5'}$, and $R^{6'}$ are each independently selected from hydrogen, halogen, $R^A$, —CN, —$NO_2$, —OR', —NR'$_2$,

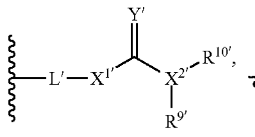
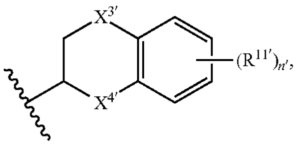
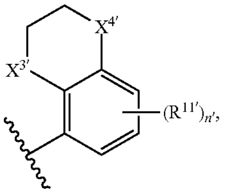
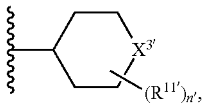
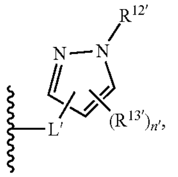
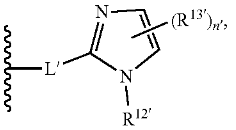
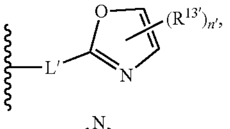
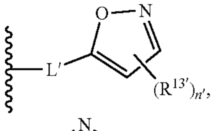
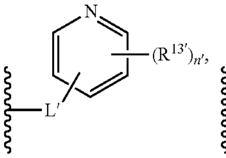
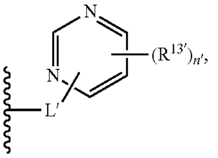
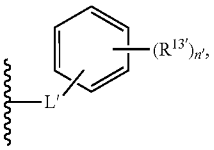
and
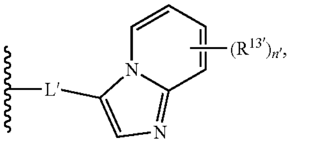

or:

$R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or a partially unsaturated monocyclic heterocyclic ring having 1-2 heteroatoms independently selected from nitrogen, oxygen, and sulfur;

L' is an optionally substituted $C_{1-5}$ alkylene;

$X^{1'}$, $X^{3'}$, and $X^{4'}$ are each independently a bivalent group selected from a covalent bond, —CR'$_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —NR'$_2$, or —OR';

n' is an integer selected from 0 to 4;

$R^{12'}$ is hydrogen, $R^A$, or —CN;

each $R^{13'}$ is independently hydrogen, halogen, $R^A$, —CN, —OR', or —NR'$_2$; and $R^{7'}$ and $R^{8'}$ are each independently hydrogen or optionally substituted $C_{1-2}$ aliphatic.

Also disclosed herein is a compound according to Formula (V'):

Formula (V')

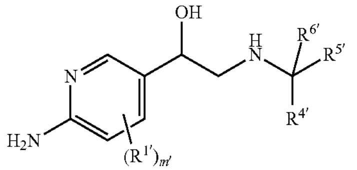

or a pharmaceutically acceptable salt thereof, wherein:

each $R^{1'}$ is independently hydrogen, halogen, $R^A$, —CN, —$NO_2$, —$SF_5$, —OR', —NR'$_2$, —$SO_2$R', —C(O)R', —C(O)NR'$_2$, —NR'C(O)R', —NR'$CO_2$R', or —$CO_2$R';

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{4'}$, $R^{5'}$, and $R^{6'}$ are each independently selected from hydrogen, halogen, $R^A$, —CN, —$NO_2$, —OR', —$NR'_2$,

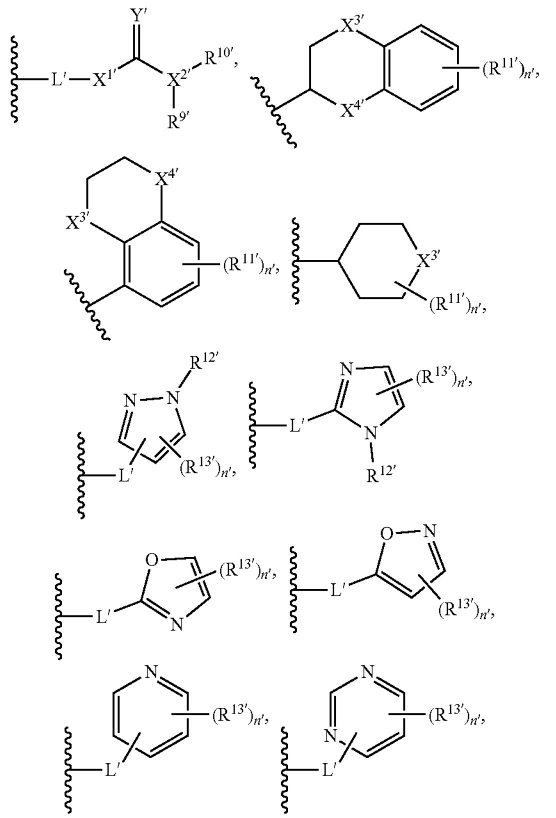

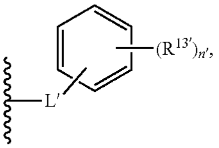

and

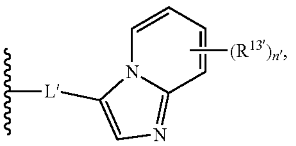

or:

$R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or a partially unsaturated monocyclic heterocyclic ring having 1-2 heteroatoms independently selected from nitrogen, oxygen, and sulfur;

L is an optionally substituted $C_{1-5}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

$Y^{1'}$ is O or S;

$R^{9'}$ and $R^{10'}$ are each independently hydrogen or optionally substituted alkyl, or:

$R^{9'}$ and $R^{10'}$ are cyclically linked and, together with $X^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12}$ is hydrogen, $R^A$, or —CN; and each $R^{13'}$ is independently hydrogen, halogen, $R^A$, —CN, —OR', or —$NR'_2$.

Further disclosed herein is a compound with the following structure:

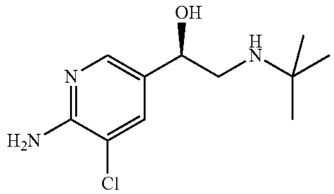 [SMILES: CC(C)(C)NC[C@H](O)c1cnc(N)c(Cl)c1]

or a pharmaceutically acceptable salt thereof.

Further disclosed herein is a compound with the following structure:

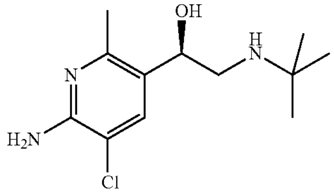 [SMILES: Cc1nc(N)c(Cl)cc1[C@@H](O)CNC(C)(C)C]

or a pharmaceutically acceptable salt thereof.

Further disclosed herein is a compound according to Formula (VI'):

Formula (VI')

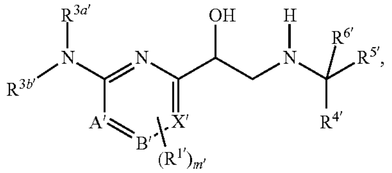

or a pharmaceutically acceptable salt thereof, wherein each of A', B', X', $R^{1'}$, $R^{3a'}$, $R^{3b'}$, $R^{4'}$, $R^{5'}$, $R^{6'}$, and m' is as defined above and as described in embodiments provided herein, both singly and in combination.

Further disclosed herein is a compound according to Formula (VII'):

Formula (VII')

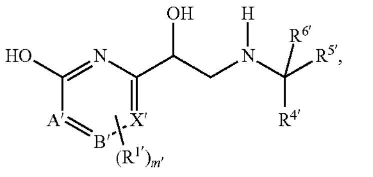

or a pharmaceutically acceptable salt thereof, wherein each of A', B', X', $R^{1'}$, $R^{4'}$, $R^{5'}$, $R^{6'}$, and m' is as defined above and as described in embodiments provided herein, both singly and in combination.

Also disclosed herein is a pharmaceutical composition including a compound as disclosed herein, i.e., a compound with a structure of Formula (I), Formula (I'), Formula (II), Formula (II'), Formula (III'), Formula (IV'), Formula (V'), Formula (VI'), Formula (VII'), or a pharmaceutically acceptable excipient.

In certain embodiments a compound as disclosed herein is an agonist, partial agonist or antagonist of an adrenergic receptor; in some embodiments the compound is a β1-adrenergic receptor agonist, β2-adrenertic receptor agonist or non-selective β1/β2-adrenergic receptor agonist; in some embodiments the compound is a β1-adrenergic receptor agonist; in some embodiments the compound is a β2-adrenergic receptor agonist; in some embodiments the compound is a compound is a non-selective β1/β2-adrenergic agonist.

Further disclosed is a method of treating a subject with a disease, the method including administering to the subject a therapeutically effective amount of a compound as disclosed herein, i.e., a compound with a structure of Formula (I), Formula (I'), Formula (II), Formula (II'), Formula (III'), Formula (IV'), Formula (V'), Formula (VI'), or Formula (VII'). In some embodiments, the disease is a disease associated with an adrenergic or receptor. In some embodiments, the disease is a neurodegenerative disease. In some embodiments, the subject is a human.

In some embodiments, the disease is selected from myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis. In some embodiments, the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intraarticular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

In some embodiments, the disease is a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS). In some embodiments the disease is a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the subject does not have Alzheimer's disease (AD). In some embodiments the subject does not have Down Syndrome.

In certain embodiments of the methods disclosed herein, the methods include administering to the subject a compound as disclosed herein and a peripherally acting β-blocker (PABRA).

As used herein, the term "peripherally acting β-blocker (PABRA)" means a β adrenergic receptor antagonist or simply a β1-, β2- or non-selective β-blocker. Examples of selective peripherally acting β-blockers (PABRA) that may in certain embodiments be used in the methods disclosed herein include nadolol, atenolol, sotalol and labetalol. In certain embodiments a β-blocker that can be used in the methods herein is one or more selected from the group consisting of acebutolol, betaxolol, bisoprolol, celiprolol, esmolol, metaprolol ad nevivolol; in other embodiments the methods do not use acebutolol, betaxolol, bisoprolol, celiprolol, esmolol, metaprolol or nevivolol as a β-blocker.

In certain embodiments a peripherally acting β-blocker (PABRA) is administered to the subject prior to administration of a compound of the disclosure; in other embodiments a peripherally acting β-blocker (PABRA) is administered to the subject concurrently with the administration of a compound of the disclosure.

In certain embodiments of the compositions and methods provided herein, one or more peripherally acting β-blockers (PABRA) are administered prior to or concurrently with a compound of the disclosure in order to inhibit or preclude agonism of peripheral β1 and/or β2 adrenergic receptors by a compound of the disclosure. In various embodiments it is preferred to block peripheral β1 and/or β2 adrenergic receptors in accordance with the compositions and methods of the present disclosure in order to preclude, or at least minimize, any adverse peripheral cardiac, metabolic or muscular effects on humans being treated.

In some embodiments of the methods provided herein, a β1 agonist, a β2 agonist, or a non-selective β1/β2 agonist is administered to the patient in addition to a compound as disclosed herein.

As used herein, the term "β1 agonist" is used to mean β1-adrenergic receptor agonist or β1-ADR agonist. In certain embodiments the term β1 agonist is understood to include compounds that are primarily β1 agonists, but which may also exhibit some peripheral agonism for other adrenergic receptors, such as β2-adrenergic receptors. In this application, the terms "β1-adrenergic receptor agonist", "β1-ADR agonist", "β1AR agonist" and "β1 agonist" may be used interchangeably. In certain embodiments, the term β1-ADR agonist expressly includes both selective and partial agonists, as well as biased and non-biased agonists. Examples of β1 adrenergic agonists include, for example, xamoterol, noradrenalin, isoprenaline, dopamine, pindolol and dobutamine and the pharmaceutically-acceptable salts of any of the above. Partial agonists and ligands of the β1-ADR are known. Further, using the methodology of Kolb et al, but for β1-ADR instead, one skilled in the art could determine new ligands by structure-based discovery. See Proc. Nat. Acad. Sci. USA 2009, 106, 6843-648.

As used herein, the term β2 agonist is used to mean β2-adrenergic receptor agonist or β2-ADR agonist. In certain embodiments, the term β2 agonist is understood to include compounds that are primarily β2 agonists, but which may also exhibit some peripheral agonism for other adrenergic receptors, such as β1-adrenergic receptors. In this application the terms "β2-adrenergic receptor agonist", "β2-ADR agonist", "β2AR agonist" and "β2 agonist" may be used interchangeably. In some embodiments the term β2-ADR agonist expressly includes both selective and partial agonists. β2 agonists that may be used in accordance with various aspects and embodiments of the present disclosure may be short-acting, long-acting or ultra long-acting. Examples of short-acting β2 agonists that may be used are salbutamol, levosalbutamol, terbutaline, pirbuterol, procaterol, metaproterenol, bitolterol mesylate, oritodrine, isoprenaline, salmefamol, fenoterol, terbutaline, albuterol, and isoetharine. Examples of long-acting β2 agonists that may be used are salmeterol, bambuterol, formoterol and clenbuterol. Examples of ultra long-acting β2 agonists include indacaterol, vilanterol and olodaterol.

It was surprisingly found that compounds of the present disclosure exhibit unexpectedly beneficial properties, as demonstrated in the Examples section herein. For instance, it was surprisingly found that compounds of the present disclosure act as low nM (<10 nM) partial agonists of the β2 adrenergic receptor.

DETAILED DESCRIPTION

In the following detailed description of the embodiments of the instant disclosure, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the instant disclosure.

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements. The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment. A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art. All publications, patent applications, patents, and other references mentioned herein are incorporated by reference in their entirety. All sequences provided in the disclosed Genbank Accession numbers are incorporated herein by reference as available on Aug. 11, 2011. In case of conflict, the present specification, including explanations of terms, will control. In addition, the materials, methods, and examples are illustrative only and not intended to be limiting.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multi-cyclic ring systems include, but are not limited to, bicycle [4.4.0]decane, bicycle[2.2.1]heptane, spiro[2.2]pentane, and the like. (Cycloalkyl)oxy refers to —O-cycloalkyl. (Cycloalkyl)thio refers to —S-cycloalkyl. This term also encompasses oxidized forms of sulfur, such as —S(O)—cycloalkyl, or —$S(O)_2$-cycloalkyl.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, —$CH{=}CH(CH_3)$, —$CH{=}C(CH_3)_2$, —$C(CH_3){=}CH_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and —$C{\equiv}C(CH_3)$, among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups. Aryloxy refers to —O-aryl. Arylthio refers to —S-aryl, wherein aryl is as defined herein. This term also encompasses oxidized forms of sulfur, such as —S(O)-aryl, or —$S(O)_2$-aryl. Heteroaryloxy refers to —O-heteroaryl. Heteroarylthio refers to —S-heteroaryl. This term also encompasses oxidized forms of sulfur, such as —S(O)—heteroaryl, or —$S(O)_2$-heteroaryl. N-oxides are also contemplated. In some embodiments, a compound of the present disclosure is in the form of an N-oxide.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups. Heterocyclyloxy refers to —O-heterocycyl. Heterocyclylthio refers to —S-heterocycyl. This term also encompasses oxidized forms of sulfur, such as —S(O)-heterocyclyl, or —$S(O)_2$-heterocyclyl.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —$NO_2$; cyano group refers to —CN; isocyano group refers to —N—C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

Thiol refers to —SH. Thiocarbonyl refers to (═S). Sulfonyl refers to —$SO_2$-alkyl, —$SO_2$-substituted alkyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclyl, and —$SO_2$-substituted heterocyclyl. Sulfonylamino refers to —$NR^aSO_2$alkyl, —$NR^aSO_2$-substituted alkyl, —$NR^aSO_2$cycloalkyl, —$NR^aSO_2$ substituted cycloalkyl, —$NR^aSO_2$aryl, —$NR^aSO_2$ substituted aryl, —$NR^aSO_2$heteroaryl, —$NR^aSO_2$ substituted heteroaryl, —$NR^aSO_2$heterocyclyl, —$NR^aSO_2$ substituted heterocyclyl, wherein each $R^a$ independently is as defined herein.

Carboxyl refers to —COOH or salts thereof. Carboxyester refers to —C(O)O-alkyl, —C(O)O— substituted alkyl, —C(O)O-aryl, —C(O)O-substituted aryl, —C(O)O-cycloalkyl, —C(O)O— substituted cycloalkyl, —C(O)O-heteroaryl, —C(O)O-substituted heteroaryl, —C(O)O— heterocyclyl, and —C(O)O-substituted heterocyclyl. (Carboxyester)amino refers to —$NR^a$—C(O)O-alkyl, —$NR^a$—C(O)O-substituted alkyl, —$NR^a$—C(O)O-aryl, —$NR^a$—C(O)O-substituted aryl, —$NR^a$—C(O)β-cycloalkyl, —$NR^a$—C(O)O-substituted cycloalkyl, —$NR^a$—C(O) O-heteroaryl, —$NR^a$—C(O)O-substituted heteroaryl, —$NR^a$—C(O)O-heterocyclyl, and —$NR^a$—C(O)O-substituted heterocyclyl, wherein $R^a$ is as recited herein. (Carboxyester)oxy refers to —O—C(O)O-alkyl, —O—C(O) O— substituted alkyl, —O—C(O)O-aryl, —O—C(O)O-substituted aryl, —O—C(O)O-cycloalkyl, —O—C(O)O-substituted cycloalkyl, —O—C(O)O-heteroaryl, —O—C (O)O-substituted heteroaryl, —O—C(O)O-heterocyclyl, and —O—C(O)O-substituted heterocyclyl. Oxo refers to (═O).

The terms "amine" and "amino" refer to derivatives of ammonia, wherein one of more hydrogen atoms have been replaced by a substituent which include, but are not limited to alkyl, alkenyl, aryl, and heterocyclyl groups. In some embodiments, substituted amino can include —NH—CO—R. Carbamate groups refers to —O(C═O)$NR_1R_2$, where $R_1$ and $R_2$ are independently hydrogen, aliphatic groups, aryl groups, or heterocyclyl groups.

Aminocarbonyl refers to —C(O)$N(R^b)_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen. Aminocarbonylalkyl refers to -alkylC(O)$N(R^b)_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen. Aminocarbonylamino refers to —$NR^a$C(O)$N(R^b)_2$, wherein $R^a$ and each $R^b$ are as defined herein. Aminodicarbonylamino refers to —$NR^a$C(O)C(O)$N(R^b)_2$, wherein $R^a$ and each $R^b$ are as defined herein. Aminocarbonyloxy refers to —O—C(O)$N(R^b)_2$, wherein each $R^b$ independently is as defined herein. Aminosulfonyl refers to —$SO_2N(R^b)_2$, wherein each $R^b$ independently is as defined herein.

Imino refers to —N═$R^c$ wherein $R^c$ may be selected from hydrogen, aminocarbonylalkyloxy, substituted aminocarbonylalkyloxy, aminocarbonylalkylamino, and substituted aminocarbonylalkylamino.

As described herein, compounds of the present disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR^{\circ}$; $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$; —$(CH_2)_{0-4}OC(O)NR^{\circ}_2$; —C(O) $N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$S(O)(NR^{\circ})R^{\circ}$; —$S(O)_2N$═$C(NR^{\circ}_2)_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; —$SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^c$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{\bullet}$; -(halo$R^{\bullet}$); —$(CH_2)_{0-2}OH$; —$(CH_2)_{0-2}OR^{\bullet}$; —$(CH_2)_{0-2}CH(OR^{\bullet})_2$; —O(halo$R^{\bullet}$); —CN; —$N_3$; —$(CH_2)_{0-2}C(O)R^{\bullet}$; —$(CH_2)_{0-2}C(O)OH$; —$(CH_2)_{0-2}C(O)OR^{\bullet}$; —$(CH_2)_{0-2}SR^{\bullet}$; —$(CH_2)_{0-2}SH$; —$(CH_2)_{0-2}NH_2$; —$(CH_2)_{0-2}NHR^{\bullet}$; —$(CH_2)_{0-2}NR^{\bullet}_2$; —$NO_2$, —$SiR^{\bullet}_3$; —$OSiR^{\bullet}_3$; —$C(O)SR^{\bullet}$; —($C_{1-4}$ straight or branched alkylene)C(O)$OR^{\bullet}$; or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur. Suitable divalent substituents on a saturated carbon atom of $R^{\circ}$ include ═O and ═S.

Suitable divalent substituents on a saturated carbon atom of an "optionally substituted" group include the following: ═O; ═S; ═$NNR^*_2$; ═NNHC(O)$R^*$; ═NNHC(O)$OR^*$; ═$NNHS(O)_2R^*$; ═$NR^*$; ═$NOR^*$; —$O(C(R^*_2))_{2-3}O$—; or —$S(C(R^*_2))_{2-3}S$—; wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$; -(halo$R^\bullet$); —OH, —$OR^\bullet$; —O(halo$R^\bullet$); —CN; —C(O)OH; —C(O)$OR^\bullet$; —$NH_2$; —$NHR^\bullet$; —$NR^\bullet_2$; or —$NO_2$; wherein each $R^\bullet$ is unsubstituted or where preceded by "halo" is substituted only with one or more halogens, and is independently $C_{1-4}$ aliphatic, —$CH_2Ph$; —$O(CH_2)_{0-1}Ph$; or a 5-6-membered saturated; partially unsaturated; or aryl ring having 0-4 heteroatoms independently selected from nitrogen, oxygen, or sulfur.

Suitable substituents on a substitutable nitrogen of an "optionally substituted" group include —$R^\dagger$; —$NR^\dagger_2$; —C(O)$R^\dagger$; —C(O)$OR^\dagger$; —C(O)C(O)$R^\dagger$; —C(O)$CH_2$C(O)$R^\dagger$; —$S(O)_2R^\dagger$; —$S(O)_2NR^\dagger_2$; —C(S)$NR^\dagger_2$; —C(NH)$NR^\dagger_2$; or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$; -(halo$R^\bullet$); —OH; —$OR^\bullet$; —O(halo$R^\bullet$); —CN; —C(O)OH; —C(O)$OR^\bullet$; —$NH_2$; —$NHR^\bullet$; —$NR^\bullet_2$; or —$NO_2$; wherein each $R^\bullet$ is unsubstituted or where preceded by "halo" is substituted only with one or more halogens, and is independently $C_{1-4}$ aliphatic, —$CH_2Ph$; —$O(CH_2)_{0-1}Ph$; or a 5-6-membered saturated; partially unsaturated; or aryl ring having 0-4 heteroatoms independently selected from nitrogen, oxygen, or sulfur.

Additionally, unless otherwise stated, structures depicted herein are also meant to include compounds that differ only in the presence of one or more isotopically enriched atoms. For example, compounds having the present structures including the replacement of hydrogen by deuterium (e.g., D or $H^2$) or tritium (e.g., T or $H^3$), or the replacement of a carbon by a $^{13}C$- or $^{14}C$-enriched carbon are included and are within the scope of this disclosure. Such compounds are useful, for example, as analytical tools, as probes in biological assays, or as therapeutic agents in accordance with the present disclosure Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

Disclosed herein is a compound according to Formula (I) or an optically pure stereoisomer, pharmaceutically acceptable salt, solvate, or prodrug thereof Formula (I)

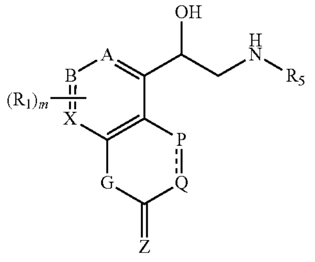

In some embodiments of Formula (I), each $R_1$ is independently selected from the group consisting of hydrogen, halogen, cyano, nitro, unsubstituted or substituted amino, pentafluorosulfanyl, unsubstituted or substituted sulfonyl, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl.

In some embodiments of Formula (I), m is an integer selected from 0 to 3.

In some embodiments of Formula (I), each A, B, and X is independently a nitrogen or carbon.

In some embodiments of Formula (I), P is N, O, or $CR_2$; Q is N, O, or $CR_2$; G is $NR_5$ or O; and/or Z is $NR_5$, O, S, or $CR_3R_4$. In some embodiments, $R_2$ is selected from the group consisting of hydrogen, halogen, cyano, nitro, hydroxyl, unsubstituted or substituted amino, unsubstituted or substituted alkyl, and unsubstituted or substituted alkoxy. In certain embodiments, each $R_3$ and $R_4$ is selected from the group consisting of hydrogen, halogen, cyano, nitro, hydroxyl, unsubstituted or substituted amino, unsubstituted or substituted alkyl, and unsubstituted or substituted alkoxy.

In some embodiments of Formula (I), $R_5$ is one or more selected from the group consisting of H, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

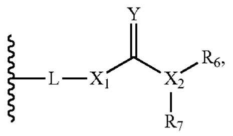

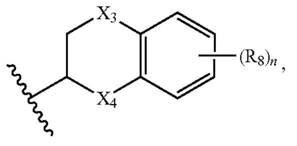

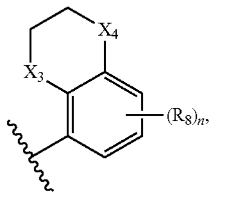

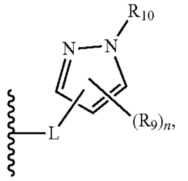

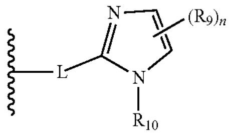

,

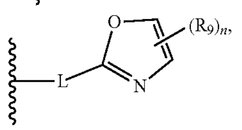

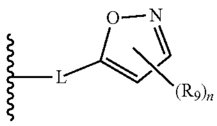

,

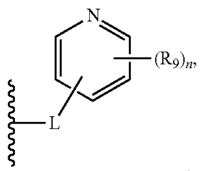

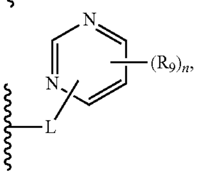

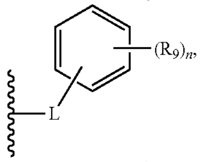

and

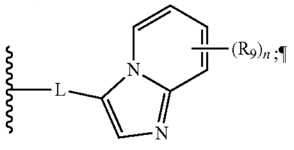

L is a C1-C5 alkyl linker optionally substituted; each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl; Y is O or S; $R_6$ and $R_7$ are independently selected from hydrogen, unsubstituted or substituted alkyl, or $R_6$ and $R_7$ are cyclically linked and together with $X_2$ to form an optionally substituted cycloalkyl or heterocycle; each $R_8$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl; n is an integer selected from 0 to 4; $R_9$ is selected from the group consisting of hydrogen, halogen, cyano, unsubstituted or substituted alkyl, unsubstituted or substituted alkoxy, and unsubstituted or substituted amino; and $R_{10}$ is selected from the group consisting of hydrogen, cyano, unsubstituted or substituted alkyl, and unsubstituted or substituted alkoxy.

Also disclosed herein is a compound according to Formula (II) or an optically pure stereoisomer, pharmaceutically acceptable salt, solvate, or prodrug thereof Formula (II)

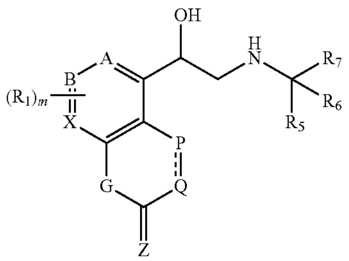

In some embodiments of Formula (II), each $R_1$ is independently selected from the group consisting of hydrogen, halogen, cyano, nitro, unsubstituted or substituted amino, pentafluorosulfanyl, unsubstituted or substituted sulfonyl, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl.

In some embodiments of Formula (II), m is an integer selected from 0 to 3.

In some embodiments of Formula (II), each A, B, and X is independently a nitrogen or carbon.

In some embodiments of Formula (II), P is N, O, or $CR_2$; Q is N, O, or $CR_2$; G is $NR_5$ or O; and/or Z is $NR_5$, O, S, or $CR_3R_4$.

In some embodiments of Formula (II), $R_2$ is selected from the group consisting of hydrogen, halogen, cyano, nitro, hydroxyl, unsubstituted or substituted amino, unsubstituted or substituted alkyl, and unsubstituted or substituted alkoxy.

In some embodiments of Formula (II), each $R_3$ and $R_4$ is selected from the group consisting of hydrogen, halogen, cyano, nitro, hydroxyl, unsubstituted or substituted amino, unsubstituted or substituted alkyl, and unsubstituted or substituted alkoxy.

In some embodiments of Formula (II), $R_5$, $R_6$, and $R_7$ are independently selected from the group consisting of H, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

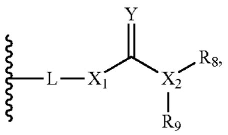

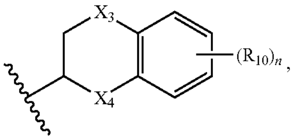

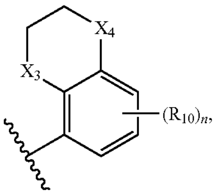

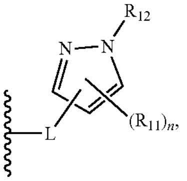

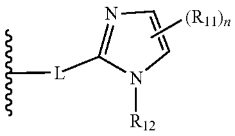

,

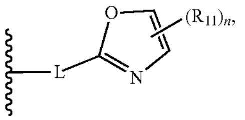

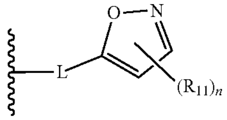

,

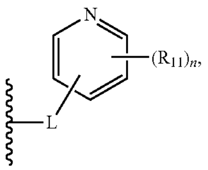

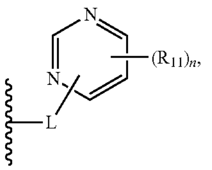

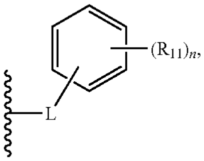

and

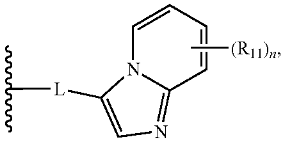

or $R_5$ and $R_6$ together with the carbon form an unsubstituted or substituted 3-7 membered cycloalkyl or heterocycle ring; L is a C1-C5 alkyl linker optionally substituted; each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl; Y is O or S; $R_8$ and $R_9$ are independently selected from hydrogen, unsubstituted or substituted alkyl, or $R_8$ and $R_9$ are cyclically linked and together with $X_2$ to form an optionally substituted cycloalkyl or heterocycle; each $R_{10}$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl; n is an integer selected from 0 to 4; $R_{11}$ is selected from the group consisting of hydrogen, halogen, cyano, unsubstituted or substituted alkyl, unsubstituted or substituted alkoxy, and unsubstituted or substituted amino; and $R_{12}$ is selected from the group consisting of hydrogen, cyano, unsubstituted or substituted alkyl, and unsubstituted or substituted alkoxy.

Also disclosed herein is a compound according to Formula (I'):

Formula (I')

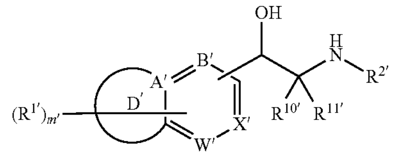

or a pharmaceutically acceptable salt, wherein:

A', B', W', and X' are each independently a nitrogen atom or carbon atom;

Ring D' is a fused ring selected from benzo, 5-9 membered monocyclic or bicyclic heteroaryl containing 1-4 heteroatoms independently selected from nitrogen, oxygen, or sulfur, and a 5 to 7-membered saturated or partially unsaturated carbocyclyl or heterocyclyl having 1-3 heteroatoms independently selected from nitrogen, oxygen, or sulfur;

each $R^{1'}$ is independently hydrogen, halogen, $R^A$, —CN, —$NO_2$, —$SF_5$, —O—, —OR', —$NR'_2$, —$SO_2R'$, —C(O)R', —C(O)$NR'_2$, —NR'C(O)R', —NR'$CO_2$R', or —$CO_2$R';

each $R^A$ is independently an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two $R^A$ groups on the same carbon or are optionally taken together with their intervening atoms to form an optionally substituted 3-6 membered saturated or partially unsaturated carbocyclic or heterocyclic ring having 1-3 heteroatoms, in addition to the carbon from which the two $R^A$ groups are attached, independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{2'}$ is selected from hydrogen, $R^A$, —OR',

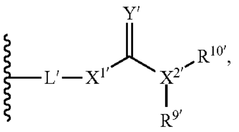
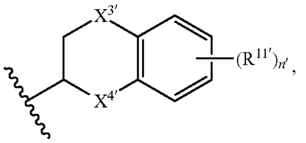
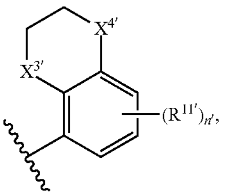
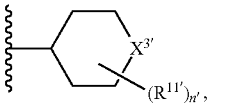
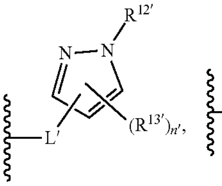
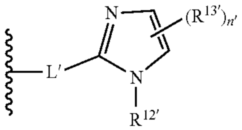
,
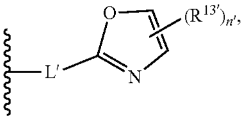
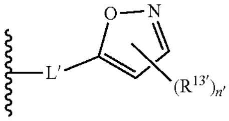
,
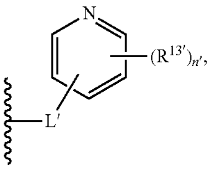
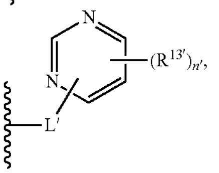
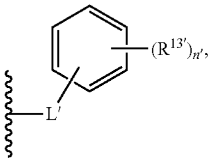
and
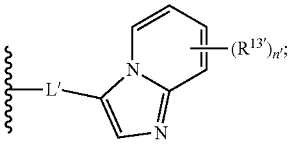

L' is an optionally substituted $C_{1-5}$ alkylene;

$X^{1'}$, $X^{3'}$, and $X^{4'}$ are each independently a bivalent group selected from a covalent bond, —CR'$_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^2$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{1'}$ is independently $R^A$, halogen, —CN, —$NO_2$, —NR'$_2$, or —OR';

n' is an integer selected from 0 to 4;

$R^{12'}$ is hydrogen, $R^A$, or —CN;

each $R^{13'}$ is independently hydrogen, halogen, $R^A$, —CN, —OR', or —NR'$_2$; and $R^{7'}$ and $R^{8'}$ are each independently hydrogen or optionally substituted $C_{1-2}$ aliphatic.

Also disclosed herein is a compound according to Formula (II'):

Formula (II')

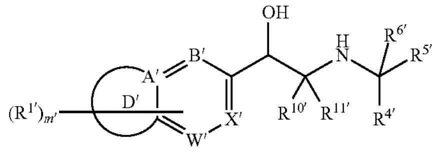

or a pharmaceutically acceptable salt, wherein:

A', B', W', and X' are each independently a nitrogen atom or carbon atom;

Ring D' is a fused ring selected from benzo, 5-9 membered monocyclic or bicyclic heteroaryl containing 1-4 heteroatoms independently selected from nitrogen, oxygen, or sulfur, and a 5 to 7-membered saturated or partially unsaturated carbocyclyl or heterocyclyl having 1-3 heteroatoms independently selected from nitrogen, oxygen, or sulfur;

each $R^{1'}$ is independently hydrogen, halogen, $R^A$, —CN, —$NO_2$, —$SF_5$, —O—, —OR', —NR'$_2$, —$SO_2$R', —C(O)R', —C(O)NR'$_2$, —NR'C(O)R', —NR'$CO_2$R', or —$CO_2$R';

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two $R^A$ groups on the same carbon or are optionally taken together with their intervening atoms to form an optionally substituted 3-6 membered saturated or partially unsaturated carbocyclic or heterocyclic ring having 1-3 heteroatoms, in addition to the carbon from which the two $R^A$ groups are attached, independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{4'}$, $R^{5'}$, and $R^{6'}$ are each independently selected from hydrogen, halogen, $R^A$, —CN, —$NO_2$, —OR', —$NR'_2$,

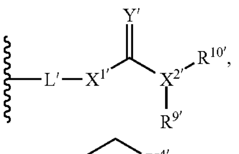
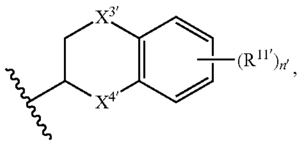
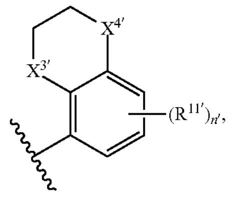
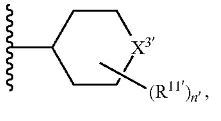
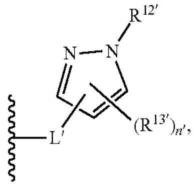
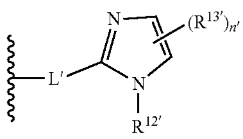
,
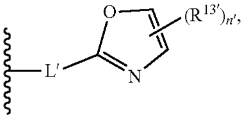
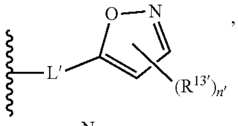
,
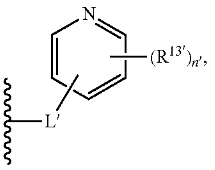
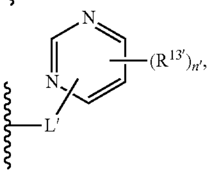
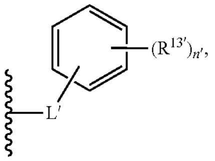
and
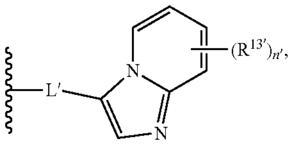

or:

$R^{4'}$ and $R^{5'}$ are optionally taken together with the carbon to which they are attached to form an optionally substituted ring selected from 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is an optionally substituted $C_{1-5}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^2$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12'}$ is hydrogen, $R^A$, or —CN;

each $R^{13'}$ is independently hydrogen, halogen, $R^A$, —CN, —OR', or —$NR'_2$; and $R^{7'}$ and $R^{8'}$ are each independently hydrogen or optionally substituted $C_{1-2}$ aliphatic.

Also disclosed herein is a compound according to Formula (III'):

Formula (III')

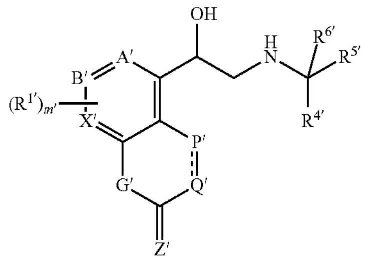

or a pharmaceutically acceptable salt thereof, wherein:

A', B', and X' are each independently a nitrogen atom or carbon atom;

P' and Q' are each independently —N═, —NR'—, —CR'═, or —$CR'_2$—;

G' is —NR'— or —O—;

Z' is ═NR', ═O, ═S, or ═$CR'_2$;

$\overline{\underline{---}}$ is a single bond or double bond;

each $R^{1'}$ is independently hydrogen, halogen, $R^A$, —CN, —$NO_2$, —$SF_5$, —OR', —$NR'_2$, —$SO_2R'$, —C(O)R', —C(O)$NR'_2$, —NR'C(O)R', —NR'$CO_2R'$, or —$CO_2R'$;

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{4'}$, $R^{5'}$, and $R^{6'}$ are each independently selected from hydrogen, halogen, $R^A$, —CN, —$NO_2$, —OR', —$NR'_2$,

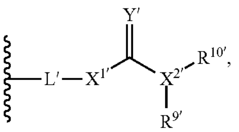

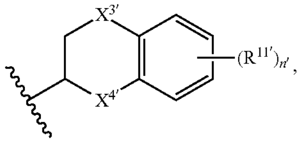

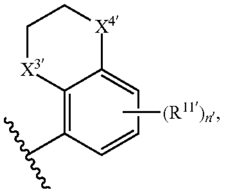

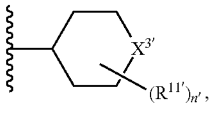

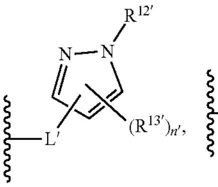

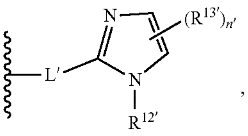

,

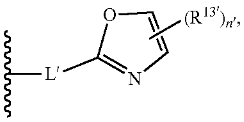

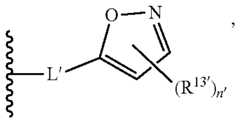

,

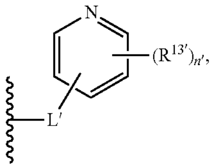

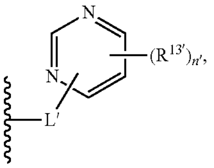

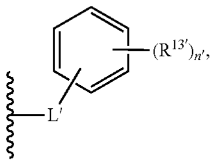

and

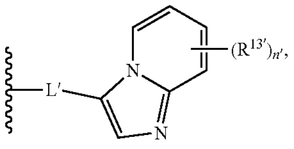

or:

$R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or a partially unsaturated monocyclic heterocyclic ring having 1-2 heteroatoms independently selected from nitrogen, oxygen, and sulfur;

L' is an optionally substituted $C_{1-6}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12'}$ is hydrogen, $R^A$, or —CN; and each $R^{13'}$ is independently hydrogen, halogen, $R^A$, —CN, —OR', or —$NR'_2$.

Also disclosed herein is a compound according to Formula (IV'):

Formula (IV')

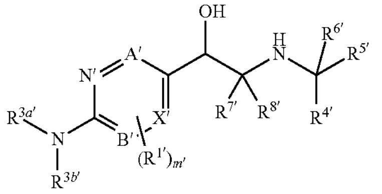

or a pharmaceutically acceptable salt thereof, wherein:

A', B', and X' are each independently a nitrogen atom or carbon atom;

each $R^{1'}$ is independently hydrogen, halogen, $R^A$, —CN, —$NO_2$, —$SF_5$, —O—, —OR', —$NR'_2$, —$SO_2R'$, —C(O)R', —C(O)$NR'_2$, —NR'C(O)R', —$NR'CO_2R'$, or —$CO_2R'$;

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{3a'}$ and $R^{3b'}$ are independently hydrogen, $R^A$, —OR', —C(O)R', —C(O)NR'$_2$, or —$CO_2$R', or:

$R^{3a'}$ and $R^{3b'}$ are optionally taken together with their intervening atoms to form an optionally substituted 4-10 membered saturated or partially unsaturated carbocyclic or heterocyclic ring having 1-3 heteroatoms, in addition to the nitrogen from which $R^{3a'}$ and $R^{3b'}$ are attached, independently selected from nitrogen, oxygen, and sulfur;

$R^{4'}$, $R^{5'}$, and $R^{6'}$ are each independently selected from hydrogen, halogen, $R^A$, —CN, —$NO_2$, —OR', —NR'$_2$,

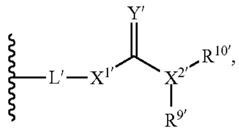
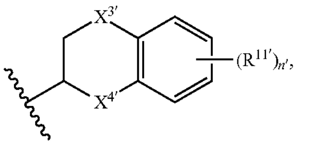
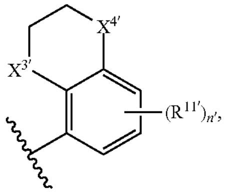
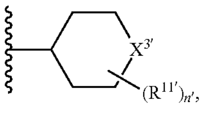
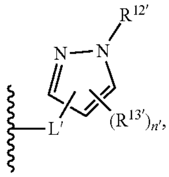
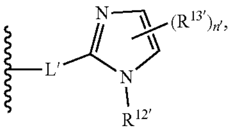
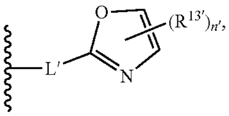
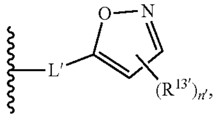
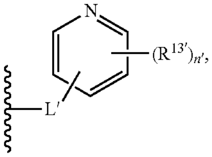
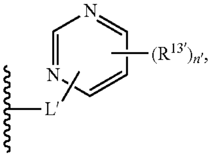
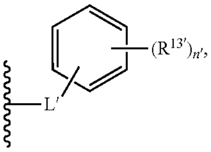
and
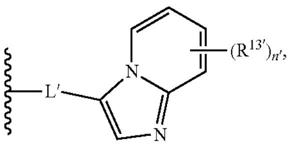

or:

$R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or a partially unsaturated monocyclic heterocyclic ring having 1-2 heteroatoms independently selected from nitrogen, oxygen, and sulfur;

L' is an optionally substituted $C_{1-5}$ alkylene;

$X^{1'}$, $X^{3'}$, and $X^{4'}$ are each independently a bivalent group selected from a covalent bond, —CR'$_2$—, —O—, and —NR'—;

$X^{2'}$ is a carbon atom or nitrogen atom;

Y' is O or S;

$R^{9'}$ and $R^{10'}$ are each independently hydrogen or optionally substituted alkyl, or:

$R^{9'}$ and $R^{10'}$ are cyclically linked and, together with $X^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —NR'$_2$, or —OR';

n' is an integer selected from 0 to 4;

$R^{12'}$ is hydrogen, $R^A$, or —CN;

each $R^{13'}$ is independently hydrogen, halogen, $R^A$, —CN, —OR', or —NR'$_2$; and $R^{7'}$ and $R^{8'}$ are each independently hydrogen or optionally substituted $C_{1-2}$ aliphatic.

Also disclosed herein is a compound according to Formula (V'):

Formula (V')

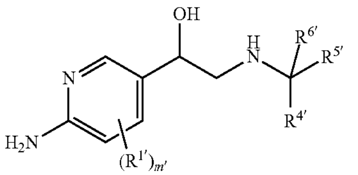

or a pharmaceutically acceptable salt thereof, wherein:

each $R^{1'}$ is independently hydrogen, halogen, $R^A$, —CN, —$NO_2$, —$SF_5$, —OR', —NR'$_2$, —$SO_2$R', —C(O)R', —C(O)NR'$_2$, —NR'C(O)R', —NR'$CO_2$R', or —$CO_2$R';

each $R^A$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R' is independently hydrogen or an optionally substituted group selected from $C_{1-6}$ aliphatic, phenyl, a 3-8 membered saturated or partially unsaturated monocyclic carbocyclic ring, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, and an 8-10 membered bicyclic partially unsaturated or heteroaromatic ring having 1-5 heteroatoms independently selected from nitrogen, oxygen, or sulfur, or:

two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur;

m' is an integer selected from 0 to 3;

$R^{4'}$, $R^{5'}$, and $R^{6'}$ are each independently selected from hydrogen, halogen, $R^A$, —CN, —$NO_2$, —OR', —$NR'_2$,

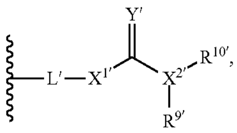
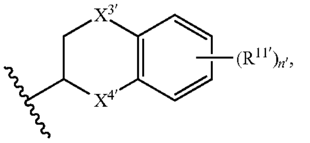
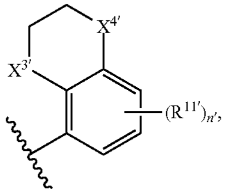
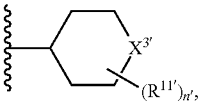
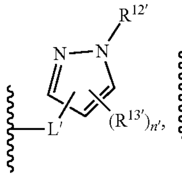
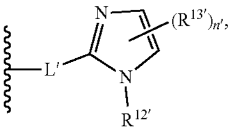
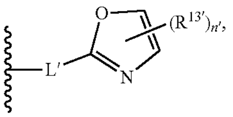
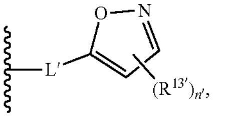
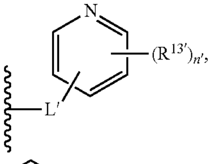
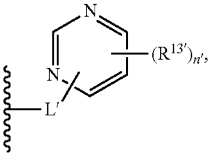
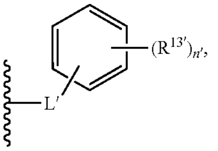
and
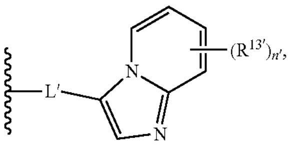

or:

$R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or a partially unsaturated monocyclic heterocyclic ring having 1-2 heteroatoms independently selected from nitrogen, oxygen, and sulfur;

L' is an optionally substituted $C_{1-5}$ alkylene;

$X^{1'}$, $X^{3'}$, and $X^{4'}$ are each independently a bivalent group selected from a covalent bond, —$CR'_2$—, —O—, and —NR'—;

$X^{2'}$ is a carbon atom or nitrogen atom;

$Y^{1'}$ is O or S;

$R^{9'}$ and $R^{10'}$ are each independently hydrogen or optionally substituted alkyl, or:

$R^{9'}$ and $R^{10'}$ are cyclically linked and, together with $X^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{11'}$ is independently $R^A$, halogen, —CN, —$NO_2$, —$NR'_2$, or —OR';

n' is an integer selected from 0 to 4;

$R^{12}$ is hydrogen, $R^A$, or —CN; and each $R^{13'}$ is independently hydrogen, halogen, $R^A$, —CN, —OR', or —$NR'_2$.

As defined above and described herein, A' is a nitrogen atom or a carbon atom.

In some embodiments A' is a nitrogen atom. In some embodiments, A' is a carbon atom.

In some embodiments A' is selected from those depicted in Table 1, below.

As defined above and described herein, B' is a nitrogen atom or a carbon atom.

In some embodiments B' is a nitrogen atom. In some embodiments, B' is a carbon atom.

In some embodiments B' is selected from those depicted in Table 1, below.

As defined above and described herein, X' is a nitrogen atom or a carbon atom.

In some embodiments X' is a nitrogen atom. In some embodiments, X' is a carbon atom.

In some embodiments X' is selected from those depicted in Table 1, below.

As defined above and described herein, W' is a nitrogen atom or a carbon atom.

In some embodiments W' is a nitrogen atom. In some embodiments, W' is a carbon atom.

In some embodiments W' is selected from those depicted in Table 1, below.

In some embodiments, any of the nitrogen atoms mentioned above is optionally in the form of an N-oxide.

As defined above and described herein, P' and Q' are each independently —N═, —NR'—, —CR'═, or —$CR'_2$—.

In some embodiments, P' is —N═. In some embodiments, P' is —NR'—. In some embodiments, P' is —CR'═. In some embodiments, P' is —$CR'_2$—. In some embodiments, P' is —CH═. In some embodiments, Q' is —N═. In some embodiments, Q' is —NR'—. In some embodiments, Q' is —CR'═. In some embodiments, Q is —$CR'_2$—. In some embodiments, Q' is —CH═.

In some embodiments P' and Q' are selected from those depicted in Table 1, below.

As defined above and described herein, G' is —NR'— or —O—.

In some embodiments, G' is —NR'—. In some embodiments, G' is —O—. In some embodiments, G' is —NH—. In some embodiments, G' is —NMe-.

In some embodiments G' is selected from those depicted in Table 1, below.

As defined above and described herein, Z' is =NR', =O, =S, or =CR'$_2$.

In some embodiments, Z is =NR'. In some embodiments, Z' is =O. In some embodiments, Z' is =S. In some embodiments, Z' is =CR'$_2$.

In some embodiments Z' is selected from those depicted in Table 1, below.

As defined above and described herein, === is a single bond or double bond.

In some embodiment, === is a single bond. In some embodiment, === is double bond.

In some embodiments === is selected from those depicted in Table 1, below.

As defined above and described herein, Ring D' is a fused ring selected from benzo, 5-9 membered monocyclic or bicyclic heteroaryl containing 1-4 heteroatoms independently selected from nitrogen, oxygen, or sulfur, and a 5 to 7-membered saturated or partially unsaturated carbocyclyl or heterocyclyl having 1-3 heteroatoms independently selected from nitrogen, oxygen, or sulfur.

In some embodiments, Ring D' is benzo. In some embodiments, Ring D' is a 5-9 membered monocyclic or bicyclic heteroaryl containing 1-4 heteroatoms independently selected from nitrogen, oxygen, or sulfur. In some embodiments, Ring D' is a 5 to 7-membered saturated or partially unsaturated carbocyclyl or heterocyclyl having 1-3 heteroatoms independently selected from nitrogen, oxygen, or sulfur. In some embodiments, Ring D' is

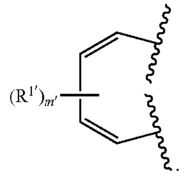

In some embodiments, Ring D' is

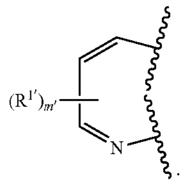

In some embodiments, Ring D' is

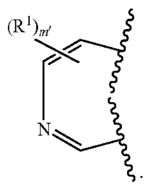

In some embodiments, Ring D' is

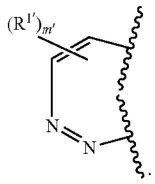

In some embodiments, Ring D' is

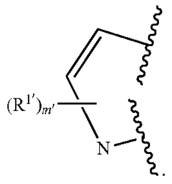

In some embodiments, Ring D' is

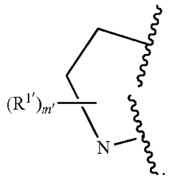

In some embodiments, Ring D' is

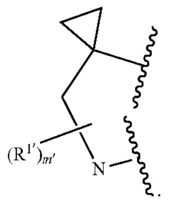

In some embodiments, Ring D' is

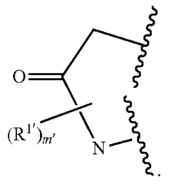

In some embodiments, Ring D' is

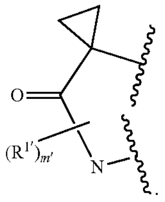

In some embodiments, Ring D' is

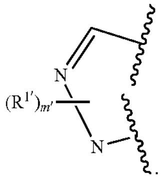

In some embodiments, Ring D' is

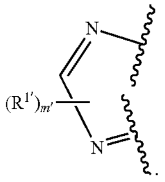

In some embodiments, Ring D' is

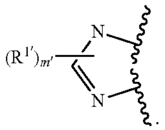

In some embodiments, Ring D' is

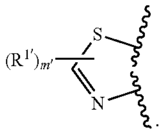

In some embodiments, Ring D' is

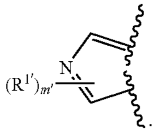

In some embodiments, Ring D' is

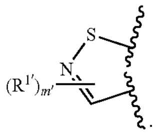

In some embodiments, Ring D' is

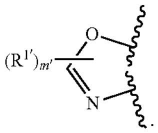

In some embodiments, Ring D' is

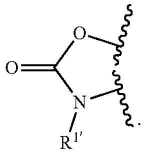

In some embodiments, Ring D' is

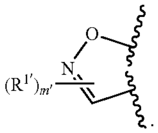

In some embodiments, Ring D' is

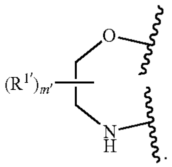

In some embodiments, Ring D' is

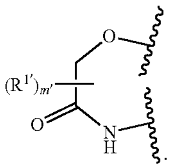

In some embodiments, Ring D' is

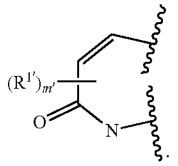

In some embodiments, Ring D' is

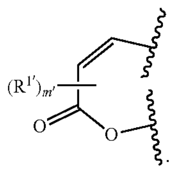

In some embodiments, Ring D' is

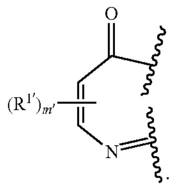

In some embodiments, Ring D' is

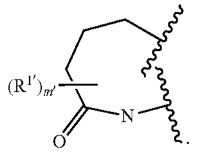

In some embodiments, Ring D' is

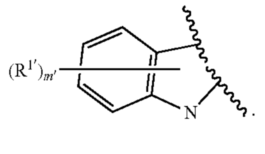

In some embodiments, Ring D' is

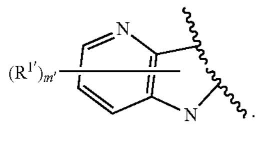

In some embodiments, Ring D' is

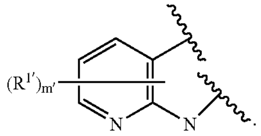

In some embodiments, Ring D' is

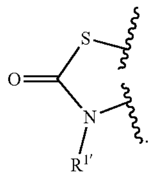

In some embodiments Ring D' is selected from those depicted in Table 1, below.

As defined above and described herein, each $R^{1'}$ is independently halogen, $R^{A}$, —CN, —$NO_2$, —$SF_5$, —O—, —OR', —$NR'_2$, —$SO_2R'$, —C(O)R', —C(O)$NR'_2$, —NR'C(O)R', —NR'$CO_2R'$, or —$CO_2R'$.

In some embodiments, $R^{1'}$ is hydrogen. In some embodiments, $R^{1'}$ is halogen. In some embodiments, $R^{1'}$ is $R^{A}$. In some embodiments, $R^{1'}$ is —CN. In some embodiments, $R^{1'}$ is —$NO_2$. In some embodiments, $R^{1'}$ is —$SF_5$. In some embodiments, $R^{1'}$ is —O—. In some embodiments, $R^{1'}$ is —OR'. In some embodiments, $R^{1'}$ is —$NR'_2$. In some embodiments, $R^{1'}$ is —$SO_2R'$. In some embodiments, $R^{1'}$ is —C(O)R'. In some embodiments, $R^{1'}$ is —C(O)$NR'_2$. In some embodiments, $R^{1'}$ is —NR'C(O)R'. In some embodiments, $R^{1}$ is —NR'$CO_2R'$. In some embodiments, $R^{1'}$ is —$CO_2R'$. In some embodiments, $R^{1'}$ is —Br. In some embodiments, $R^{1'}$ is —Cl. In some embodiments, $R^{1'}$ is —F. In some embodiments, $R^{1'}$ is —$CH_3$. In some embodiments, $R^{1'}$ is —$CH_2CH_3$. In some embodiments, $R^{1'}$ is —$CH(CH_3)_2$. In some embodiments, $R^{1'}$ is —$CF_3$. In some embodiments, $R^{1'}$ is —$CF_2H$. In some embodiments, $R^{1'}$ is —$CFH_2$. In some embodiments, $R^{1'}$ is —$CF_2CH_3$. In some embodiments, $R^{1'}$ is —$CH_2CF_3$. In some embodiments, $R^{1'}$ is —C≡CCH. In some embodiments, $R^{1'}$ is vinyl. In some embodiments, $R^{1'}$ is —C≡$CCF_3$. In some embodiments, $R^{1'}$ is —$CO_2H$. In some embodiments, $R^{1'}$ is —OH. In some embodiments, $R^{1'}$ is —$OCH_3$. In some embodiments, $R^{1'}$ is —$OCH_2CH_3$. In some embodiments, $R^{1'}$ is —$OCH(CH_3)_2$. In some embodiments, $R^{1'}$ is —$OCF_3$. In some embodiments, $R^{1'}$ is —$NHCH_3$. In some embodiments, $R^{1'}$ is —$NHCD_3$. In some embodiments, $R^{1'}$ is —$N(CD_3)CO_2$tBu. In some embodiments, $R^{1'}$ is —$NHCH_2CH_3$. In some embodiments, $R^{1'}$ is —$NHCH_2(CH_3)_2$. In some embodiments, $R^{1'}$ is —$NHCH_2CF_3$. In some embodiments, $R^{1'}$ is —NHPh. In some embodiments, $R^{1'}$ is —NHAc. In some embodiments, $R^{1'}$ is —$N(CH_3)_2$. In some embodiments, $R^{1'}$ is

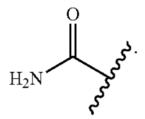

In some embodiments, $R^{1'}$ is

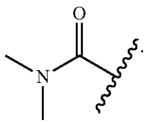 [SMILES: *C(=O)N(C)C]

In some embodiments, $R^{1'}$ is

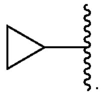

In some embodiments, $R^{1'}$ is

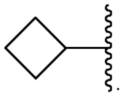 [SMILES: *C1CCC1]

In some embodiments, $R^{1'}$ is

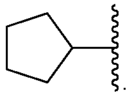

In some embodiments, $R^{1'}$ is

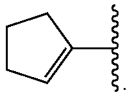

In some embodiments, $R^{1'}$ is

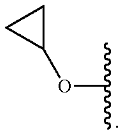

In some embodiments, $R^{1'}$ is

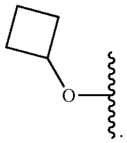

In some embodiments, $R^{1'}$ is

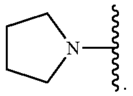

In some embodiments, $R^{1'}$ is

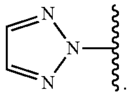

In some embodiments, $R^{1'}$ is

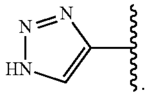

In some embodiments, $R^{1'}$ is

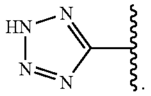

In some embodiments, $R^{1'}$ is

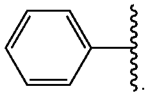 [SMILES: *c1ccccc1]

In some embodiments, $R^{1'}$ is

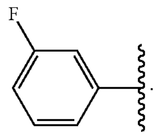

In some embodiments, $R^{1'}$ is

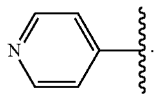

In some embodiments, $R^{1'}$ is

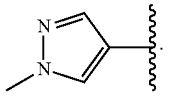 [SMILES: *c1cnn(C)c1]

In some embodiments, $R^{1'}$ is

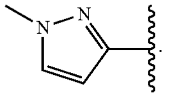 [SMILES: *c1ccn(C)n1]

In some embodiments, $R^{1'}$ is

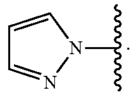

In some embodiments, $R^{1'}$ is

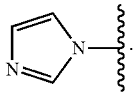

In some embodiments, $R^{1'}$ is

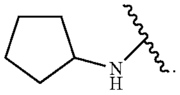 [SMILES: *NC1CCCC1]

In some embodiments, $R^{1'}$ is

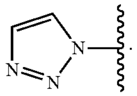

In some embodiments, $R^{1'}$ is

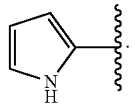

In some embodiments, $R^{1'}$ is

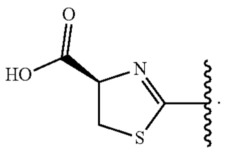 [SMILES: *C1=N[C@H](C(=O)O)CS1]

In some embodiments, $R^{1'}$ is

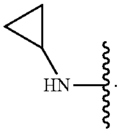

In some embodiments, $R^{1'}$ is

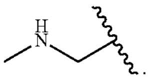

In some embodiments, $R^{1'}$ is

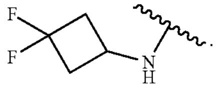

In some embodiments, $R^{1'}$ is

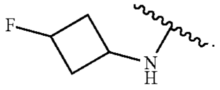 [SMILES: *NC1CC(F)C1]

In some embodiments, $R^{1'}$ is

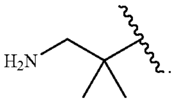

In some embodiments, $R^{1'}$ is selected from those depicted in Table 1, below.

As defined above and described herein, each R' is independently hydrogen or an optionally substituted group selected from $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur, or two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur.

In some embodiments, R' is hydrogen. In some embodiments, R' is an optionally substituted $C_{1-6}$ aliphatic. For instance, in some embodiments, R' is —$CF_3$, —$CF_2H$, or —$CFH_2$. In some embodiments, R' is an optionally substituted 3-8 membered saturated monocyclic carbocyclic ring. In some embodiments, R' is an optionally substituted 3-8 membered partially unsaturated monocyclic carbocyclic ring. In some embodiments, R' is an optionally substituted phenyl. In some embodiments, R' is an optionally substituted 8-10 membered bicyclic partially unsaturated carbocyclic ring. In some embodiments, R' is an optionally substituted 8-10 membered bicyclic aromatic carbocyclic ring. In some embodiments, R' is an optionally substituted 4-8 membered saturated monocyclic heterocyclic ring having 1-2 heteroatoms independently selected from nitrogen, oxygen, or sulfur. In some embodiments, R' is an optionally substituted 4-8 membered partially unsaturated monocyclic heterocyclic ring having 1-2 heteroatoms independently selected from nitrogen, oxygen, or sulfur. In some embodiments, R' is an optionally substituted 5-6 membered monocyclic heteroaromatic ring having 1-4 heteroatoms independently selected from nitrogen, oxygen, or sulfur. In some embodiments, R' is an optionally substituted 8-10 membered bicyclic partially unsaturated ring having 1-5 heteroatoms independently selected from nitrogen, oxygen, or sulfur. In some embodiments, R' is an optionally substituted 8-10 membered bicyclic heteroaromatic ring having 1-5 heteroatoms independently selected from nitrogen, oxygen, or sulfur. In some embodiments, two R' groups on the same carbon or nitrogen are optionally taken together with their intervening atoms to form an optionally substituted 4-10 membered saturated or partially unsaturated carbocyclic or heterocyclic ring having 1-3 heteroatoms, in addition to the carbon or nitrogen from which the two R' groups are attached, independently selected from nitrogen, oxygen, and sulfur.

In some embodiments, R' is selected from those depicted in Table 1, below.

As defined above and described herein, m' is an integer selected from 0 to 4.

In some embodiments, m' is 0. In some embodiments, m' is 1. In some embodiments, m' is 2. In some embodiments, m' is 3. In some embodiments, m' is 4.

In some embodiments, m is selected from those depicted in Table 1, below.

As defined above and described herein, each $R^A$ is independently an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or two $R^A$ groups on the same carbon or are optionally taken together with their intervening atoms to form an optionally substituted 3-6 membered saturated or partially unsaturated carbocyclic or heterocyclic ring having 1-3 heteroatoms, in addition to the carbon from which the two $R^A$ groups are attached, independently selected from nitrogen, oxygen, and sulfur.

In some embodiments, $R^A$ is an optionally substituted $C_{1-6}$ aliphatic. In some embodiments, $R^A$ is an optionally substituted 3-7 membered saturated monocyclic carbocyclic ring. In some embodiments, $R^A$ is an optionally substituted 3-7 membered partially unsaturated monocyclic carbocyclic ring. In some embodiments, $R^A$ is an optionally substituted phenyl. In some embodiments, $R^A$ is a 5-6 membered heteroaryl ring having 1-4 heteroatoms independently selected from nitrogen, oxygen, and sulfur. In some embodiments, two $R^A$ groups on the same carbon or are optionally taken together with their intervening atoms to form an optionally substituted 3-6 membered saturated or partially unsaturated carbocyclic or heterocyclic ring having 1-3 heteroatoms, in addition to the carbon from which the two $R^A$ groups are attached, independently selected from nitrogen, oxygen, and sulfur.

As defined above, $R^{2'}$ is hydrogen, $R^A$, —OR',

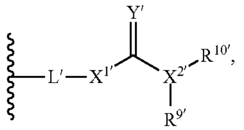

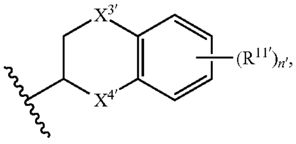

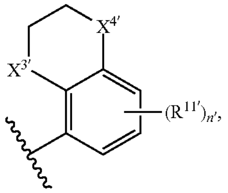

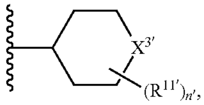

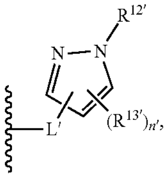

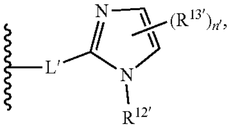

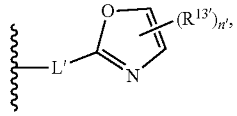

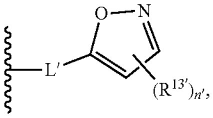

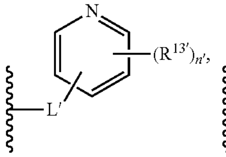

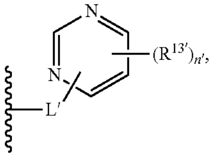

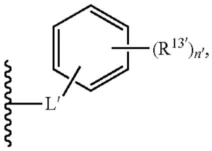

and

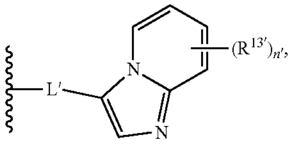

In some embodiments, $R^{2'}$ is hydrogen. In some embodiments, $R^{2'}$ is $R^A$. In some embodiments, $R^{2'}$ is —OR'. In some embodiments, $R^{2'}$ is

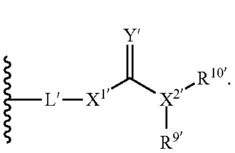

In some embodiments, $R^{2'}$ is

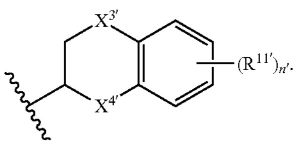

In some embodiments, $R^{2'}$ is

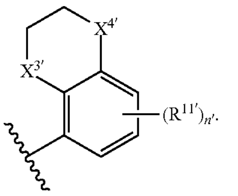

In some embodiments, $R^{2'}$ is

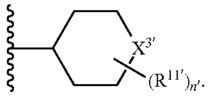

In some embodiments, $R^{2'}$ is

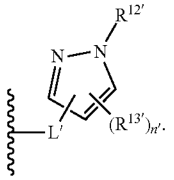

In some embodiments, $R^{2'}$ is

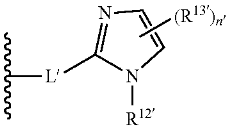

In some embodiments, $R^{2'}$ is

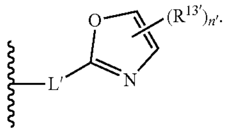

In some embodiments, $R^{2'}$ is

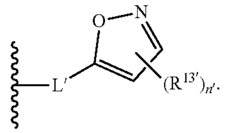

In some embodiments, $R^{2'}$ is

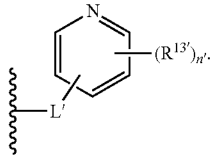

In some embodiments, $R^{2'}$ is

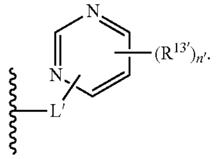

In some embodiments, $R^{2'}$ is

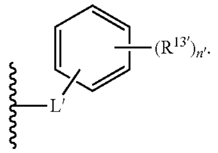

In some embodiments, $R^{2'}$ is

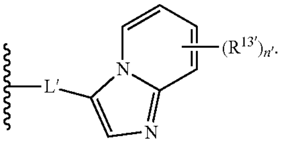

In some embodiments, $R^{2'}$ is $-CH_3$. In some embodiments, $R^{2'}$ is $-CD_3$. In some embodiments, $R^{2'}$ is $-C(CH_3)_3$. In some embodiments, $R^{2'}$ is $-C(CD_3)_3$. In some embodiments, $R^{2'}$ is $-C(CH_3)_2CH_2OR'$. In some embodiments, $R^{2'}$ is $-C(CH_3)_2CH_2OH$. In some embodiments, $R^{2'}$ is -iPr. In some embodiments, $R^{2'}$ is $-CH_2iPr$. In some embodiments, $R^{2'}$ is

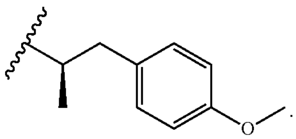 [SMILES: *[C@H](C)Cc1ccc(OC)cc1]

In some embodiments, $R^{2'}$ is

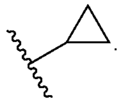 [SMILES: *C1CC1]

In some embodiments, $R^{2'}$ is

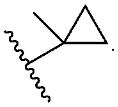

In some embodiments, $R^{2'}$ is

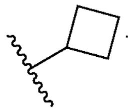

In some embodiments, $R^{2'}$ is

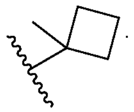

In some embodiments, $R^{2'}$ is

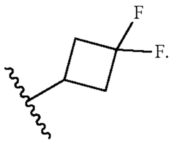 [SMILES: *C1CC(F)(F)C1]

In some embodiments, $R^{2'}$ is

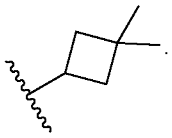 [SMILES: *C1CC(C)(C)C1]

In some embodiments $R^{2'}$ is selected from those depicted in Table 1, below.

As defined above and described herein, $R^{3a'}$ and $R^{3b'}$ are independently hydrogen, $R^A$, —OR', —C(O)R', —C(O)NR'$_2$, or —$CO_2$R', or $R^{3a'}$ and $R^{3b'}$ are optionally taken together with their intervening atoms to form an optionally substituted 4-10 membered saturated or partially unsaturated carbocyclic or heterocyclic ring having 1-3 heteroatoms, in addition to the nitrogen from which $R^{3a'}$ and $R^{3b'}$ are attached, independently selected from nitrogen, oxygen, and sulfur.

In some embodiments, $R^{3a'}$ is hydrogen. In some embodiments, $R^{3a'}$ is $R^A$. In some embodiments, $R^{3a'}$ is —OR'. In some embodiments, $R^{3a'}$ is —C(O)R'. In some embodiments, $R^{3a'}$ is —C(O)NR'$_2$. In some embodiments, $R^{3a'}$ is —$CO_2$R'. In some embodiments, $R^{3b'}$ is hydrogen. In some embodiments, $R^{3b'}$ is $R^A$. In some embodiments, $R^{3b'}$ is —OR'. In some embodiments, $R^{3b'}$ is —C(O)R'. In some embodiments, $R^{3b'}$ is —C(O)NR'$_2$. In some embodiments, $R^{3b'}$ is —$CO_2$R'. In some embodiments, $R^{3a'}$ and $R^{3b'}$ are optionally taken together with their intervening atoms to form an optionally substituted 4-10 membered saturated or partially unsaturated carbocyclic or heterocyclic ring having 1-3 heteroatoms, in addition to the nitrogen from which $R^{3a'}$ and $R^{3b'}$ are attached, independently selected from nitrogen, oxygen, and sulfur.

In some embodiments $R^{3a'}$ and $R^{3b'}$ are selected from those depicted in Table 1, below.

As defined above, $R^{4'}$, $R^{5'}$, and $R^{6'}$ are each independently hydrogen, halogen, $R^A$, —CN, —$NO_2$, —OR', —NR'$_2$,

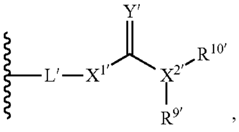
,
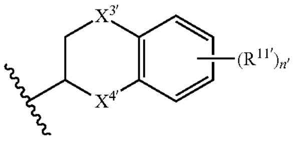
,
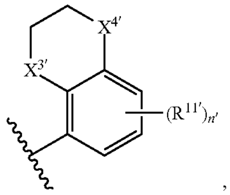
,
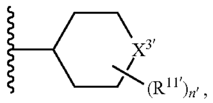
,
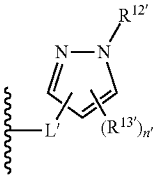
,
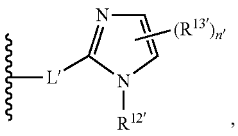
,
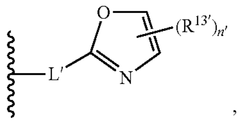
,
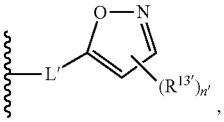
,
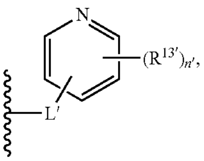
,
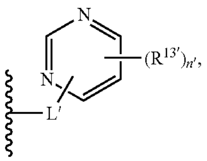
,
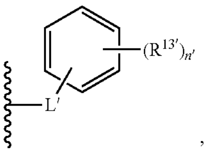
, and
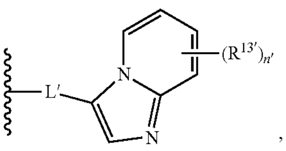
, or $R^{4'}$ and $R^{5'}$ are optionally taken together with the carbon to which they are attached to form an optionally substituted ring selected from a 3-7 membered saturated carbocyclic ring, a 5-6 membered monocyclic heteroaryl ring having 1-4 heteroatoms independently selected from nitrogen, oxygen, and sulfur, and a 3-7 membered saturated or a partially unsaturated monocyclic heterocyclic ring having 1-2 heteroatoms independently selected from nitrogen, oxygen, and sulfur.

In some embodiments, $R^{2'}$ is hydrogen. In some embodiments, $R^{2'}$ is $R^A$. In some embodiments, $R^{2'}$ is —OR'. In some embodiments, $R^{2'}$ is —NR'$_2$. In some embodiments, $R^{2'}$ is

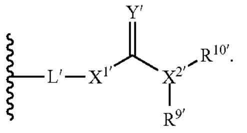

In some embodiments, $R^{2'}$ is

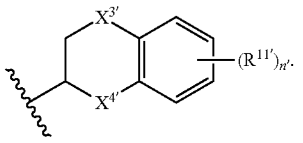

In some embodiments $R^{2'}$ is

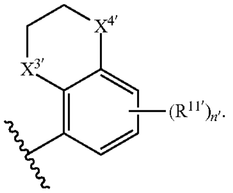

In some embodiments, $R^{2'}$ is

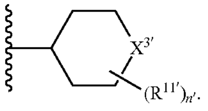

In some embodiments, $R^{2'}$ is

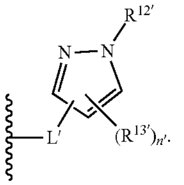

In some embodiments, $R^{2'}$ is

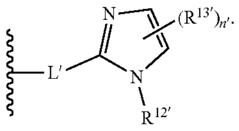

In some embodiments, $R^{2'}$ is

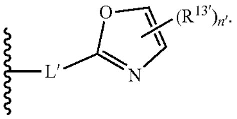

In some embodiments, $R^{2'}$ is

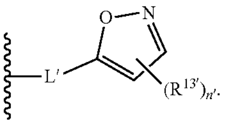

In some embodiments, $R^{2'}$ is

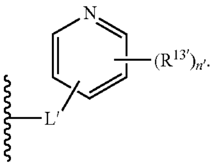

In some embodiments, $R^{2'}$ is

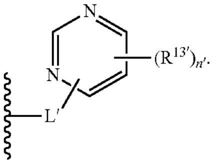

In some embodiments, $R^{2'}$ is

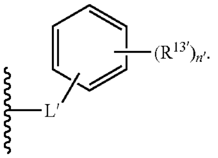

In some embodiments, $R^{2'}$ is

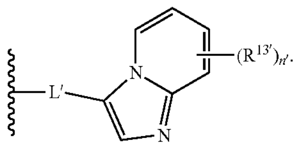

In some embodiments, $R^{2'}$ is —$CH_3$. In some embodiments, $R^{2'}$ is —$CD_3$. In some embodiments, $R^{2'}$ is —$C(CH_3)_3$. In some embodiments, $R^{2'}$ is —$C(CD_3)_3$. In some embodiments, $R^{2'}$ is

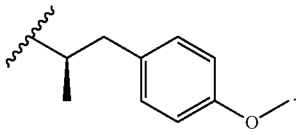 [SMILES: *[C@H](C)Cc1ccc(OC)cc1]

In some embodiments, $R^{4'}$ is hydrogen. In some embodiments, $R^{4'}$ is halogen. In some embodiments, $R^{4'}$ is $R^4$. In some embodiments, $R^{4'}$ is —CN. In some embodiments, $R^{4'}$ is —$NO_2$. In some embodiments, $R^{4'}$ is —OR'. In some embodiments, $R^{4'}$ is —$CH_2OR'$. In some embodiments, $R^{4'}$ is —$CH_2iPr$. In some embodiments, $R^{4'}$ is —$NR'_2$. In some embodiments, $R^{4'}$ is

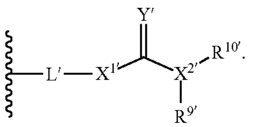

In some embodiments, $R^{4'}$ is

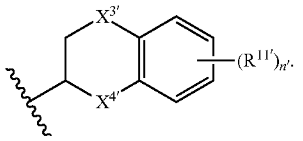

In some embodiments, $R^{4'}$ is

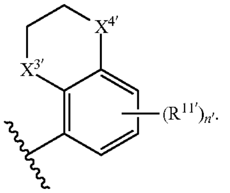

In some embodiments, $R^{4'}$ is

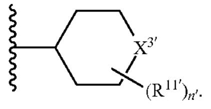

In some embodiments, $R^{4'}$ is

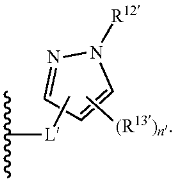

In some embodiments, $R^{4'}$ is

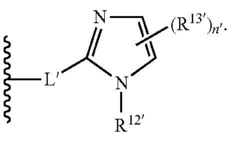

In some embodiments, $R^{4'}$ is

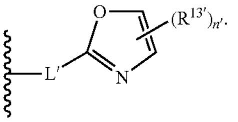

In some embodiments, $R_{4'}$ is

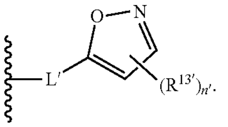

In some embodiments, $R^{4'}$ is

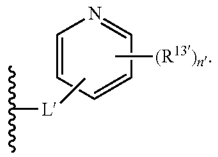

In some embodiments, $R^{4'}$ is

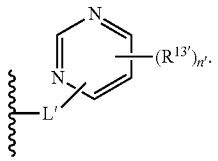

In some embodiments, $R^{4'}$ is

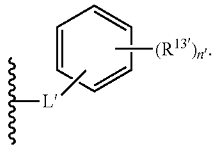

In some embodiments, $R^{4'}$ is

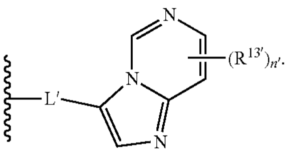

In some embodiments, $R^{4'}$ and $R^{5'}$ are optionally taken together with the carbon to which they are attached to form an optionally substituted 3-7 membered saturated carbocyclic ring. In some embodiments, $R^{4'}$ and $R^{5'}$ are optionally taken together with the carbon to which they are attached to form an optionally substituted 5-6 membered monocyclic heteroaryl ring having 1-4 heteroatoms independently selected from nitrogen, oxygen, and sulfur. In some embodiments, $R^{4'}$ and $R^{5'}$ are optionally taken together with the carbon to which they are attached to form an optionally substituted 3-7 membered saturated or a partially unsaturated monocyclic heterocyclic ring having 1-2 heteroatoms independently selected from nitrogen, oxygen, and sulfur. In some embodiments, $R^{4'}$ is —$CH_3$. In some embodiments, $R^{4'}$ is —$CD_3$. In some embodiments, $R^{4'}$ is

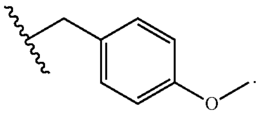 [SMILES: *Cc1ccc(OC)cc1]

In some embodiments, $R^{5'}$ is hydrogen. In some embodiments, $R^{5'}$ is halogen. In some embodiments, $R^{5'}$ is $R^{A}$. In some embodiments, $R^{5'}$ is —CN. In some embodiments, $R^{5'}$ is —$NO_2$. In some embodiments, $R_{5'}$ is —OR'. In some embodiments, $R^{5'}$ is —$NR'_2$. In some embodiments, $R^{5'}$ is

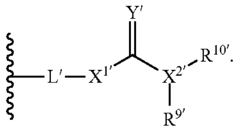

In some embodiments, $R^{5'}$ is

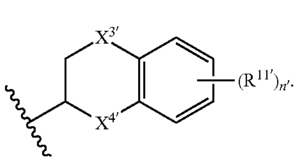

In some embodiments, $R^{5'}$ is

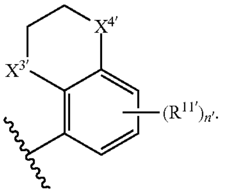

In some embodiments, $R^{5'}$ is

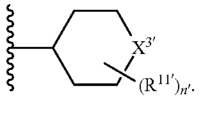

In some embodiments, $R^{5'}$ is

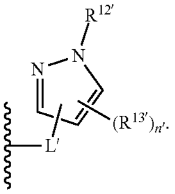

In some embodiments, $R_{5'}$ is

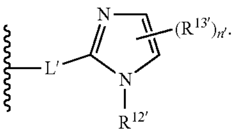

In some embodiments, $R^{5'}$ is

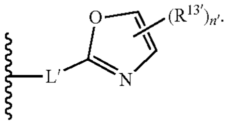

In some embodiments, $R^{5'}$ is

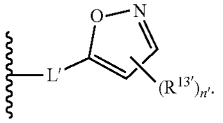

In some embodiments, $R^{5'}$ is

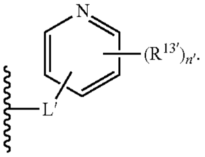

In some embodiments, $R^{5'}$ is

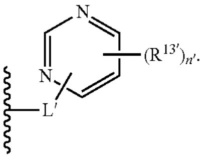

In some embodiments, $R_{5'}$ is

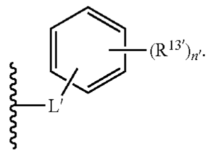

In some embodiments, R' is

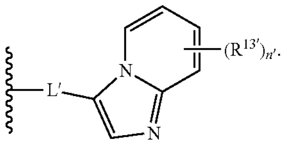

In some embodiments, $R^{5'}$ is —$CH_3$. In some embodiments, R 5' is —$CD_3$. In some embodiments, $R^{5'}$ is

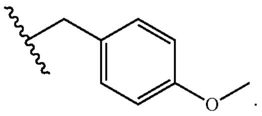 [SMILES: *Cc1ccc(OC)cc1]

In some embodiments, $R^{4'}$ and $R^{5'}$ are

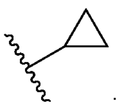

In some embodiments, $R^{4'}$ and $R^{5'}$ are

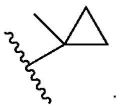

In some embodiments, $R^{4'}$ and $R^{5'}$ are

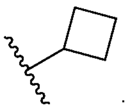 [SMILES: *C1CCC1]

In some embodiments, $R^{4'}$ and $R_{5'}$ are

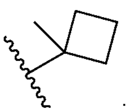 [SMILES: *C1(C)CCC1]

In some embodiments, $R^{4'}$ and $R^{5'}$ are

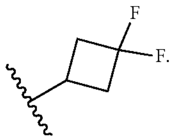 [SMILES: *C1CC(F)(F)C1]

In some embodiments, $R^{4'}$ and $R^{5'}$ are

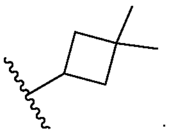 [SMILES: *C1CC(C)(C)C1]

In some embodiments, $R^{6'}$ is hydrogen. In some embodiments, $R^{6'}$ is halogen. In some embodiments, $R^{6'}$ is $R^4$. In some embodiments, $R^{6'}$ is —CN. In some embodiments, $R^{6'}$ is —$NO_2$. In some embodiments, $R^{6'}$ is —OR'. In some embodiments, $R^{6'}$ is —$NR'_2$. In some embodiments, $R^{6'}$ is

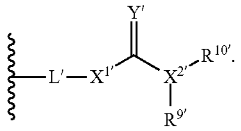

In some embodiments, $R_{6'}$ is

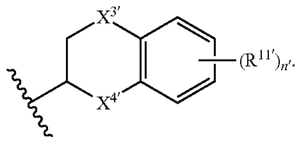

In some embodiments, $R^{6'}$ is

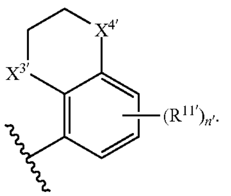

In some embodiments, $R^{6'}$ is

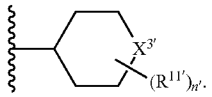

In some embodiments, $R^{6'}$ is

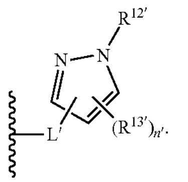

In some embodiments, $R_{6'}$ is

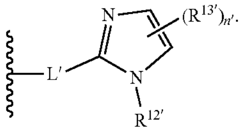

In some embodiments, $R_{6'}$ is

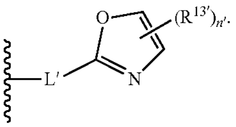

In some embodiments, $R^{6'}$ is

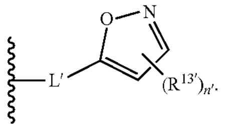

In some embodiments, $R^{6'}$ is

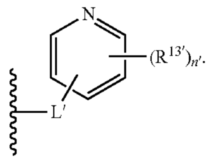

In some embodiments, $R^{6'}$ is

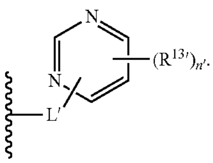

In some embodiments, $R^{6'}$ is

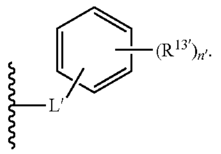

In some embodiments, $R^{6'}$ is

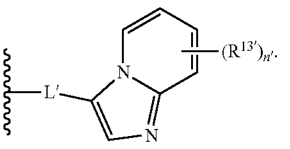

In some embodiments, $R^{6'}$ is —$CH_3$. In some embodiments, $R^{6'}$ is —$CD_3$. In some embodiments, $R^{6'}$ is

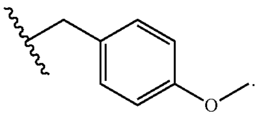 [SMILES: *Cc1ccc(OC)cc1]

In some embodiments, $R^{2'}$, $R^{4'}$, $R^{5'}$, and $R^{6'}$ are each selected from those depicted in Table 1, below.

As defined above and described herein, L' is an optionally substituted $C_{1-5}$ alkylene.

In some embodiments, L' is an optionally substituted $C_{1-5}$ alkylene. In some embodiments, L' is —$CH_2$—.

In some embodiments, L' is selected from those depicted in Table 1, below.

As defined above and described herein, $X^{1'}$, $X^{3'}$, and $X^{4'}$ are each independently a bivalent group selected from a covalent bond, —$CR'_2$—, —O—, and —NR'—.

In some embodiments, $X^{1'}$ is a covalent bond. In some embodiments, $X^{1'}$ is —$CR'_2$—. In some embodiments, $X^{1'}$ is —O—. In some embodiments, $X^{1'}$ is —NR'—. In some embodiments, $X^{3'}$ is a covalent bond. In some embodiments, $X^{3'}$ is —$CR'_2$—. In some embodiments, $X^{3'}$ is —O—. In some embodiments, $X^3$ is —NR'—. In some embodiments, $X^{4'}$ is a covalent bond. In some embodiments, $X^{4'}$ is —$CR'_2$—. In some embodiments, $X^{4'}$ is —O—. In some embodiments, $X^{4'}$ is —NR'—.

In some embodiments, $X^{1'}$, $X^{3'}$, and $X^{4'}$ are selected from those depicted in Table 1, below.

As defined above and described herein, $X^{2'}$ is a carbon atom or a nitrogen atom.

In some embodiments, $X^{2'}$ is a carbon atom. In some embodiments, $X^{2'}$ is nitrogen atom.

In some embodiments, $X^{2'}$ is selected from those depicted in Table 1, below.

As defined above and described herein, Y' is =O or =S.

In some embodiments, Y' is =O. In some embodiments, Y' is =S.

In some embodiments, Y' is selected from those depicted in Table 1, below.

As defined above and described herein, $R^{9'}$ and $R^{10'}$ are each independently hydrogen or an optionally substituted alkyl, or $R^{9'}$ and $R^{10'}$ are cyclically linked and together with $X^{2'}$, to form an optionally substituted ring selected from a 3-7 membered saturated carbocyclic ring, a 5-6 membered monocyclic heteroaryl ring having 1-4 heteroatoms independently selected from nitrogen, oxygen, and sulfur, a 3-7 membered saturated or partially unsaturated monocyclic heterocyclic ring having 1-2 heteroatoms independently selected from nitrogen, oxygen, and sulfur, and a 7-12 membered saturated or partially unsaturated bicyclic heterocyclic ring having 1-4 heteroatoms independently selected from nitrogen, oxygen, and sulfur.

In some embodiments, $R^{9'}$ is hydrogen. In some embodiments, $R^{9'}$ is an optionally substituted $C_{1-6}$ alkyl. In some embodiments, $R^{10'}$ is hydrogen. In some embodiments, $R^{10'}$ is an optionally substituted $C_{1-6}$ alkyl. In some embodiments, $R^{9'}$ and $R^{10'}$ are cyclically linked and together with $X^{2'}$ to form an optionally substituted 3-7 membered saturated carbocyclic ring. In some embodiments, $R^{9'}$ and $R^{10'}$ are cyclically linked and together with $X^{2'}$ to form an optionally substituted 5-6 membered monocyclic heteroaryl ring having 1-4 heteroatoms independently selected from nitrogen, oxygen, and sulfur. In some embodiments, $R^{9'}$ and $R^{10'}$ are cyclically linked and together with $X^{2'}$ to form an optionally substituted 3-7 membered saturated or partially unsaturated monocyclic heterocyclic ring having 1-2 heteroatoms independently selected from nitrogen, oxygen, and sulfur. In some embodiments, $R^{9'}$ and $R^{10'}$ are cyclically linked and together with $X^{2'}$ to form an optionally substituted 7-12 membered saturated or partially unsaturated bicyclic heterocyclic ring having 1-4 heteroatoms independently selected from nitrogen, oxygen, and sulfur.

In some embodiments, $R^{9'}$ and $R^{10'}$ are each selected from those depicted in Table 1, below.

As defined above and described herein, each $R^{11'}$ is independently $R^A$, halogen, —CN, —$NO_2$, —$NR'_2$, or —OR'.

In some embodiments, $R^{11'}$ is hydrogen. In some embodiments, $R^{11'}$ is halogen. In some embodiments, $R^{11'}$ is —CN. In some embodiments, $R^{11'}$ is —$NO_2$. some embodiments, $R^{11'}$ is —$NR'_2$. In some embodiments, $R^{11'}$ is —OR'.

In some embodiments, each $R^{11'}$ is independently selected from those depicted in Table 1, below.

As defined above, n' is an integer selected from 0 to 4.

In some embodiments, n' is 0. In some embodiments, n' is 1. In some embodiments, n' is 2. In some embodiments, n' is 3. In some embodiments, n' is 4.

As defined above and described herein, $R^{12'}$ is hydrogen, $R^A$, or —CN.

In some embodiments, $R^{12'}$ is hydrogen. In some embodiments, $R^{12'}$ is $R^A$. In some embodiments, $R^{12'}$ is —CN.

In some embodiments, $R^{12'}$ is selected from those depicted in Table 1, below.

As defined above and described herein, each $R^{13'}$ is independently hydrogen, halogen, $R^A$, —CN, —OR', —$NR'_2$.

In some embodiments, $R^{13'}$ is hydrogen. In some embodiments, $R^{13'}$ is halogen. In some embodiments, $R^{13'}$ is —CN. In some embodiments, $R^{13'}$ is —OR'. In some embodiments, $R^{13'}$ is —$NR'_2$.

In some embodiments, $R^{13'}$ is selected from those depicted in Table 1, below.

As defined above and described herein, $R^{7'}$ and $R^{8'}$ are each independently hydrogen or optionally substituted $C_{1-2}$ aliphatic.

In some embodiments, $R^{7'}$ is hydrogen. In some embodiment, $R^{7'}$ is an optionally substituted $C_1$ aliphatic. In some embodiment, $R^{7'}$ is methyl. In some embodiment, $R^{7'}$ is an optionally substituted $C_2$ aliphatic. In some embodiment, $R^{7'}$ is ethyl. In some embodiments, $R^{8'}$ is hydrogen. In some embodiment, $R^{1'}$ is an optionally substituted $C_1$ aliphatic. In some embodiment, $R^{8'}$ is methyl. In some embodiment, $R^{8'}$ is an optionally substituted $C_2$ aliphatic. In some embodiment, $R^{8'}$ is ethyl.

In some embodiments, $R^{7'}$ and $R^{8'}$ are selected from those depicted in Table 1, below.

In some embodiments, the present disclosure provides a compound of Formula (I'), wherein Ring D' is benzo, A' is a carbon atom, and $R^{10'}$ and $R^{11'}$ are hydrogen as shown, to provide a compound of Formula (I'-a):

Formula (I'-a)

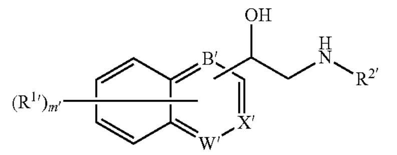

or a pharmaceutically acceptable salt thereof, wherein each of B', W', X', $R^{1'}$, $R^{2'}$, and m' is as defined above and described in embodiments herein, both singly and in combination.

In some embodiments, the present disclosure provides a compound of Formula (I'), wherein Ring D' is

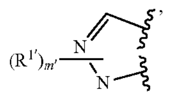

A' is a carbon atom, and $R^{10'}$ and $R^{11'}$ are hydrogen as shown, to provide a compound of Formula (I'-b):

Formula (I'-b)

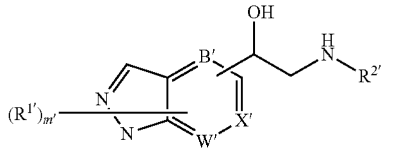

or a pharmaceutically acceptable salt thereof, wherein each of B', W', X', $R^{1'}$, $R^{2'}$, and m' is as defined above and described in embodiments herein, both singly and in combination.

In some embodiments, the present disclosure provides a compound of Formula (I'), wherein Ring D' is

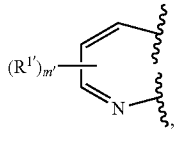

A' is a carbon atom, and $R^{10'}$ and $R^{11'}$ are hydrogen as shown, to provide a compound of Formula (I'-c):

Formula (I'-c)

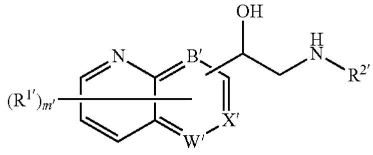

or a pharmaceutically acceptable salt thereof, wherein each of B', W', X', $R^{1'}$, $R^{2'}$, and m' is as defined above and described in embodiments herein, both singly and in combination.

In some embodiments, the present disclosure provides a compound of Formula (I'), wherein Ring D' is

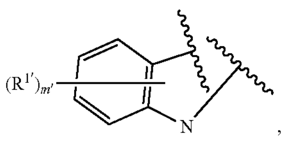

,

A' is a carbon atom, and $R^{10'}$ and $R^{11'}$ are hydrogen as shown, to provide a compound of Formula (I'-d):

Formula (I'-d)

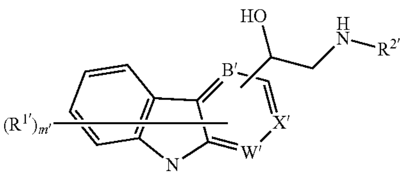

or a pharmaceutically acceptable salt thereof, wherein each of B', W', X', $R^{1'}$, $R^{2'}$, and m' is as defined above and described in embodiments herein, both singly and in combination.

In some embodiments, the present disclosure provides a compound of Formula (I'), wherein Ring D' is

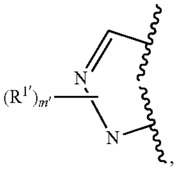

,

A' B', W', and X' are a carbon atoms, and $R^{10'}$ and $R^{1'}$ are hydrogen as shown, to provide a compound of Formula (I'-e):

Formula (I'-e)

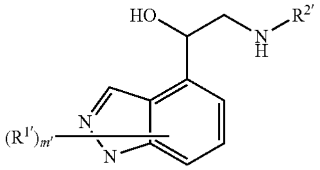

or a pharmaceutically acceptable salt thereof, wherein each of $R^{1'}$, $R^{2'}$, and m' is as defined above and described in embodiments herein, both singly and in combination.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those at risk or needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. In some embodiments, such amount should be sufficient to modulate an adrenergic receptor.

In some embodiments, an effective amount of an adrenergic receptor modulating compound is an amount that ranges from about 50 ng/ml to 50 pg/ml (e.g., from about 50 ng/ml to 40 pg/ml, from about 30 ng/ml to 20 pg/ml, from about 50 ng/ml to 10 pg/ml, from about 50 ng/ml to 1 µg/ml, from about 50 ng/ml to 800 ng/ml, from about 50 ng/ml to 700 ng/ml, from about 50 ng/ml to 600 ng/ml, from about 50 ng/ml to 500 ng/ml, from about 50 ng/ml to 400 ng/ml, from about 60 ng/ml to 400 ng/ml, from about 70 ng/ml to 300 ng/ml, from about 60 ng/ml to 100 ng/ml, from about 65 ng/ml to 85 ng/ml, from about 70 ng/ml to 90 ng/ml, from about 200 ng/ml to 900 ng/ml, from about 200 ng/ml to 800 ng/ml, from about 200 ng/ml to 700 ng/ml, from about 200 ng/ml to 600 ng/ml, from about 200 ng/ml to 500 ng/ml, from about 200 ng/ml to 400 ng/ml, or from about 200 ng/ml to about ng/ml).

In some embodiments, an effective amount of an adrenergic receptor modulating compound is an amount that ranges from about 10 pg to 100 mg, e.g., from about 10 pg to 50 pg, from about 50 pg to 150 pg, from about 150 pg to 250 pg, from about 250 pg to 500 pg, from about 500 pg to 750 pg, from about 750 pg to 1 ng, from about 1 ng to 10 ng, from about 10 ng to 50 ng, from about 50 ng to 150 ng, from about 150 ng to 250 ng, from about 250 ng to 500 ng, from about 500 ng to 750 ng, from about 750 ng to 1 mg, from about 1 pg to 10 pg, from about 10 pg to 50 pg, from about 50 pg to 150 pg, from about 150 pg to 250 pg, from about 250 pg to 500 pg, from about 500 pg to 750 pg, from about 750 pg to 1 mg, from about 1 mg to 50 mg, from about 1 mg to 100 mg, or from about 50 mg to 100 mg. The amount can be a single dose amount or can be a total daily amount. The total daily amount can range from about 10 pg to 100 mg, or can range from about 100 mg to 500 mg, or can range from about 500 mg to 1000 mg.

Also disclosed herein are pharmaceutical compositions including compounds as disclosed herein e.g., with the structures of Formula (I), Formula (I'), Formula (II), Formula (II'), Formula (III), Formula (IV) Formula (I), Formula (I'), Formula (II), Formula (II'), Formula (III), Formula (IV), Formula (VI'), and Formula (VII'). The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

In some embodiments, a compound as disclosed herein may be an adrenergic receptor modulating compound (e.g., an agonist, partial agonist or antagonist of an adrenergic receptor). The adrenergic receptor modulating compounds of the present disclosure can in some embodiments find use in modulating the activity of a target adrenergic receptor in vitro or in vivo. Aspects of the subject methods include contacting a sample with an effective amount of an adrenergic receptor modulating compound (e.g., as described herein) to determine whether the activity desired exists.

Adrenergic receptors (ADRs) are G-protein coupled receptors (GPCR) that are widely expressed throughout the body and play an important role in regulating multiple physiological processes including cognition, stress-related behavior, inflammation, and smooth muscle contraction/dilation, cardiac muscle contraction, airway reactivity and cognition. Adrenergic receptors mediate the central and peripheral effects of noradrenaline (NA) and adrenaline. Multiple subtypes of ADRs exist, including α-adrenergic receptors and β-adrenergic receptors. Each subtype is expressed in distinct patterns and involved in different physiological processes. Therefore, ligands that selectively target one subtype are valuable both as research tools to identify the roles of different ADR subtypes and as therapeutic agents for multiple diseases related to dysfunction of the NA and adrenaline systems.

β-adrenergic receptors further include three sub-types: β1-adrenergic receptor (β1-ADR), β2-adrenergic receptor (β2-ADR), and β3-adrenergic receptor (β3-ADR). Because these subtypes are expressed in distinct patterns and involved in different physiological processes, ligands that can selectively target one subtype have therapeutic potential for multiple diseases. However, discovery of subtype-selective ligands has been challenging due to a high level of sequence homology shared by these subtypes. A lot of existing agonists for β-adrenergic receptors also exhibit inferior blood-brain-barrier (BBB) penetration, which is required in an effort for drug discovery for central nervous system (CNS) indications.

As a class of G-protein coupled receptor, adrenergic receptors signal via G protein- and β-arrestin-dependent pathways. G protein- or β-arrestin signaling can mediate different physiological responses. Recently, it has become clear that agonists can show biased activation of signaling pathways. The ability of ligands to activate the receptor and produce responses in a pathway-dependent manner has been termed "signaling bias" or "functional selectivity". As G proteins and β-arrestins mediate distinct physiological processes, biased agonists can provide improved therapeutic selectivity with reduced adverse effects. Thus, the present disclosure is directed to β-adrenergic receptor subtype-selective agonists with improved blood-brain-barrier (BBB) penetration.

An adrenergic receptor modulating compound can be an agonist of the target adrenergic receptor. In some cases, an effective amount of an adrenergic receptor modulating compound is an amount sufficient to activate an activity related to the adrenergic receptor in a cell by 10% or more, such as 20% or more, 30% or more, 40% or more, 50% or more, 60% or more, 70% or more, 80% or more, 90% or more, 100% or more, 200% or even more relative to a control, e.g., a control cell exhibiting a known activity level of the receptor.

The adrenergic receptor modulating compound can be a partial agonist of the target adrenergic receptor. In some cases, an effective amount of an adrenergic receptor modulating compound is an amount sufficient to achieve partially agonism of the adrenergic receptor in a cell, e.g., where the subject compound achieves 10% activation or more of the receptor, such as 20% or more, 30% or more, 40% or more, 50% or more, 60% or more, 70% or more, 80% or more, or 90% or more, relative to a control, e.g., a receptor that is fully activated. Partial agonism may be assessed using any convenient methods, such as a cell based assay using a known full agonist as a 100% activation control, where the relative maximum activation of the receptor can be measured relative to the full agonist.

The adrenergic receptor modulating compound can be an antagonist of the target adrenergic receptor. In some cases, an effective amount of an adrenergic receptor modulating compound is an amount sufficient to inhibit or decrease the activity of the target adrenergic receptor in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

In some embodiments of the method, the target adrenergic receptor is a β1-adrenergic receptor. In some embodiments of the method, the target adrenergic receptor is a β2-adrenergic receptor. In some embodiments of the method, the target adrenergic receptor is a β3-adrenergic receptor. In some embodiments, the compound is an agonist for both β1-adrenergic receptor and β2-adrenergic receptor. In certain cases, the compound is selective for the β2-adrenergic receptor over a β1-adrenergic receptor.

The target adrenergic receptor may be one that is responsible for a mediating an intracellular signal or pathway in a cell. In some embodiments, the sample includes a cell and modulating the adrenergic receptor modulates a physiological process in the cell. Any convenient physiological processes can be targeted for modulation in a cell using the subject methods. In some embodiments, the physiological process is one that is implicated in cardiac function, in certain instances, the physiological process is one that is implicated in cognitive function. In certain instances, the physiological process is one that is implicated in an inflammatory pathway or condition. The subject methods can provide for mediation of the intracellular concentration of a signaling molecule in a cell, such as cAMP. The subject methods can provide for partial or full blockage of the target adrenergic receptor to result in modulation (e.g., activation) of cAMP in a sample. In some embodiments, the method does not modulate β-arrestin pathways of the cell. In some cases, the cells are inflammatory cells and the function of the cells is regulated. The subject methods can provide for inhibition of an inflammatory pathway in a cell. In some cases, TNF-alpha is inhibited in the cell, e.g., the concentration or production of TNF-alpha is reduced by practicing the subject method. In certain embodiments of the method, the cell is a neuron. In some embodiments, modulating the adrenergic receptor enhances neurogenesis.

The compounds of this disclosure may be employed in a conventional manner for controlling, preventing, treating a disease described herein, including, but not limited to, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis, cerebral autosomal dominant arteriopathy with subcortical infarcts (CADASIL) and diabetic retinopathy. Such methods of treatment, their dosage levels and requirements may be selected by those of ordinary skill in the art from available methods and techniques.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

In some embodiments, the subject method includes administering a therapeutically effective amount of one or more additional active agents. By combination therapy is meant that an adrenergic receptor modulating compound can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition.

The subject compounds can be administered in combination with other therapeutic agents in a variety of therapeutic applications. Therapeutic applications of interest for combination therapy include those applications in which activity of a target adrenergic receptor is the cause or a compounding factor in disease progression. As such, the subject compounds find use in combination therapies in which the inhibition of a target adrenergic receptor in the subject is desired. Examples of disease conditions which may be treated by a combination therapy including a subject compound include, but are not limited to, cardiac conditions or diseases, neurodegenerative or neurodevelopmental disease, respiratory disorders, asthma, memory impairment, depression, inflammatory diseases, stroke, ischemic brain or tissue injury and cancer. Agents of interest which can be used in jointly with the subject adrenergic receptor modulating compounds include, but are not limited to, antidepressants, antipsychotics, beta-blockers, vasoconstrictors, antihypotensives, decongestants, chemotherapeutic agents, agents used in Alzheimer's disease, and anti-inflammatory agents.

The subject adrenergic receptor modulating compounds can be used jointly with any agent useful in the treatment of a cardiac condition, such as cardiogenic shock, hypertension, congestive heart failure, coronary heart disease, arrhythmias, myocardial infarction or ischemic heart diseases. Agents of interest which can be used in jointly with the subject adrenergic receptor modulating compounds include, but are not limited to, denopamine, dobutamine, xamoterol, acebutolol, atenolol, betaxolol, bisoprolol, pindolol, esmolol, metoprolol, nebivolol, vortioxetine, Carvedilol, Labetalol, Phentolamine, Prazosin, Cirazoline, Methoxamine, Synephrine, Etilefrine, Metaraminol, Midodrine, and cumarin.

The subject adrenergic receptor modulating compounds can be used jointly with any agent useful in the treatment of a neurodegenerative or neurodevelopmental disease, such as such as Alzheimer's Disease, memory impairment, cognitive impairment, depression, stroke and ischemic brain or tissue injury, Down's syndrome or Autism. Agents of interest which can be used in jointly with the subject adrenergic receptor modulating compounds include, but are not limited to, acepromazine. In some embodiments, the subject adrenergic receptor modulating compounds can be used in the treatment of a disease, such as a neurodegenerative or neurodevelopmental disease, in combination with a cholinesterase inhibitor or a NMDA receptor modulators. Agents of interest include, but are not limited to, Donepezil, Aricept, Galantamine, Razadyne, Memantine, Namenda, Rivastigmine, Exelon, Tacrine and Cognex. Other agents of interest which can be used in jointly with the subject adrenergic receptor modulating compounds include, but are not limited to, 4-NEMD, 7-Me-marsanidine, Agmatine, Apraclonidine, Brimonidine, Cannabigerol, Clonidine, Detomidine, Dexmedetomidine, Fadolmidine, Guanabenz, Guanfacine, Lofexidine, Marsanidine, Medetomidine, Methamphetamine, Mivazerol, Rilmenidine, Romifidine, Talipexole, Tiamenidine, Tizanidine, Tolonidine, Xylazine, Xylometazoline, Aripiprazole, Asenapine, Atipamezole, Cirazoline, Clozapine, Efaroxan, Idazoxan, Lurasidone, Melperone, Mianserin, Mirtazapine, Napitane, Olanzapine, Paliperidone, Phenoxybenzamine, Phentolamine, Piribedil, Rauwolscine, Risperidone, Rotigotine, Quetiapine, Norquetiapine, Setiptiline, Tolazoline, Yohimbine, Ziprasidone and Zotepine. Other agents of interest which can be used in jointly with the subject adrenergic receptor modulating compounds include, but are not limited to, bitolterol, fenoterol, hexoprenaline, isoprenaline or isoproterenol, levosalbutamol or levalbuterol, orciprenaline or metaproterenol, pirbuterol, procaterol, salbutamol or albuterol, terbutaline, bambuterol, clenbuterol, formoterol, salmeterol, carmoterol, indacaterol, milveterol, olodaterol, vilanterol, fenoterol, hexoprenaline, isoxsuprine, ritodrine, salbutamol or albuterol, terbutaline, zilpaterol, ICI-118,551 and butoxamine.

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to stroke, ischemia, Alzheimer's, ankylosing spondylitis, arthritis, osteoarthritis, rheumatoid arthritis, psoriatic arthritis, asthma atherosclerosis, Crohn's disease, colitis, dermatitis diverticulitis, fibromyalgia, hepatitis, irritable bowel syndrome, systemic lupus erythematous, nephritis, ulcerative colitis and Parkinson's disease. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

Also provided are kits that include the disclosed adrenergic receptor modulating compounds. Systems of the present disclosure include collections of active agents brought together, e.g., by a health care practitioner, for administration to a subject, such as a patient. Such systems may include an adrenergic receptor modulating compound and one or more additional active agents disclosed herein. Kits that include adrenergic receptor modulating compounds which are provided that may include one or more dosages of an adrenergic receptor modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the as disclosed herein, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Table 1 below illustrates exemplary compounds of the instant disclosure.

TABLE 1

The compounds in the instant disclosure.

| Compound No. | Chemical Structure | MS (M + H) |
|---|---|---|
| 02-1 | 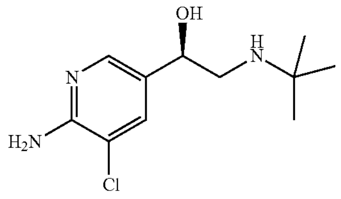 [SMILES: CC(C)(C)NC[C@H](O)c1cnc(N)c(Cl)c1] | 244.2 |
| 02-2 | 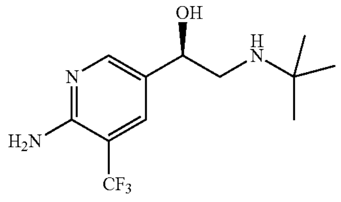 [SMILES: CC(C)(C)NC[C@H](O)c1cnc(N)c(C(F)(F)F)c1] | 278.2 |

TABLE 1-continued
The compounds in the instant disclosure.
| Compound No. | Chemical Structure | MS (M + H) |
| --- | --- | --- |
| 02-3 | 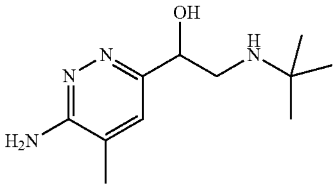 [SMILES: Cc1cc(C(O)CNC(C)(C)C)nnc1N] | 225.2 |
| 02-4 | 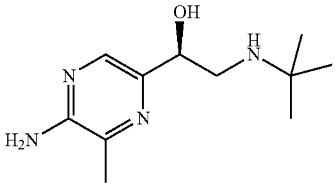 [SMILES: Cc1nc([C@@H](O)CNC(C)(C)C)cnc1N] | 225.2 |
| 02-5 | 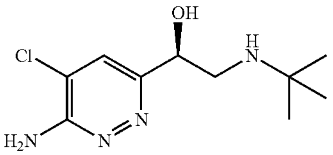 [SMILES: CC(C)(C)NC[C@H](O)c1cc(Cl)c(N)nn1] | |
| 02-6 | 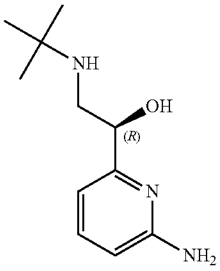 | 210.1 |
| 02-7 | 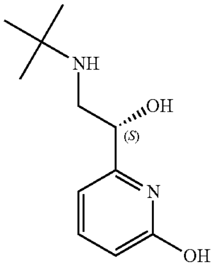 | 211.2 |
| 02-8 | 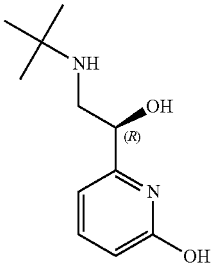 | 211.2 |

TABLE 1-continued
| The compounds in the instant disclosure. | | |
|---|---|---|
| Compound No. | Chemical Structure | MS (M + H) |
| 02-9 | 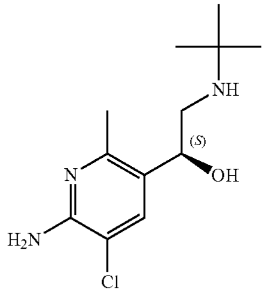 | 258.8 |
| 02-10 | 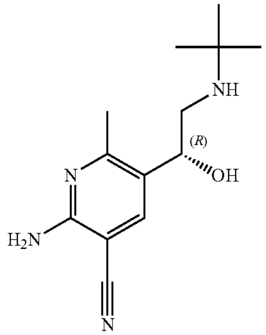 | 249.3 |
| 02-11 | 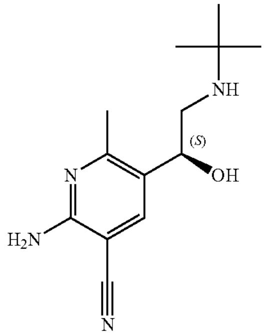 | 249.3 |
| 02-12 | 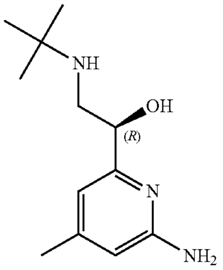 | 224.3 |
| 02-13 | 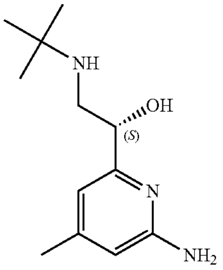 | 224.3 |

TABLE 1-continued
The compounds in the instant disclosure.
| Compound No. | Chemical Structure | MS (M + H) |
|---|---|---|
| 02-14 | 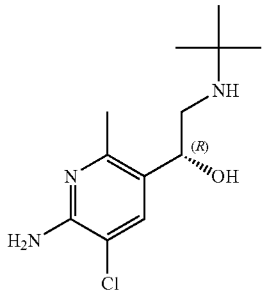 | 258.8 |
| 02-15 | 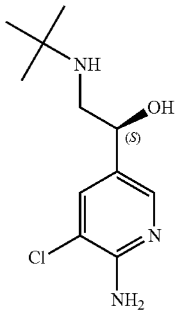 | 244.3 |
| 02-16 | 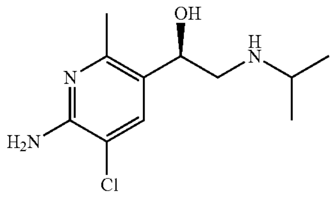 [SMILES: Cc1nc(N)c(Cl)cc1[C@@H](O)CNC(C)C] | 244.1 |
| 02-17 | 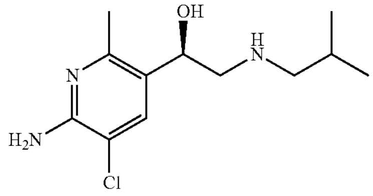 [SMILES: Cc1nc(N)c(Cl)cc1[C@@H](O)CNCC(C)C] | |
| 02-18 | 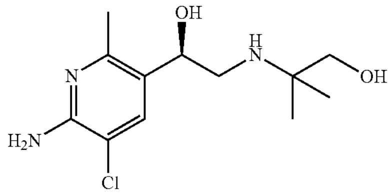 [SMILES: Cc1nc(N)c(Cl)cc1[C@@H](O)CNC(C)(C)CO] | 274.1 |
| 02-19 | 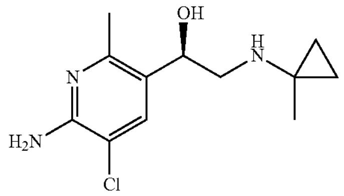 [SMILES: Cc1nc(N)c(Cl)cc1[C@@H](O)CNC1(C)CC1] | |

TABLE 1-continued
| The compounds in the instant disclosure. | | |
|---|---|---|
| Compound No. | Chemical Structure | MS (M + H) |
| 02-20 | 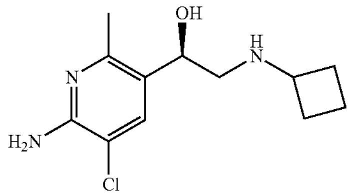 [SMILES: Cc1nc(N)c(Cl)cc1[C@@H](O)CNC1CCC1] | 256.1 |
| 02-21 | 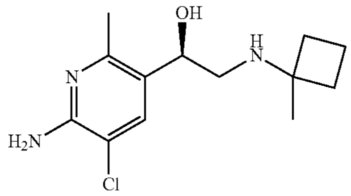 [SMILES: Cc1nc(N)c(Cl)cc1[C@@H](O)CNC1(C)CCC1] | |
| 02-22 | 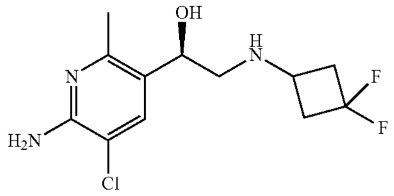 [SMILES: Cc1nc(N)c(Cl)cc1[C@@H](O)CNC1CC(F)(F)C1] | |
| 02-23 | 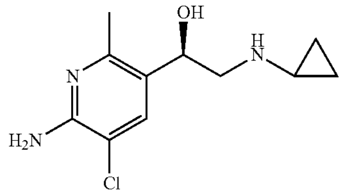 [SMILES: Cc1nc(N)c(Cl)cc1[C@@H](O)CNC1CC1] | |
| 02-24 | 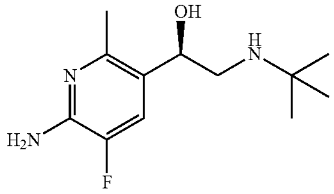 [SMILES: Cc1nc(N)c(F)cc1[C@@H](O)CNC(C)(C)C] | |
| 02-25 | 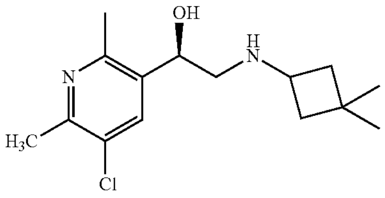 | |
| 04-1 | 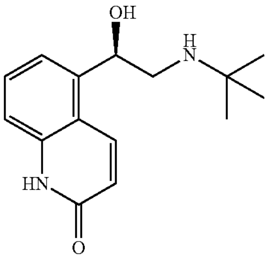 [SMILES: CC(C)(C)NC[C@H](O)c1cccc2[nH]c(=O)ccc12] | 261.22 |

TABLE 1-continued
The compounds in the instant disclosure.
| Compound No. | Chemical Structure | MS (M + H) |
| --- | --- | --- |
| 04-2 | 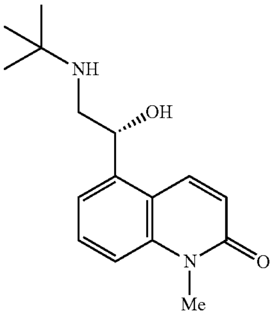 [SMILES: Cn1c(=O)ccc2c([C@@H](O)CNC(C)(C)C)cccc21] | 275.26 |
| 04-3 | 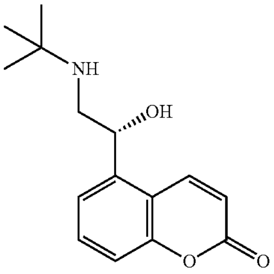 [SMILES: CC(C)(C)NC[C@H](O)c1cccc2oc(=O)ccc12] | 262.24 |
| 04-4 | 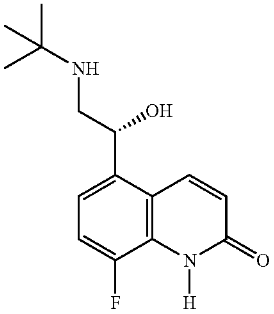 [SMILES: CC(C)(C)NC[C@H](O)c1ccc(F)c2[nH]c(=O)ccc12] | 279.25 |
| 04-5 | 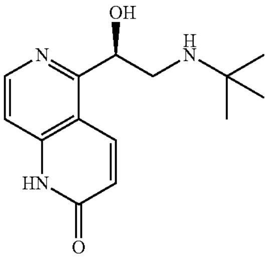 [SMILES: CC(C)(C)NC[C@H](O)c1nccc2[nH]c(=O)ccc12] | 262.22 |
| 04-6 | 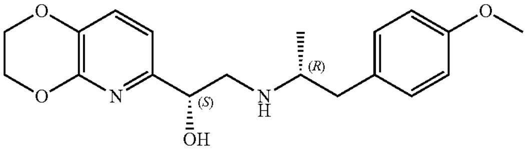 | 345.4 |
| 04-7 | 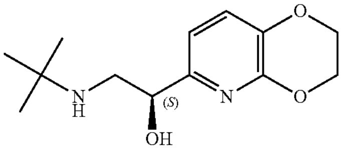 | 253.2 |

TABLE 1-continued
The compounds in the instant disclosure.
| Compound No. | Chemical Structure | MS (M + H) |
|---|---|---|
| 04-8 | 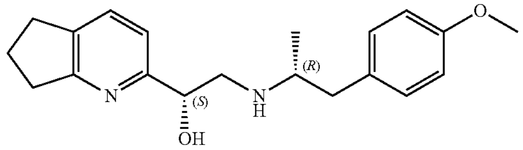 | 327.4 |
| 04-9 | 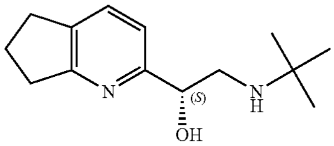 | 235.2 |
| 04-10 | 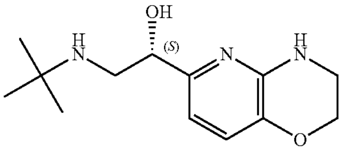 | 252.3 |
| 04-11 | 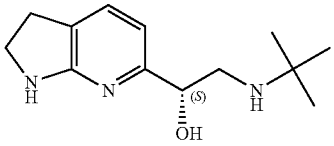 | 236.3 |
| 04-12 | 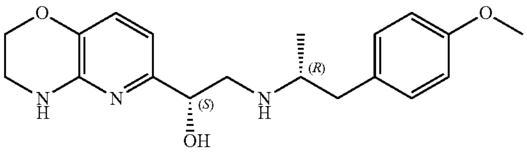 | 344.4 |
| 04-13 | 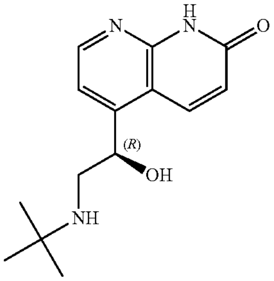 | 262.2 |
| 04-14 | 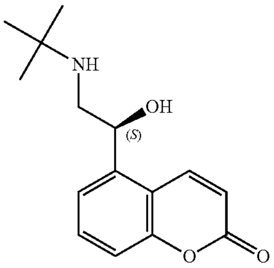 | 262.28 |

TABLE 1-continued
| The compounds in the instant disclosure. | | |
|---|---|---|
| Compound No. | Chemical Structure | MS (M + H) |
| 04-15 | 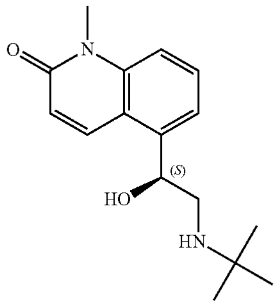 | 275.3 |
| 04-16 | 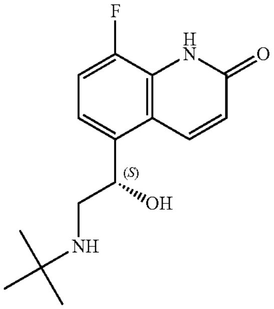 | 279.25 |
| 04-17 | 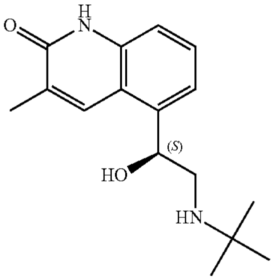 | 275.26 |
| 04-18 | 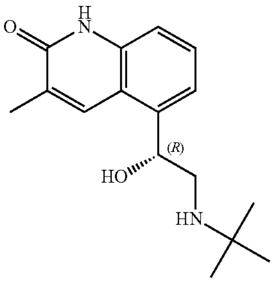 | 275.26 |
| 04-19 | 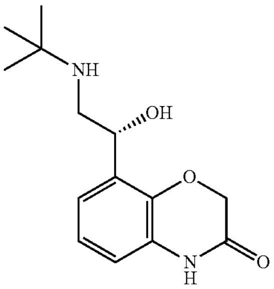 [SMILES: CC(C)(C)NC[C@H](O)c1cccc2c1OCC(=O)N2] | 265.3 |

TABLE 1-continued
| The compounds in the instant disclosure. | | |
|---|---|---|
| Compound No. | Chemical Structure | MS (M + H) |
| 04-20 | 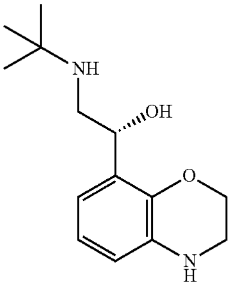 [SMILES: CC(C)(C)NC[C@H](O)c1cccc2c1OCCN2] | |
| 04-21 | 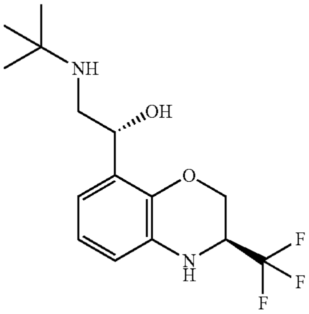 [SMILES: CC(C)(C)NC[C@H](O)c1cccc2c1OC[C@@H](C(F)(F)F)N2] | |
| 04-22 | 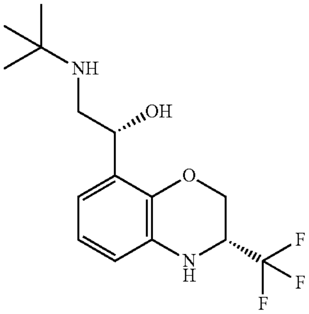 [SMILES: CC(C)(C)NC[C@H](O)c1cccc2c1OC[C@H](C(F)(F)F)N2] | |
| 04-23 | 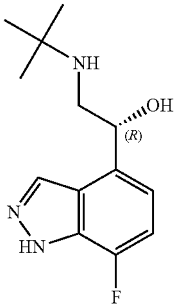 | 252.35 |
| 04-24 | 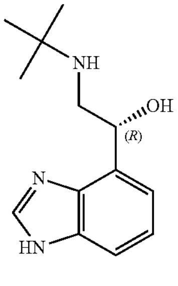 | 234.25 |

TABLE 1-continued
| The compounds in the instant disclosure. | | |
|---|---|---|
| Compound No. | Chemical Structure | MS (M + H) |
| 04-25 | 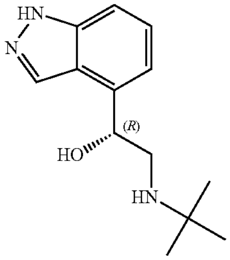 | 234.35 |
| 04-26 | 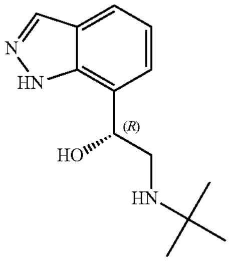 | 234.25 |
| 04-27 | 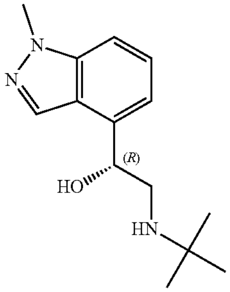 | 248.3 |
| 04-28 | 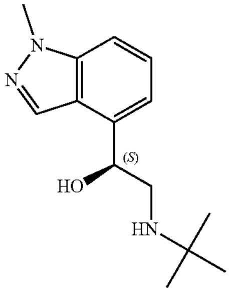 | 248.3 |
| 04-29 | 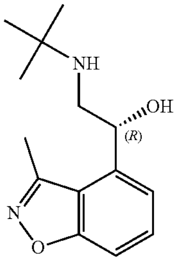 | 249.21 |

TABLE 1-continued
The compounds in the instant disclosure.
| Compound No. | Chemical Structure | MS (M + H) |
| --- | --- | --- |
| 04-30 | 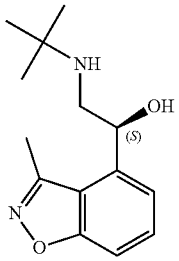 | 249.21 |
| 04-31 | 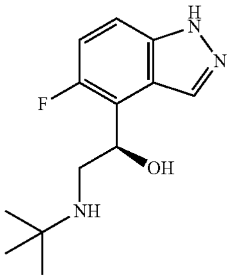 [SMILES: CC(C)(C)NC[C@H](O)c1c(F)ccc2[nH]ncc12] | 252.35 |
| 04-32 | 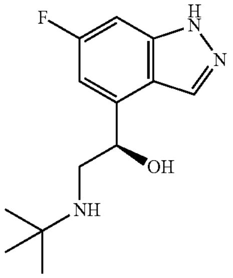 [SMILES: CC(C)(C)NC[C@H](O)c1cc(F)cc2[nH]ncc12] | 252.33 |
| 04-33 | 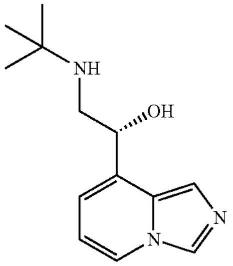 [SMILES: CC(C)(C)NC[C@H](O)c1cccn2cncc12] | |
| 04-34 | 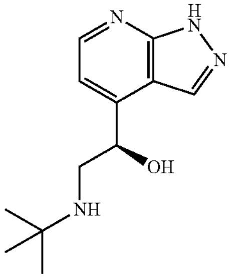 [SMILES: CC(C)(C)NC[C@H](O)c1ccnc2[nH]ncc12] | 235.3 |

TABLE 1-continued
The compounds in the instant disclosure.
| Compound No. | Chemical Structure | MS (M + H) |
|---|---|---|
| 04-35 | 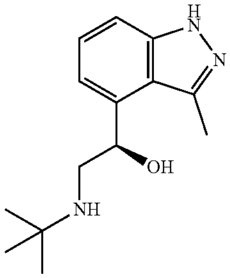 [SMILES: Cc1n[nH]c2cccc([C@@H](O)CNC(C)(C)C)c12] | 248.3 |
| 04-36 | 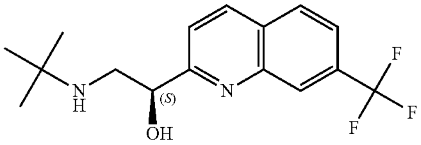 | 313.23 |
| 04-37 | 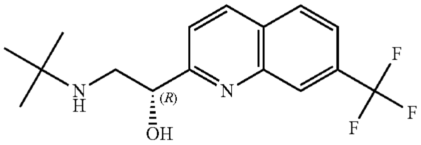 | 313.18 |
| 04-38 | 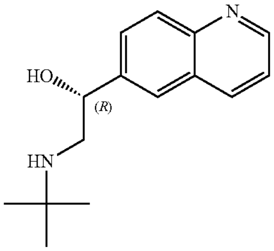 | 245.2 |
| 04-39 | 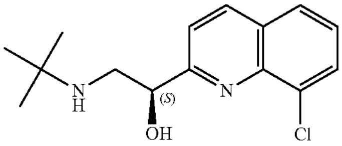 | 279 |
| 04-40 | 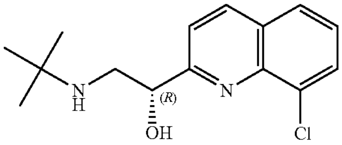 | 279 |
| 04-41 | 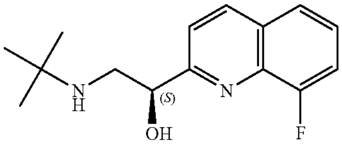 | 263.29 |
| 04-42 | 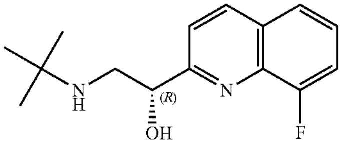 | 263.33 |

TABLE 1-continued
The compounds in the instant disclosure.
| Compound No. | Chemical Structure | MS (M + H) |
| --- | --- | --- |
| 04-43 | 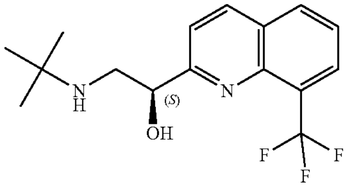 | 313.26 |
| 04-44 | 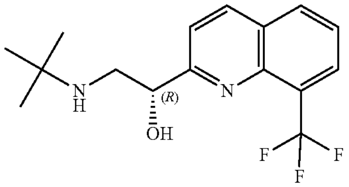 | 313.26 |
| 04-45 | 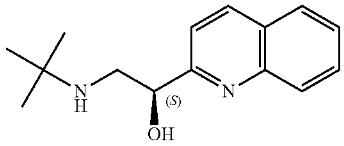 | 245.1 |
| 04-46 | 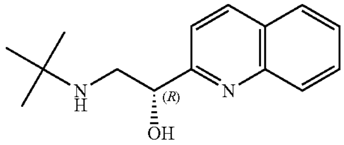 | 245.1 |
| 04-47 | 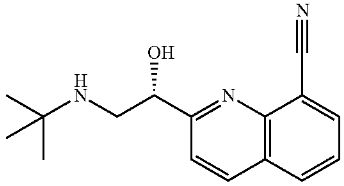 [SMILES: CC(C)(C)NC[C@H](O)c1ccc2cccc(C#N)c2n1] | 270.3 |
| 04-48 | 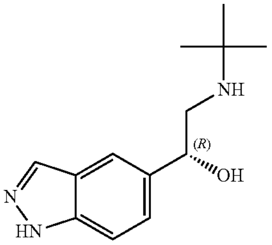 | 234.2 |
| 04-49 | 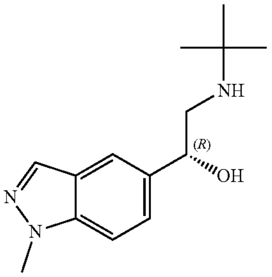 | 248.31 |

TABLE 1-continued
The compounds in the instant disclosure.
| Compound No. | Chemical Structure | MS (M + H) |
| --- | --- | --- |
| 04-50 | 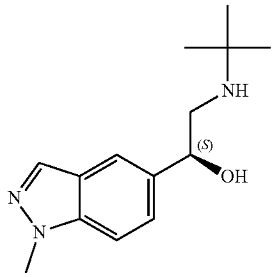 | 248.31 |
| 04-51 | 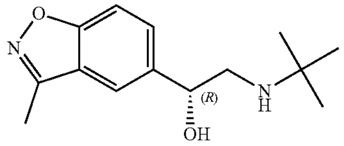 | 249.3 |
| 04-52 | 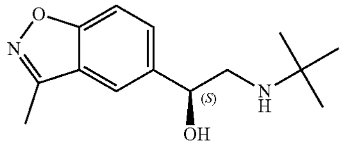 | 249.3 |
| 04-53 | 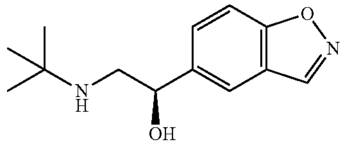 [SMILES: CC(C)(C)NC[C@H](O)c1ccc2oncc2c1] | |
| 04-54 | 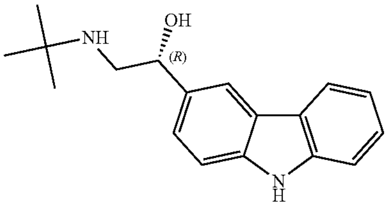 | 283.1 |
| 04-55 | 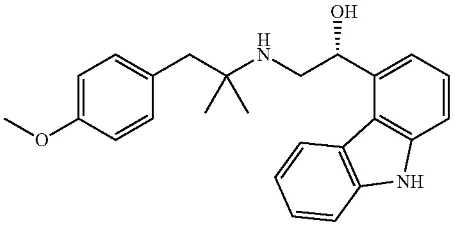 [SMILES: COc1ccc(CC(C)(C)NC[C@H](O)c2cccc3[nH]c4ccccc4c23)cc1] | 389.35 |
| 04-56 | 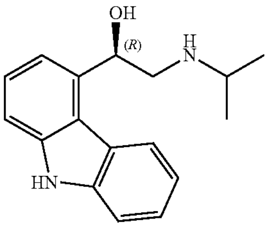 | 269.1 |

TABLE 1-continued
The compounds in the instant disclosure.
| Compound No. | Chemical Structure | MS (M + H) |
|---|---|---|
| 04-57 | 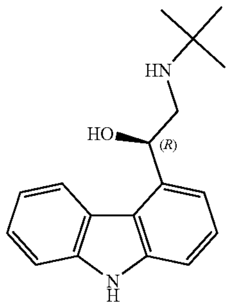 | 283.1 |
| 04-58 | 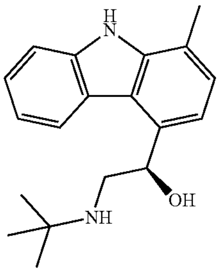 [SMILES: Cc1ccc([C@@H](O)CNC(C)(C)C)c2c1[nH]c1ccccc12] | |
| 04-59 | 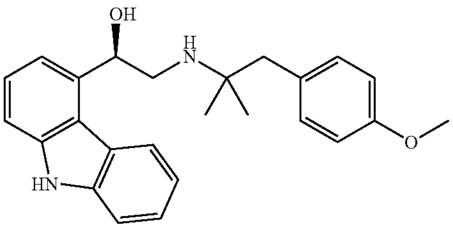 [SMILES: COc1ccc(CC(C)(C)NC[C@H](O)c2cccc3[nH]c4ccccc4c23)cc1] | |
| 04-60 | 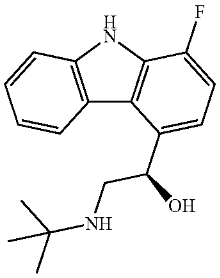 [SMILES: CC(C)(C)NC[C@H](O)c1ccc(F)c2[nH]c3ccccc3c12] | 301.35 |
| 04-61 | 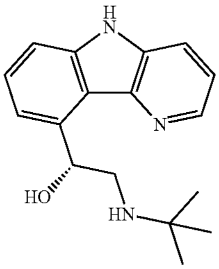 [SMILES: CC(C)(C)NC[C@H](O)c1cccc2[nH]c3cccnc3c12] | 284.4 |

TABLE 1-continued
The compounds in the instant disclosure.
| Compound No. | Chemical Structure | MS (M + H) |
|---|---|---|
| 04-62 | 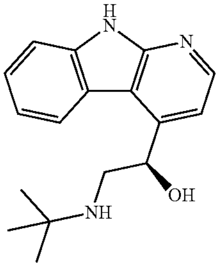 [SMILES: CC(C)(C)NC[C@H](O)c1ccnc2[nH]c3ccccc3c12] | |
| 04-63 | 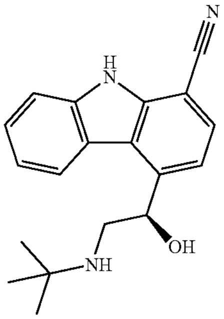 [SMILES: CC(C)(C)NC[C@H](O)c1ccc(C#N)c2[nH]c3ccccc3c12] | |
| 04-64 | 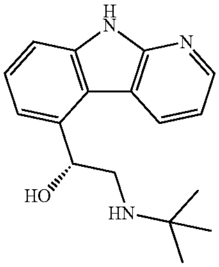 [SMILES: CC(C)(C)NC[C@H](O)c1cccc2[nH]c3ncccc3c12] | 284.4 |
| 04-65 | 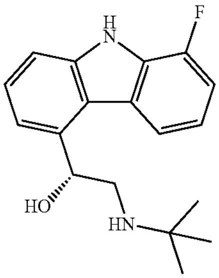 [SMILES: CC(C)(C)NC[C@H](O)c1cccc2[nH]c3c(F)cccc3c12] | |
| 04-66 | 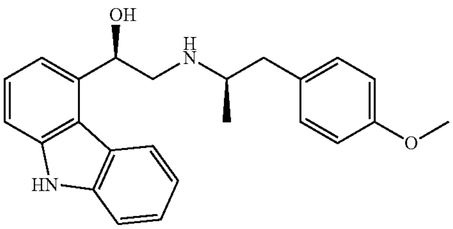 [SMILES: COc1ccc(C[C@@H](C)NC[C@H](O)c2cccc3[nH]c4ccccc4c23)cc1] | 375.5 |

TABLE 1-continued
| Compound No. | The compounds in the instant disclosure. Chemical Structure | MS (M + H) |
|---|---|---|
| 04-67 | 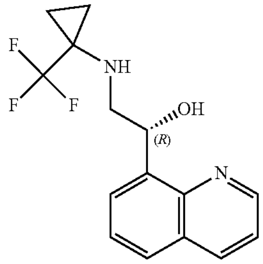 | 297.24 |
| 04-68 | 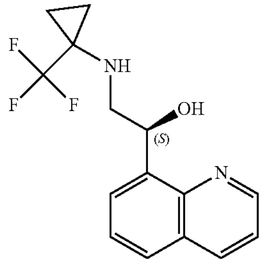 | 297.24 |
| 04-69 | 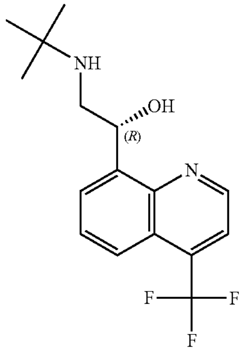 | 313.27 |
| 04-70 | 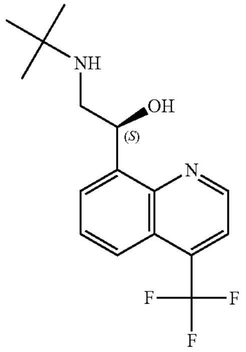 | 313.28 |
| 04-71 | 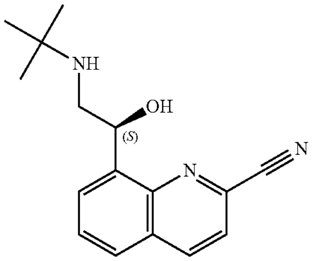 | 270.31 |

TABLE 1-continued
The compounds in the instant disclosure.
| Compound No. | Chemical Structure | MS (M + H) |
|---|---|---|
| 04-72 | 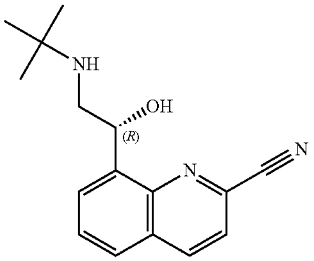 | 270.27 |
| 04-73 | 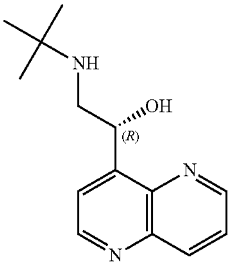 | 246.2 |
| 04-74 | 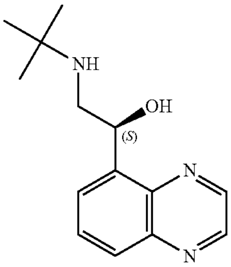 | 246.27 |
| 04-75 | 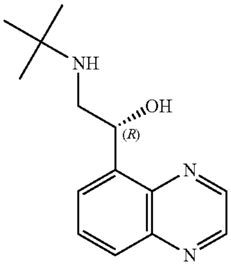 | 246.27 |
| 04-76 | 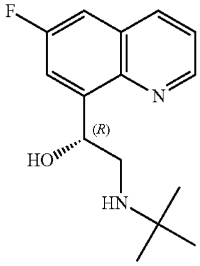 | 263.2 |

TABLE 1-continued
| The compounds in the instant disclosure. | | |
|---|---|---|
| Compound No. | Chemical Structure | MS (M + H) |
| 04-77 | 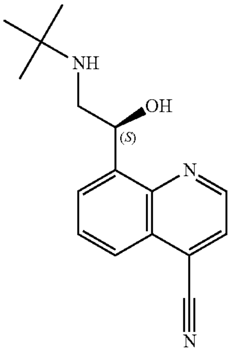 | 270.27 |
| 04-78 | 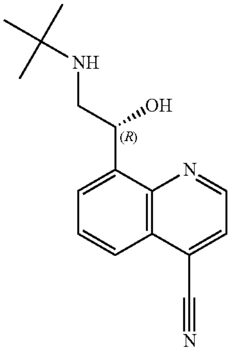 | 270.27 |
| 04-79 | 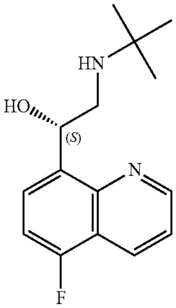 | 263.1 |
| 04-80 | 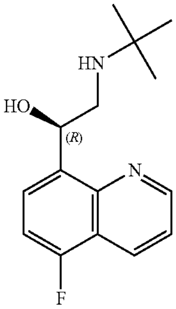 | 263.1 |

TABLE 1-continued
| The compounds in the instant disclosure. | | |
|---|---|---|
| Compound No. | Chemical Structure | MS (M + H) |
| 04-81 | 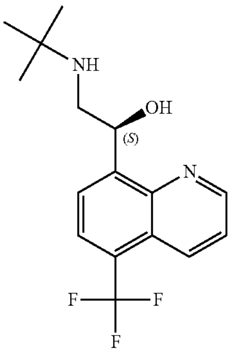 | 313 |
| 04-82 | 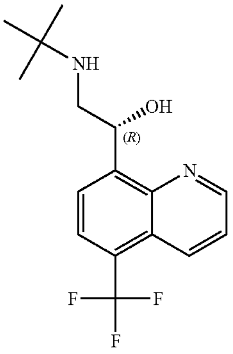 | 313.1 |
| 04-83 | 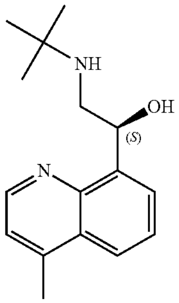 | 259.16 |
| 04-84 | 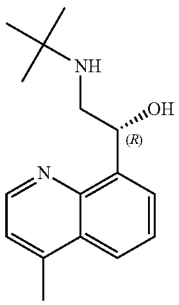 | 259.19 |

TABLE 1-continued
The compounds in the instant disclosure.
| Compound No. | Chemical Structure | MS (M + H) |
|---|---|---|
| 04-85 | 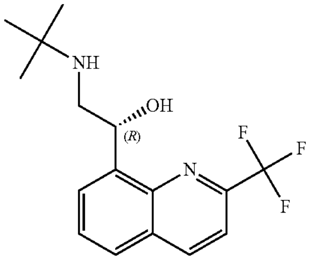 | 313.1 |
| 04-86 | 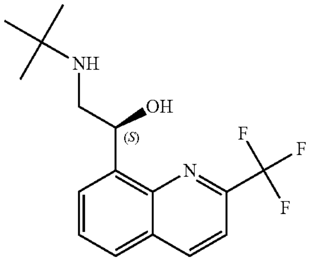 | 313.1 |
| 04-87 | 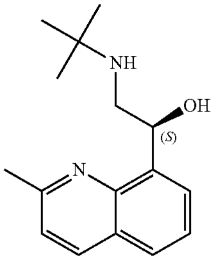 | 259.43 |
| 04-88 | 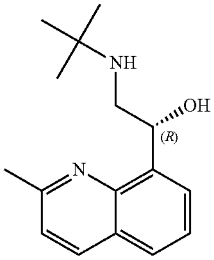 | 259.43 |
| 04-89 | 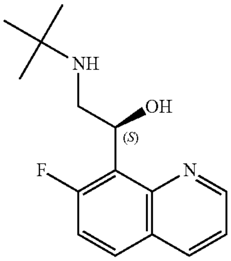 | 263.24 |

TABLE 1-continued
The compounds in the instant disclosure.
| Compound No. | Chemical Structure | MS (M + H) |
|---|---|---|
| 04-90 | 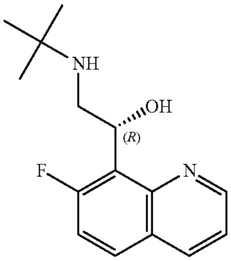 | 263.29 |
| 04-91 | 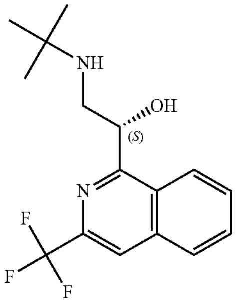 | 313.32 |
| 04-92 | 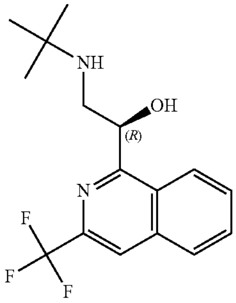 | 313.28 |
| 04-93 | 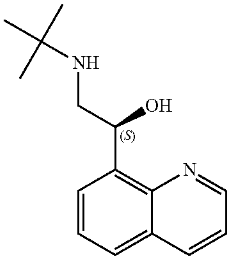 | 245.28 |
| 04-94 | 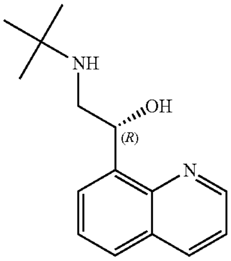 | 245.1 |

TABLE 1-continued
The compounds in the instant disclosure.
| Compound No. | Chemical Structure | MS (M + H) |
|---|---|---|
| 04-95 | 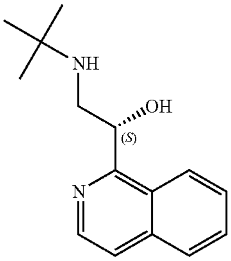 | 245.1 |
| 04-96 | 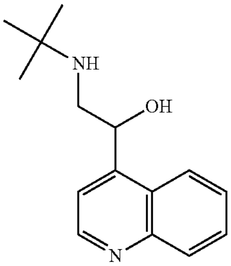 [SMILES: CC(C)(C)NCC(O)c1ccnc2ccccc12] | 245.2 |
| 04-97 | 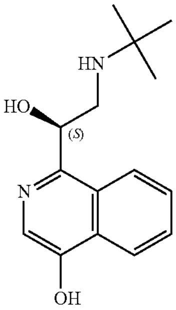 | 261.26 |
| 04-98 | 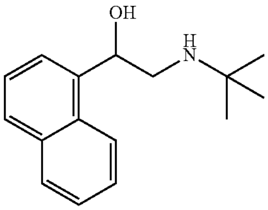 [SMILES: CC(C)(C)NCC(O)c1cccc2ccccc12] | 244.2 |
| 04-99 | 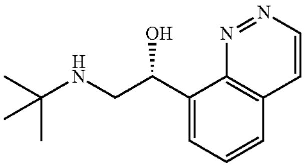 [SMILES: CC(C)(C)NC[C@H](O)c1cccc2ccnnc12] | |
| 04-100 | 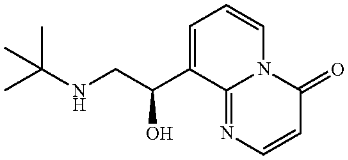 [SMILES: CC(C)(C)NC[C@H](O)c1cccn2c(=O)ccnc12] | |

TABLE 1-continued
| The compounds in the instant disclosure. | | |
|---|---|---|
| Compound No. | Chemical Structure | MS (M + H) |
| 04-101 | 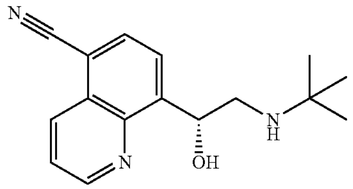 [SMILES: CC(C)(C)NC[C@H](O)c1ccc(C#N)c2cccnc12] | |
| 04-102 | 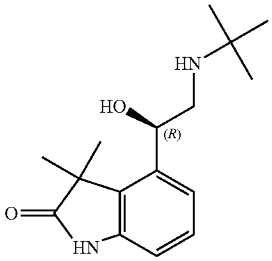 | 277.4 |
| 04-103 | 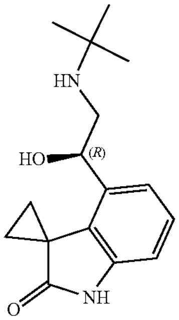 | 275.4 |
| 04-104 | 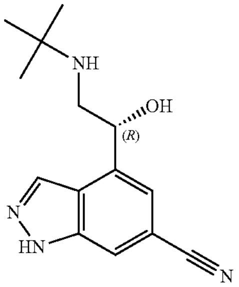 | 259.3 |
| 04-105 | 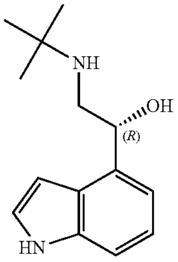 | 233.4 |

TABLE 1-continued
| The compounds in the instant disclosure. | | |
|---|---|---|
| Compound No. | Chemical Structure | MS (M + H) |
| 04-106 | 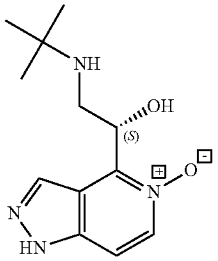 | 251.3 |
| 04-107 | 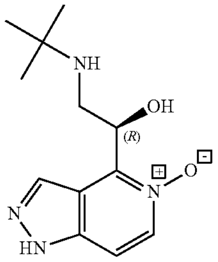 | 251.3 |
| 04-108 | 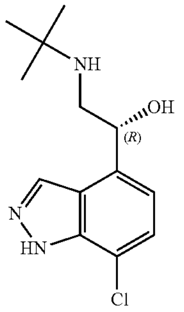 | 268.8 |
| 04-109 | 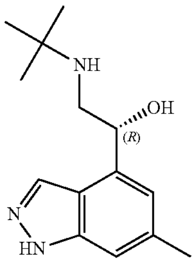 | 248.3 |
| 04-110 | 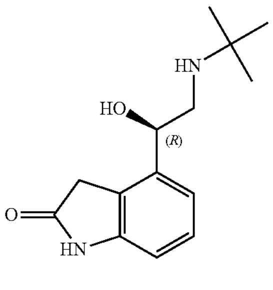 | 249.3 |

TABLE 1-continued
| The compounds in the instant disclosure. | | |
|---|---|---|
| Compound No. | Chemical Structure | MS (M + H) |
| 04-111 | 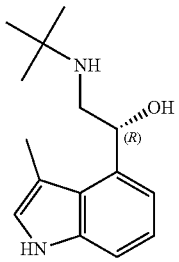 | 247.4 |
| 04-112 | 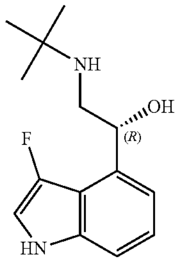 | 251.2 |
| 04-113 | 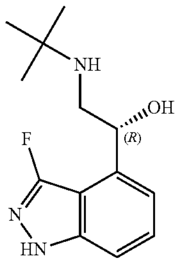 | 252.3 |
| 04-114 | 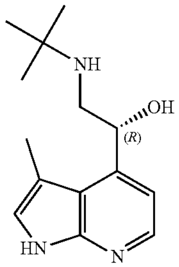 | 248.3 |
| 04-115 | 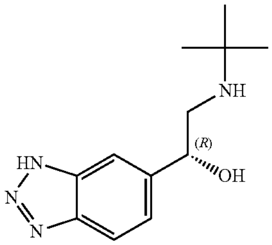 | 235.3 |

TABLE 1-continued
The compounds in the instant disclosure.
| Compound No. | Chemical Structure | MS (M + H) |
|---|---|---|
| 04-116 | 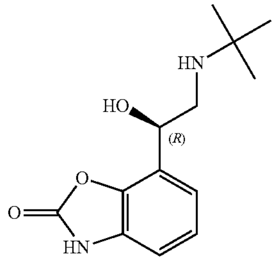 | 251.3 |
| 04-117 | 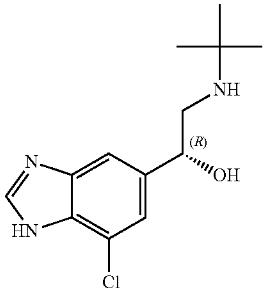 | 268.8 |
| 04-118 | 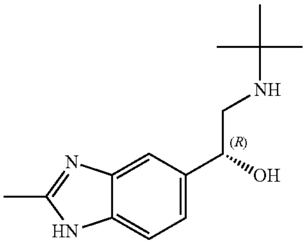 | 248.3 |
| 04-119 | 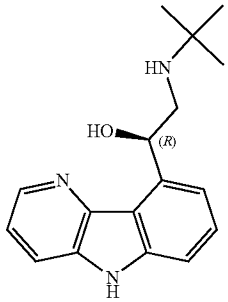 | 284.4 |
| 04-120 | 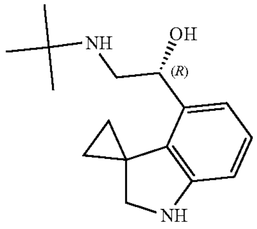 | 261.4 |
| 04-121 | 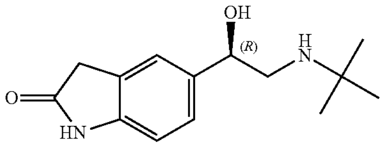 | 249.3 |

TABLE 1-continued
The compounds in the instant disclosure.
| Compound No. | Chemical Structure | MS (M + H) |
|---|---|---|
| 04-122 | 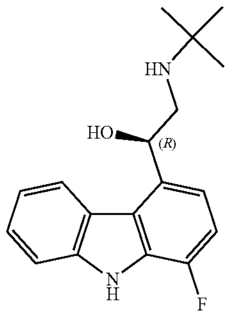 | 301.4 |
| 04-123 | 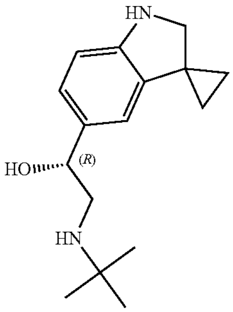 | 261.4 |
| 04-124 | 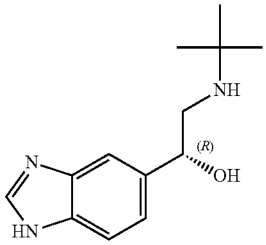 | 234.3 |
| 04-125 | 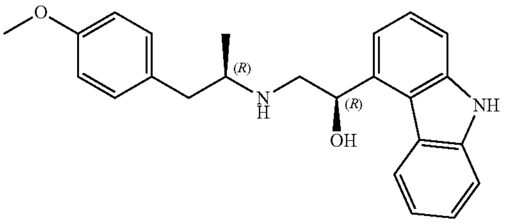 | 375.5 |
| 04-126 | 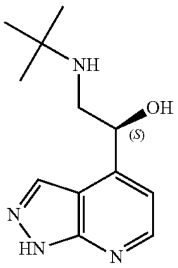 | 235.3 |

TABLE 1-continued
| The compounds in the instant disclosure. | | |
|---|---|---|
| Compound No. | Chemical Structure | MS (M + H) |
| 04-127 | 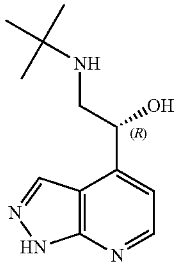 | 235.3 |
| 04-128 | 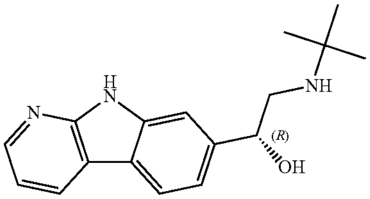 | 284.4 |
| 04-129 | 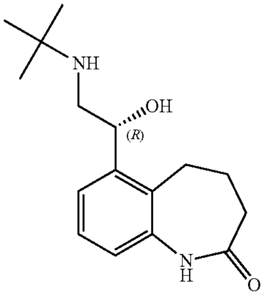 | 277.4 |
| 04-130 | 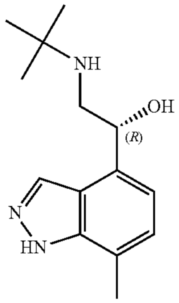 | 248.3 |
| 04-131 | 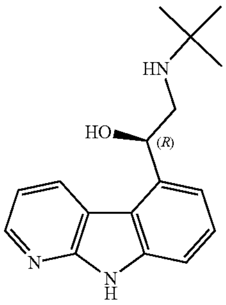 | 284.4 |

TABLE 1-continued
| The compounds in the instant disclosure. | | |
|---|---|---|
| Compound No. | Chemical Structure | MS (M + H) |
| 04-133 | 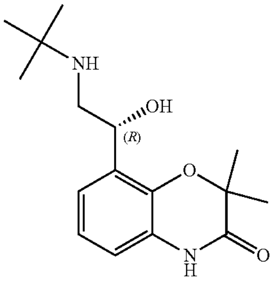 | 293.4 |
| 04-134 | 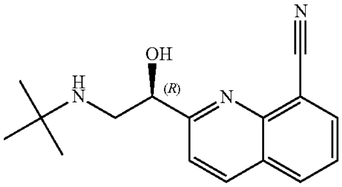 | 270.3 |
| 04-135 | 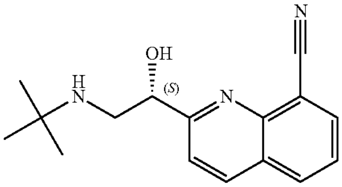 | 270.3 |
| 04-136 | 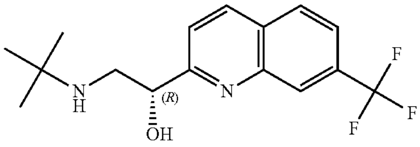 | 313.3 |
| 04-137 | 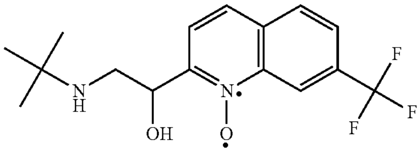 | 329.3 |
| 04-138 | 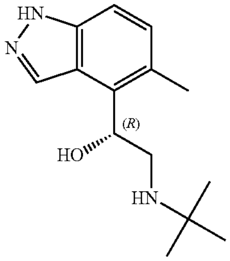 | 248.2 |
| 04-139 | 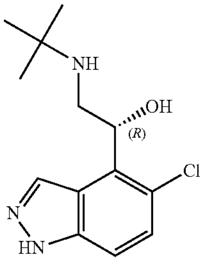 | 268.4 |

TABLE 1-continued
| The compounds in the instant disclosure. | | |
|---|---|---|
| Compound No. | Chemical Structure | MS (M + H) |
| 04-140 | 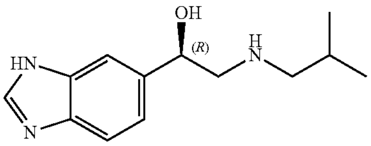 | 234.4 |
| 04-141 | 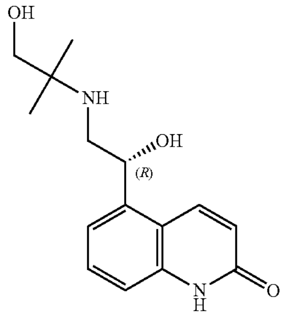 | 277.4 |
| 04-142 | 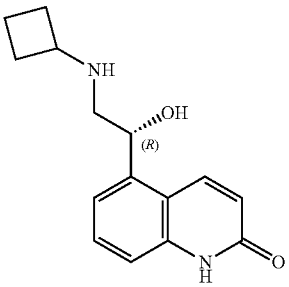 | 259.4 |
| 04-143 | 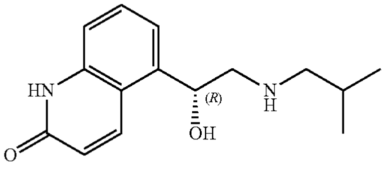 | 261.4 |
| 04-144 | 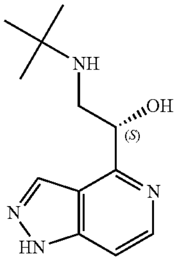 | 235.3 |
| 04-145 | 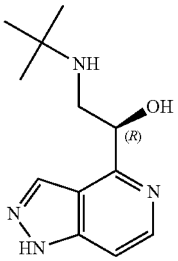 | 235.3 |

TABLE 1-continued
| The compounds in the instant disclosure. | | |
|---|---|---|
| Compound No. | Chemical Structure | MS (M + H) |
| 04-146 | 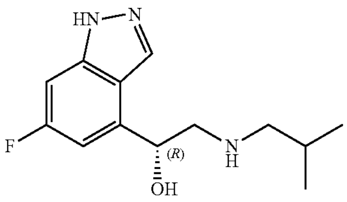 | 252.2 |
| 04-147 | 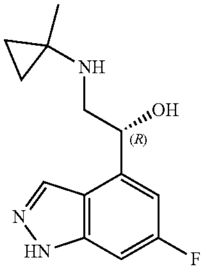 | 250.4 |
| 04-148 | 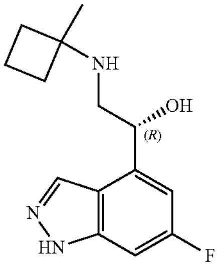 | 264.4 |
| 04-149 | 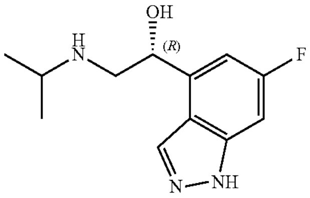 | 238.2 |
| 04-150 | 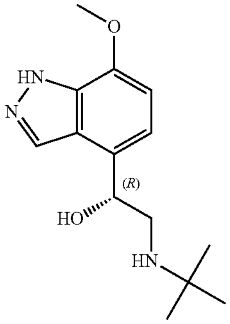 | 264.3 |

TABLE 1-continued
| The compounds in the instant disclosure. | | |
|---|---|---|
| Compound No. | Chemical Structure | MS (M + H) |
| 04-151 | 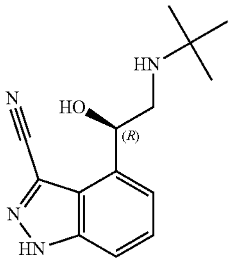 | 259.4 |
| 04-152 | 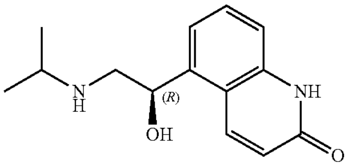 | 247.4 |
| 04-153 | 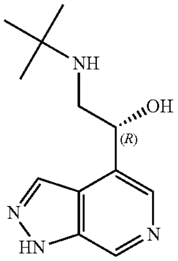 | 235.4 |
| 04-154 | 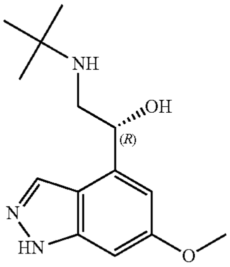 | 264.2 |
| 04-155 | 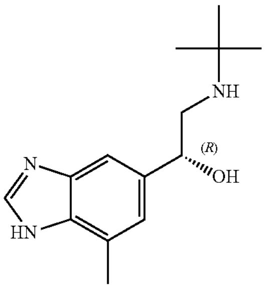 | 248.5 |

TABLE 1-continued
| The compounds in the instant disclosure. | | |
|---|---|---|
| Compound No. | Chemical Structure | MS (M + H) |
| 04-156 | 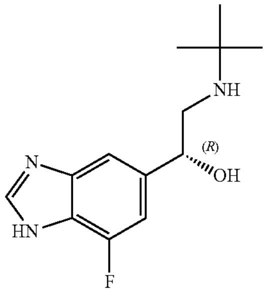 | 252.4 |
| 04-157 | 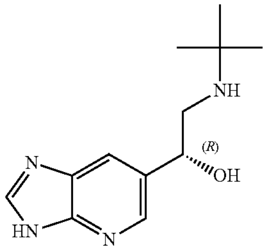 | 235.5 |
| 04-158 | 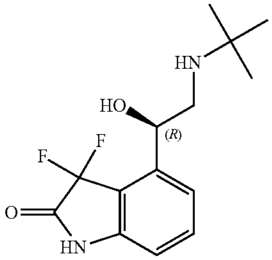 | 285.4 |
| 04-159 | 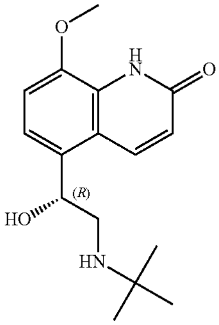 | 291.3 |
| 04-160 | 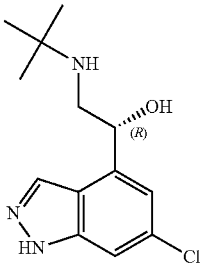 | 268.3 |

TABLE 1-continued
The compounds in the instant disclosure.
| Compound No. | Chemical Structure | MS (M + H) |
|---|---|---|
| 04-161 | 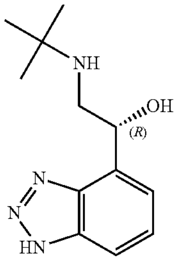 | 235.2 |
| 04-162 | 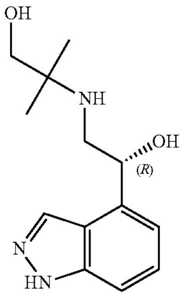 | 250.2 |
| 04-163 | 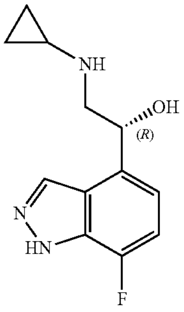 | 236.5 |
| 04-164 | 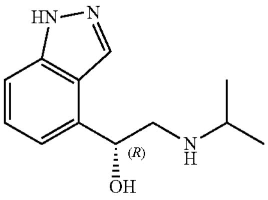 | 220.2 |
| 04-165 | 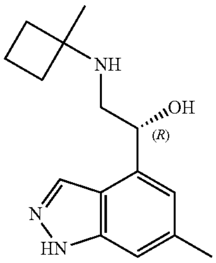 | 260.2 |

TABLE 1-continued
| The compounds in the instant disclosure. | | |
|---|---|---|
| Compound No. | Chemical Structure | MS (M + H) |
| 04-166 | 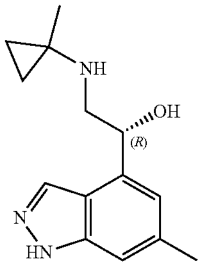 | 246.2 |
| 04-167 | 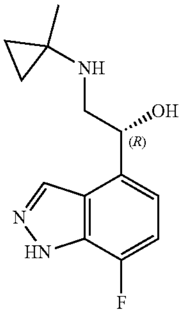 | 250.1 |
| 04-168 | 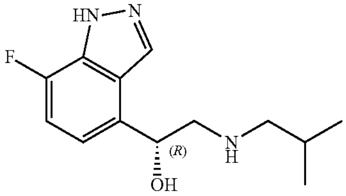 | 252.1 |
| 04-169 | 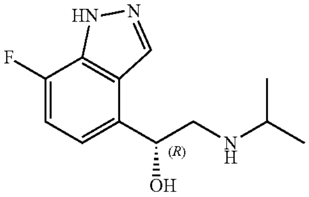 | 238.1 |
| 04-170 | 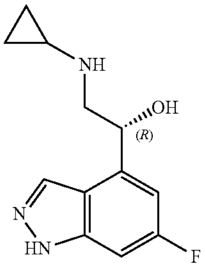 | 236.3 |

TABLE 1-continued
The compounds in the instant disclosure.
| Compound No. | Chemical Structure | MS (M + H) |
|---|---|---|
| 04-171 | 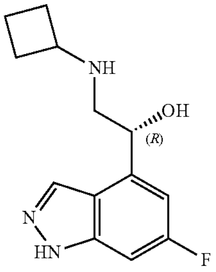 | 250.2 |
| 04-172 | 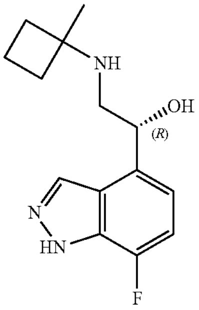 | 264.1 |
| 04-173 | 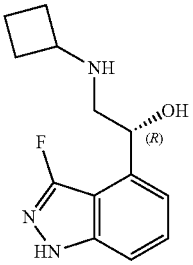 | 250.1 |
| 04-174 | 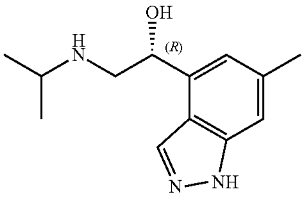 | 234.5 |
| 04-175 | 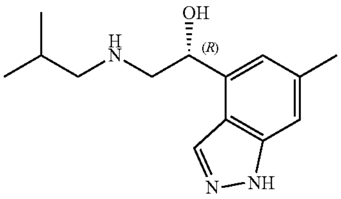 | 248.5 |
| 04-176 | 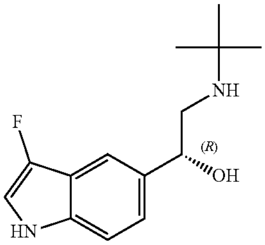 | 251.2 |

TABLE 1-continued
| The compounds in the instant disclosure. | | |
|---|---|---|
| Compound No. | Chemical Structure | MS (M + H) |
| 04-177 | 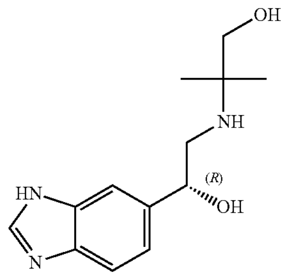 | 250.3 |
| 04-178 | 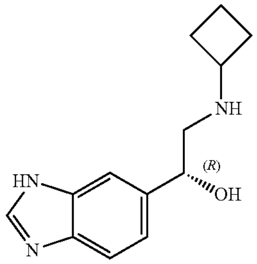 | 232.3 |
| 04-179 | 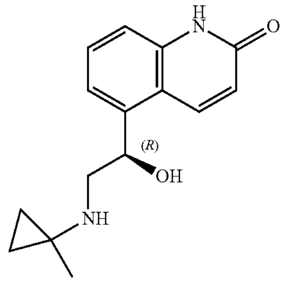 | 259.4 |
| 04-180 | 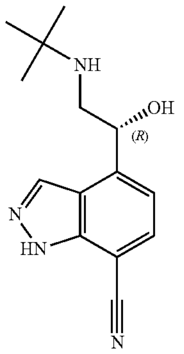 | 259.3 |
| 04-181 | 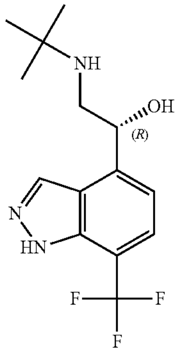 | 302.3 |

TABLE 1-continued
| The compounds in the instant disclosure. | | |
|---|---|---|
| Compound No. | Chemical Structure | MS (M + H) |
| 04-182 | 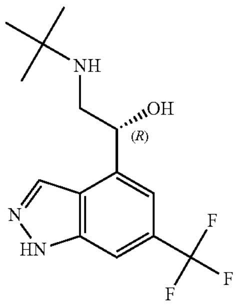 | 302.3 |
| 04-183 | 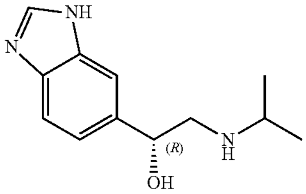 | 220.3 |
| 04-184 | 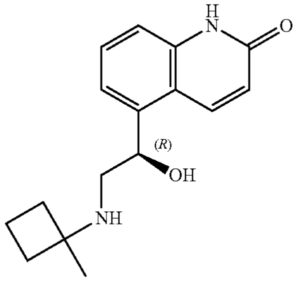 | 273.3 |
| 04-185 | 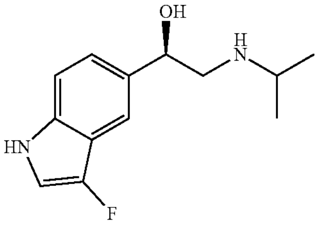 [SMILES: CC(C)NC[C@H](O)c1ccc2[nH]cc(F)c2c1] | |
| 04-186 | 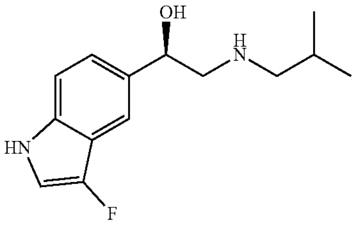 [SMILES: CC(C)CNC[C@H](O)c1ccc2[nH]cc(F)c2c1] | |
| 04-187 | 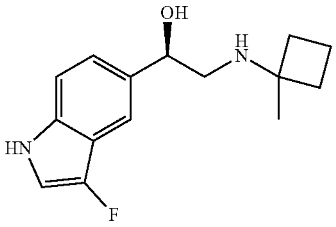 [SMILES: CC1(NC[C@H](O)c2ccc3[nH]cc(F)c3c2)CCC1] | |

TABLE 1-continued
| The compounds in the instant disclosure. | | |
|---|---|---|
| Compound No. | Chemical Structure | MS (M + H) |
| 04-188 | 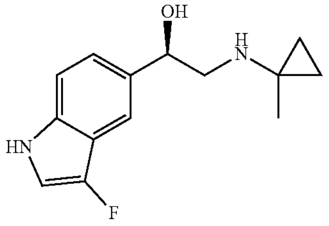 [SMILES: CC1(NC[C@H](O)c2ccc3[nH]cc(F)c3c2)CC1] | |
| 04-189 | 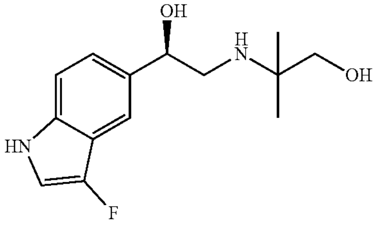 [SMILES: CC(C)(CO)NC[C@H](O)c1ccc2[nH]cc(F)c2c1] | |
| 04-190 | 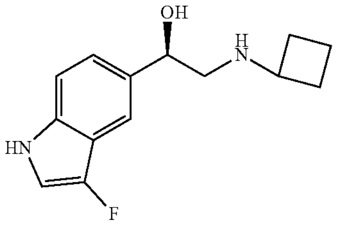 [SMILES: O[C@@H](CNC1CCC1)c1ccc2[nH]cc(F)c2c1] | |
| 04-191 | 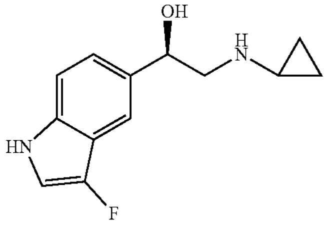 [SMILES: O[C@@H](CNC1CC1)c1ccc2[nH]cc(F)c2c1] | |
| 04-193 | 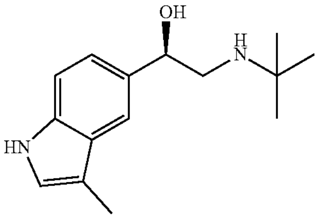 [SMILES: Cc1c[nH]c2ccc([C@@H](O)CNC(C)(C)C)cc12] | |
| 04-194 | 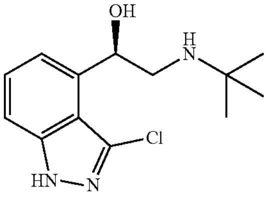 [SMILES: CC(C)(C)NC[C@H](O)c1cccc2[nH]nc(Cl)c12] | |

TABLE 1-continued
The compounds in the instant disclosure.
| Compound No. | Chemical Structure | MS (M + H) |
|---|---|---|
| 04-195 | 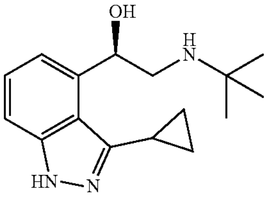 [SMILES: CC(C)(C)NC[C@H](O)c1cccc2[nH]nc(C3CC3)c12] | |
| 04-196 | 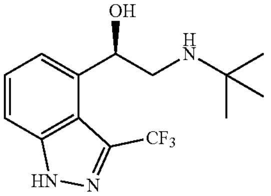 [SMILES: CC(C)(C)NC[C@H](O)c1cccc2[nH]nc(C(F)(F)F)c12] | |
| 04-197 | 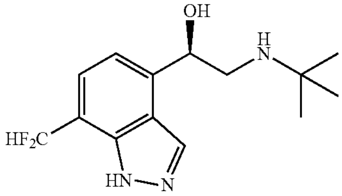 | |
| 04-198 | 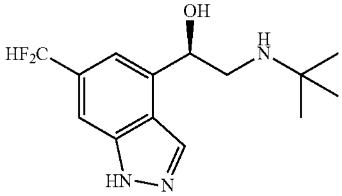 | |
| 04-199 | 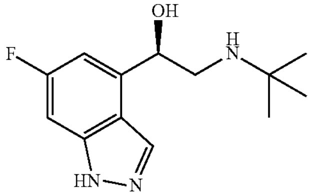 [SMILES: CC(C)(C)NC[C@H](O)c1cc(F)cc2[nH]ncc12] | |
| 04-200 | 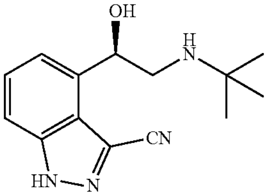 [SMILES: CC(C)(C)NC[C@H](O)c1cccc2[nH]nc(C#N)c12] | |
| 04-201 | 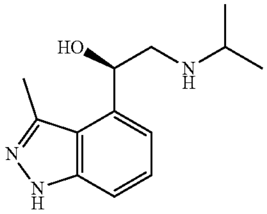 [SMILES: Cc1n[nH]c2cccc([C@@H](O)CNC(C)C)c12] | |

TABLE 1-continued
| The compounds in the instant disclosure. | | |
|---|---|---|
| Compound No. | Chemical Structure | MS (M + H) |
| 04-203 | 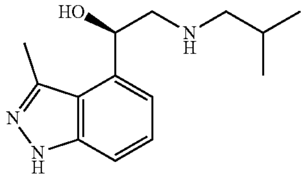 [SMILES: Cc1n[nH]c2cccc([C@@H](O)CNCC(C)C)c12] | |
| 04-204 | 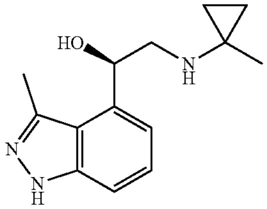 | |
| 04-205 | 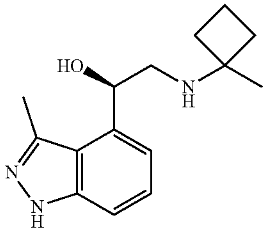 [SMILES: Cc1n[nH]c2cccc([C@@H](O)CNC3(C)CCC3)c12] | |
| 04-206 | 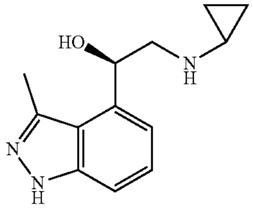 [SMILES: Cc1n[nH]c2cccc([C@@H](O)CNC3CC3)c12] | |
| 04-207 | 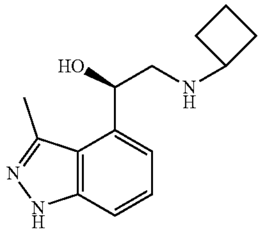 [SMILES: Cc1n[nH]c2cccc([C@@H](O)CNC3CCC3)c12] | |
| 04-208 | 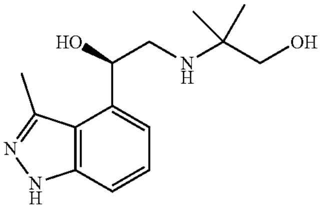 [SMILES: Cc1n[nH]c2cccc([C@@H](O)CNC(C)(C)CO)c12] | |
| 04-209 | 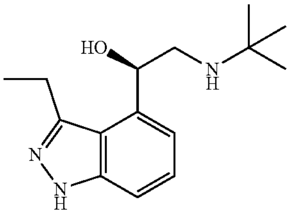 [SMILES: CCc1n[nH]c2cccc([C@@H](O)CNC(C)(C)C)c12] | |

TABLE 1-continued
The compounds in the instant disclosure.
| Compound No. | Chemical Structure | MS (M + H) |
|---|---|---|
| 04-210 | 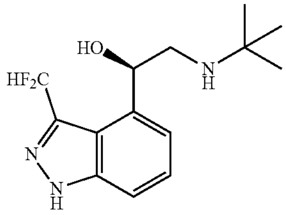 | |
| 04-211 | 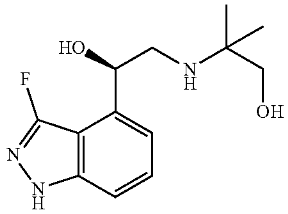 [SMILES: CC(C)(CO)NC[C@H](O)c1cccc2[nH]nc(F)c12] | 268.3 |
| 04-212 | 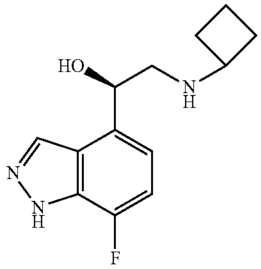 [SMILES: O[C@@H](CNC1CCC1)c1ccc(F)c2[nH]ncc12] | |
| 04-213 | 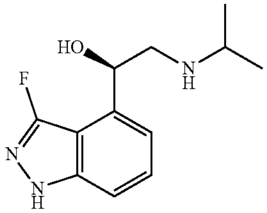 [SMILES: CC(C)NC[C@H](O)c1cccc2[nH]nc(F)c12] | 238.1 |
| 04-214 | 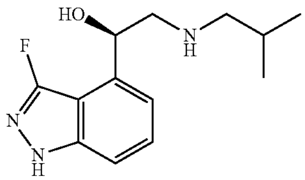 | 252.2 |
| 04-215 | 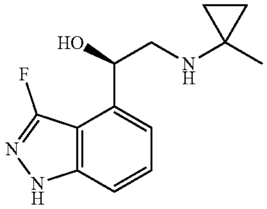 [SMILES: CC1(NC[C@H](O)c2cccc3[nH]nc(F)c23)CC1] | 232.1 |

TABLE 1-continued
| The compounds in the instant disclosure. | | |
|---|---|---|
| Compound No. | Chemical Structure | MS (M + H) |
| 04-215 | 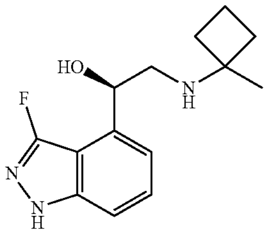 [SMILES: CC1(NC[C@H](O)c2cccc3[nH]nc(F)c23)CCC1] | 264.1 |
| 04-216 | 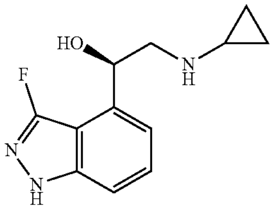 [SMILES: O[C@@H](CNC1CC1)c1cccc2[nH]nc(F)c12] | 236.1 |
| 04-217 | 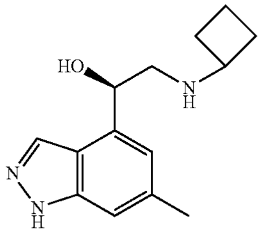 [SMILES: Cc1cc([C@@H](O)CNC2CCC2)c2cn[nH]c2c1] | 246.1 |
| 04-218 | 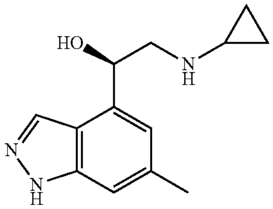 [SMILES: Cc1cc([C@@H](O)CNC2CC2)c2cn[nH]c2c1] | 232.2 |
| 04-219 | 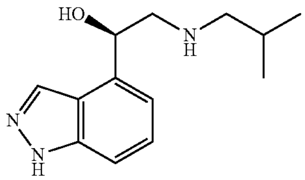 [SMILES: CC(C)CNC[C@H](O)c1cccc2[nH]ncc12] | 234.2 |
| 04-220 | 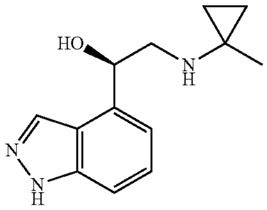 [SMILES: CC1(NC[C@H](O)c2cccc3[nH]ncc23)CC1] | |

TABLE 1-continued
The compounds in the instant disclosure.
| Compound No. | Chemical Structure | MS (M + H) |
|---|---|---|
| 04-221 | 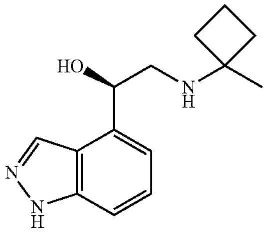 [SMILES: CC1(NC[C@H](O)c2cccc3[nH]ncc23)CCC1] | |
| 04-222 | 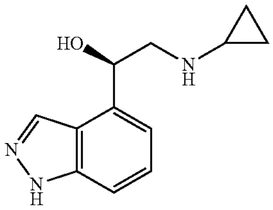 [SMILES: O[C@@H](CNC1CC1)c1cccc2[nH]ncc12] | 218.2 |
| 04-223 | 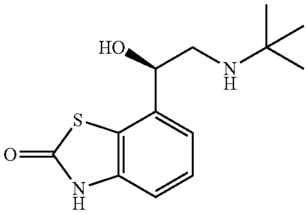 [SMILES: CC(C)(C)NC[C@H](O)c1cccc2[nH]c(=O)sc12] | |
| 04-224 | 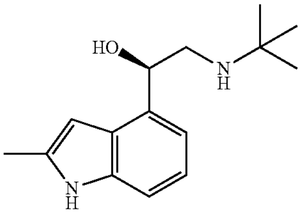 [SMILES: Cc1cc2c([C@@H](O)CNC(C)(C)C)cccc2[nH]1] | |
| 04-225 | 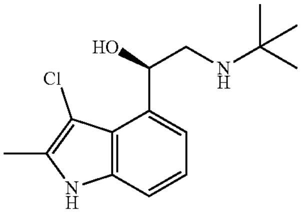 [SMILES: Cc1[nH]c2cccc([C@@H](O)CNC(C)(C)C)c2c1Cl] | |
| 04-226 | 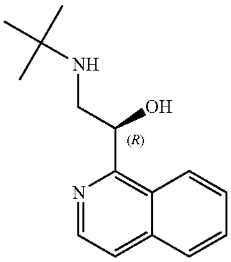 | 245.1 |

Also disclosed herein is a pharmaceutical composition including a compound with a structure of Formula (I), Formula (I'), Formula (II), Formula (II'), Formula (III'), Formula (IV'), Formula (V'), Formula (VI'), Formula (VII'), and a pharmaceutically acceptable excipient. Further disclosed is a method of treating a subject with a disease associated with an adrenergic receptor, the method comprising or administering to the subject a therapeutically effective amount of a compound with a structure of Formula (I), Formula (I'), Formula (II), Formula (II'), Formula (III'), Formula (IV'), Formula (V'), Formula (VI'), or Formula (VII'), thereby treating the subject. In some embodiments, the disease is a neurodegenerative disease, the subject is a human.

In some embodiments, the disease is selected from the group consisting of myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis. In some embodiments, the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route. In one embodiment, the compound is selected from those compounds set forth in Table 1.

The following examples are provided to further illustrate the advantages and features of the present disclosure, but they are not intended to limit the scope of the disclosure. While the examples is typical of those that might be used, other procedures, methodologies, or techniques known to those skilled in the art may alternatively be used.

EXAMPLES

Example I

Compound Synthesis

Scheme 1. Synthesis of compound 02-1.

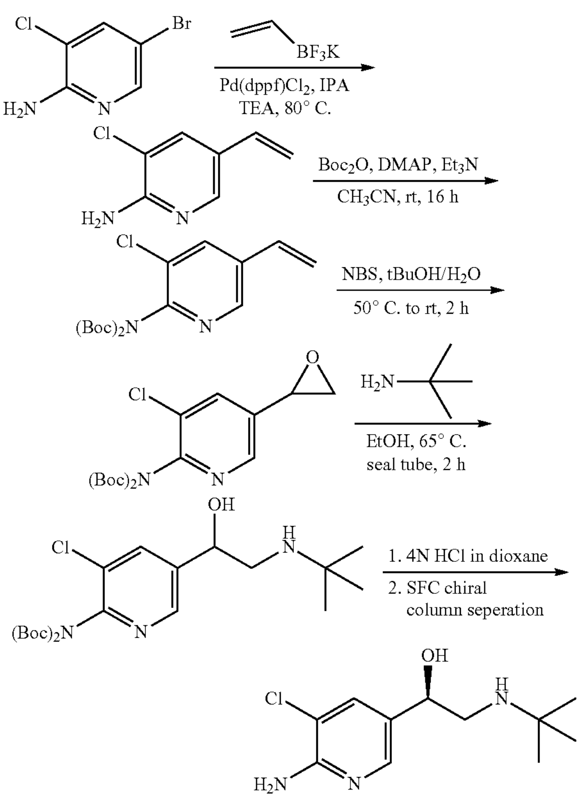

compound 02-1

Scheme 1 illustrates the synthesis of compound 02-1. $^1$H NMR (400 MHz, DMSO-$d_6$) δ 7.86 (d, J=1.6 Hz, 1H), 7.52 (d, J=1.6 Hz, 1H), 6.12 (s, 2H), 5.16 (bs, 1H), 4.40 (m, 1H), 2.62 (m, 2H), 1.29 (bs, 1H), 1.00 (s, 9H); LC-MS: m/z 244.2 $(M+1)^+$.

Scheme 2. Synthesis of compound 02-2.

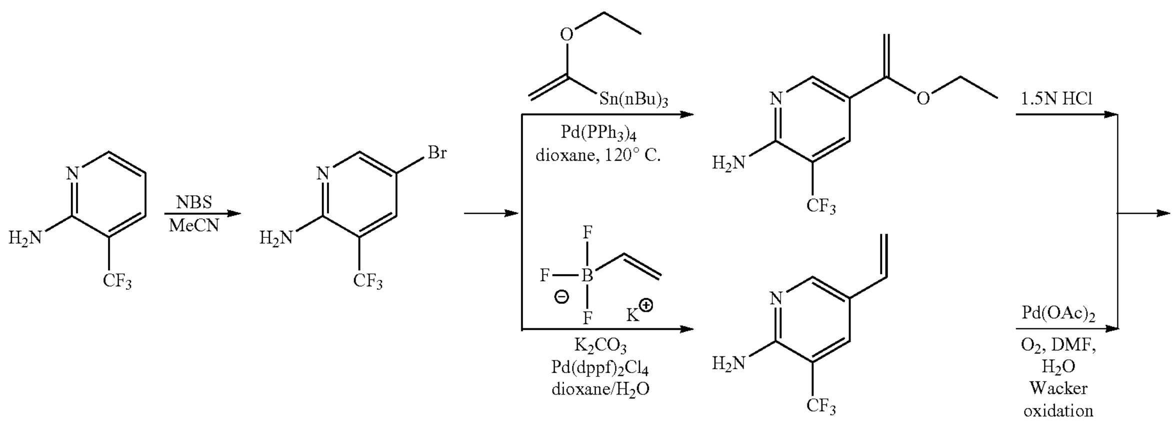

-continued

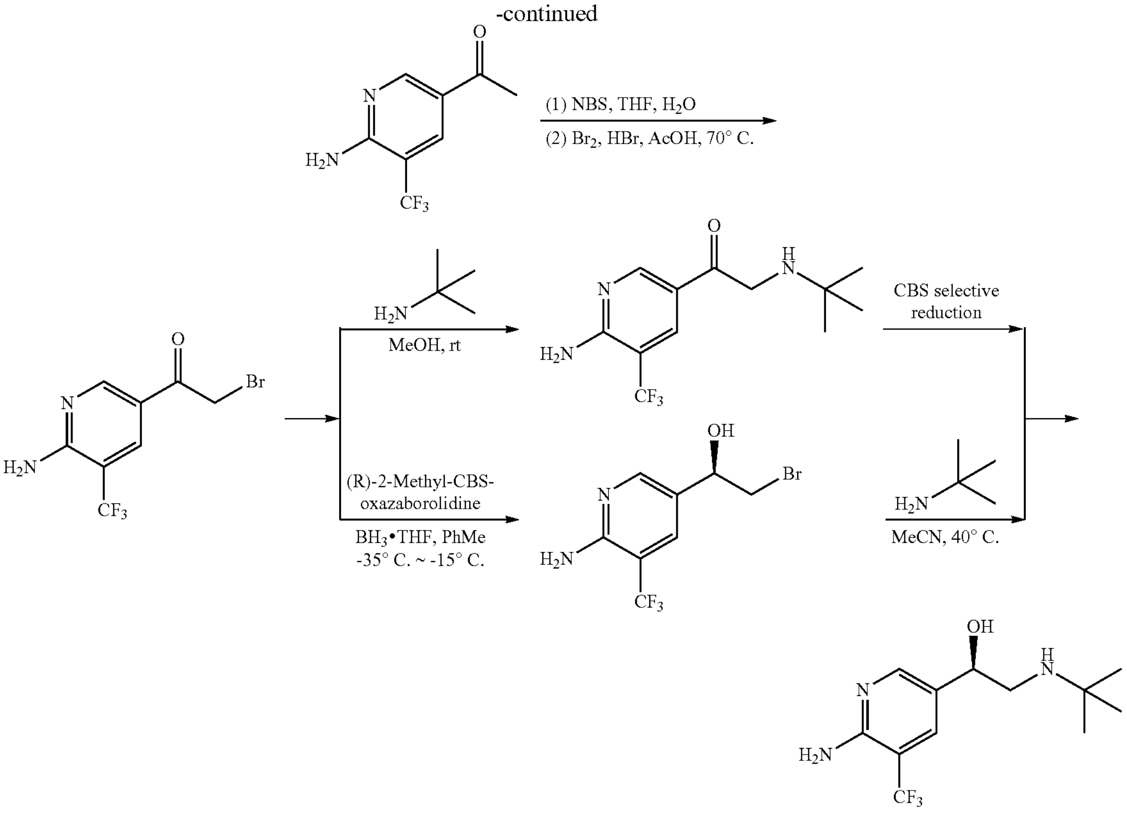

compound 02-2

Scheme 2 illustrates the synthesis of compound 02-2. $^1H$ NMR (400 MHz, DMSO-$d_6$) δ 8.37 (d, J=2.3 Hz, 1H), 8.08 (d, J=2.2 Hz, 1H), 6.77 (s, 2H), 4.48 (d, J=4.9 Hz, 1H), 3.86-3.79 (m, 1H), 3.69 (dd, J=11.5, 5.1 Hz, 1H), 1.25 (s, 9H); LC-MS: m/z 278.2 $(M+1)^+$.

Scheme 3. Synthesis of compound 02-3.

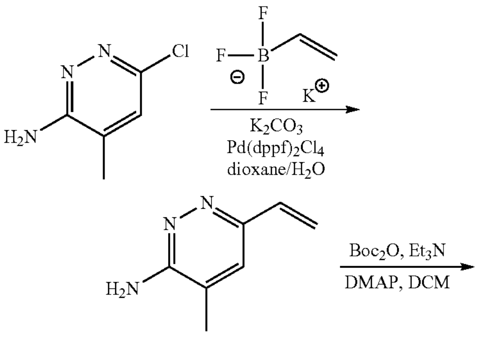

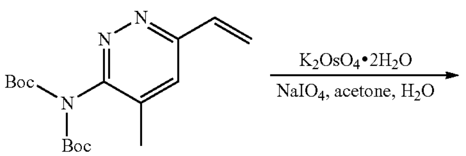

-continued

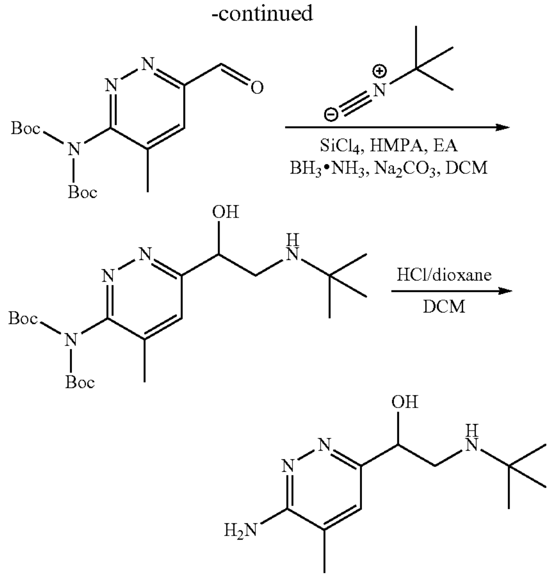

compound 02-3

Scheme 3 illustrates the synthesis of compound 02-3.

Step 1: Synthesis of 4-methyl-6-vinylpyridazin-3-amine. To a stirred solution of 6-chloro-4-methylpyridazin-3-amine (0.72 g, 5.01 mmol), potassium vinyltrifluoroborate (0.87 g, 6.51 mmol) and $K_2CO_3$ (2.07 g, 15.03 mmol) in dioxane/$H_2O$ (16 mL/4 mL) was added $Pd(dppf)_2Cl_2$ (0.367 g, 0.501 mmol). The resulting mixture was purged with $N_2$ before heating to 85° C. for 12 hrs. After cooled down, the reaction mixture was diluted with EtOAc. The organic layer was separated and washed with brine (30 mL). The aqueous layer was extracted with EtOAc (30 mL×3). The combined organic layers were dried over $Na_2SO_4$, filtered, and concentrated under reduced pressure. The residue was purified via flash chromatography eluting with DCM/$CH_3OH$ (30/1 to 10/1) to provide 4-methyl-6-vinylpyridazin-3-amine as a yellow solid (0.55 g, 82%). LC-MS: m/z 136.1 $(M+1)^+$.

Step 2: Synthesis of 4-methyl-6-vinylpyridazin-3-$N(Boc)_2$. To a stirred solution of 4-methyl-6-vinylpyridazin-3-amine (0.55 g, 4.1 mmol), di-tert-butyl dicarbonate (1.8 g, 8.2 mmol), and triethylamine (1.8 mL, 12.3 mmoL) in dichloromethane (16 mL) was added DMATP (0.025 g, 0.21 mmol). The resulting mixture was stirred at room temperature for 4 hrs. The reaction mixture was concentrated under reduced pressure. The residue was purified via flash chromatography eluting with DCM/$CH_3OH$ (40/1 to 15/1) to provide 4-methyl-6-vinylpyridazin-3-$N(Boc)_2$ as a white solid (1 g, 73%). LC-MS: m/z 336.1 $(M+1)^+$.

Step 3: Synthesis of 6-$N(Boc)_2$-5-methylpyridazine-3-carbaldehyde. To a stirred solution of 4-methyl-6-vinylpyridazin-3-$N(Boc)_2$ (0.5 g, 1.49 mmol) in acetone/$H_2O$ (16 mL/4 mL) were added $NaIO_4$ (0.96 g, 4.47 mmol) and $K_2OsO_4 \cdot H_2O$ (0.03 g, 0.075 mmol). The resulting mixture was stirred at room temperature for 24 hrs. The reaction mixture was partitioned between EtOAc (30 mL) and brine (30 mL). The organic layer was dried over $Na_2SO_4$, filtered, and concentrated under reduce pressure. The residue was purified via flash chromatography eluting with PE/EtOAc (30/1 to 2/1) to provide 6-$N(Boc)_2$-5-methylpyridazine-3-carbaldehyde (0.3 g, 59.7%). LC-MS: m/z 337.2 $(M+1)^+$.

Step 4: Synthesis of 1-(6-$N(Boc)_2$-5-methylpyridazin-3-yl)-2-(tert-butylamino)ethan-1-ol. tert-Butyl isocyanide (0.06 g, 0.70 mmol) was added to a stirred solution of 6-$N(Boc)_2$-5-methylpyridazine-3-carbaldehyde (0.2 g, 0.58 mmol), hexamethylphosphoramide (0.012 g, 0.058 mmol) and $SiCl_4$ (0.125 g, 0.66 mmol) in dichloromethane (4 mL) at −20° C. After stirring at −20° C. for 4 hrs, $BH_3NH_3$ (0.026 g, 0.88 mmol) was added. The mixture was stirred at room temperature for 3 hrs and then diluted with dichloromethane (10 mL). The organic solution was added to an aqueous solution of $Na_2CO_3$ (10 wt. %, 20 mL). The resulting mixture was stirred at room temperature for 30 minutes. The reaction mixture was filtered and washed with DCM (10 mL). The aqueous layer was separated and extracted with DCM (10 mL×2). The combined organic layers were dried over $Na_2SO_4$, filtered, and concentrated under reduced pressure. The residue was purified via flash chromatography eluting with DCM/$CH_3OH$ (30/1 to 10/1) to provide 1-(6-$N(Boc)_2$-5-methylpyridazin-3-yl)-2-(tert-butylamino)ethan-1-ol (0.025 g, 10%). LC-MS: m/z 425.3 $(M+1)^+$.

Step 5: Synthesis of 1-(6-amino-5-methylpyridazin-3-yl)-2-(tert-butylamino)ethan-1-ol. To a stirred solution of 1-(6-$N(Boc)_2$-5-methylpyridazin-3-yl)-2-(tert-butylamino)ethan-1-ol (0.025 g, 0.058 mmol) in dichloromethane (3 mL) was added 4N HCl in dioxane (3 mL, 12 mmol). The reaction mixture was stirred at room temperature for 24 hrs. The mixture was concentrated under reduced pressure to provide 1-(6-amino-5-methylpyridazin-3-yl)-2-(tert-butylamino) ethan-1-ol (0.012 g, 59.7%). $^1H$ NMR (400 MHz, DMSO-$d_6$) δ 9.29 (s, 1H), 8.65 (s, 1H), 8.47 (s, 2H), 7.90 (d, J=1.3 Hz, 1H), 6.74 (s, 1H), 5.06-4.96 (m, 1H), 3.21-3.13 (m, 2H), 2.31 (d, J=1.2 Hz, 3H), 1.32 (s, 9H). LC-MS: m/z 225.23 $(M+1)^+$.

Scheme 4. Synthesis of compound 02-4.

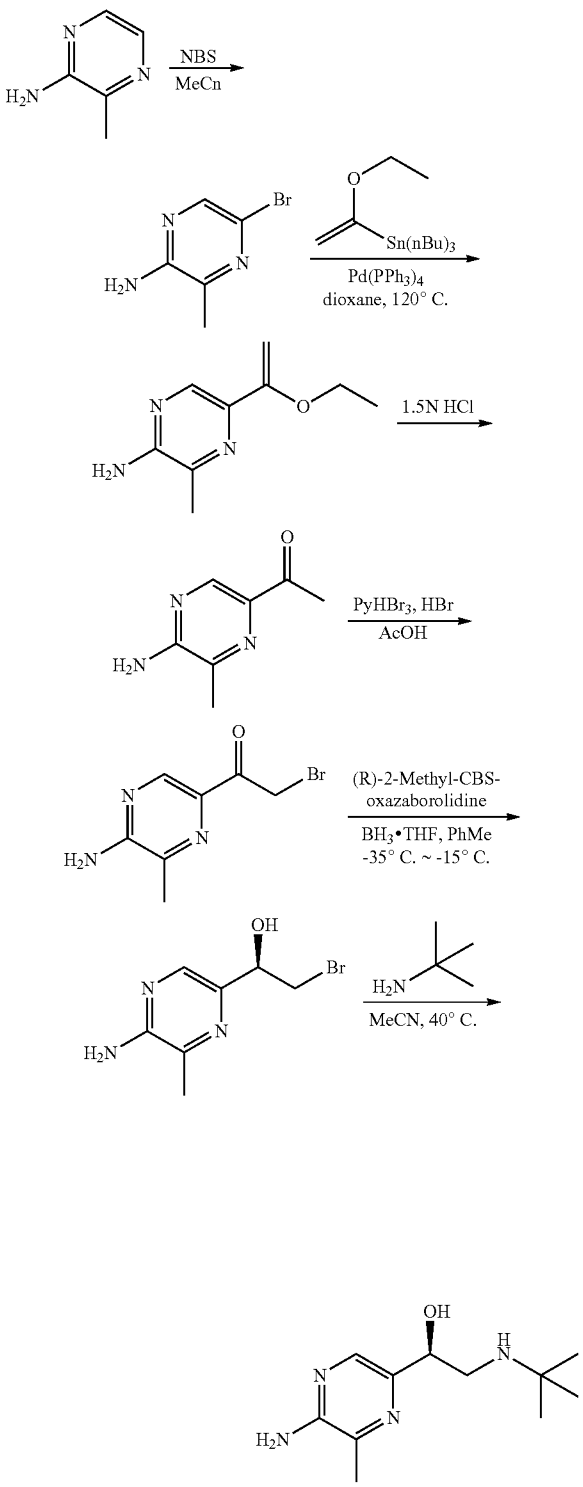

compound 02-4

Scheme 4 illustrates the synthesis of compound 02-4. $^1H$ NMR (400 MHz, Chloroform-d) δ 7.83 (s, 1H), 4.45 (s, 2H), 3.88 (dd, J=9.0, 4.9 Hz, 1H), 3.55 (dd, J=10.4, 4.9 Hz, 1H), 3.32 (t, J=9.7 Hz, 1H), 2.39 (d, J=0.7 Hz, 3H), 1.06 (s, 9H); LC-MS: m/z 225.2 $(M+1)^+$.

Scheme 5. Synthesis of compound 04-1.

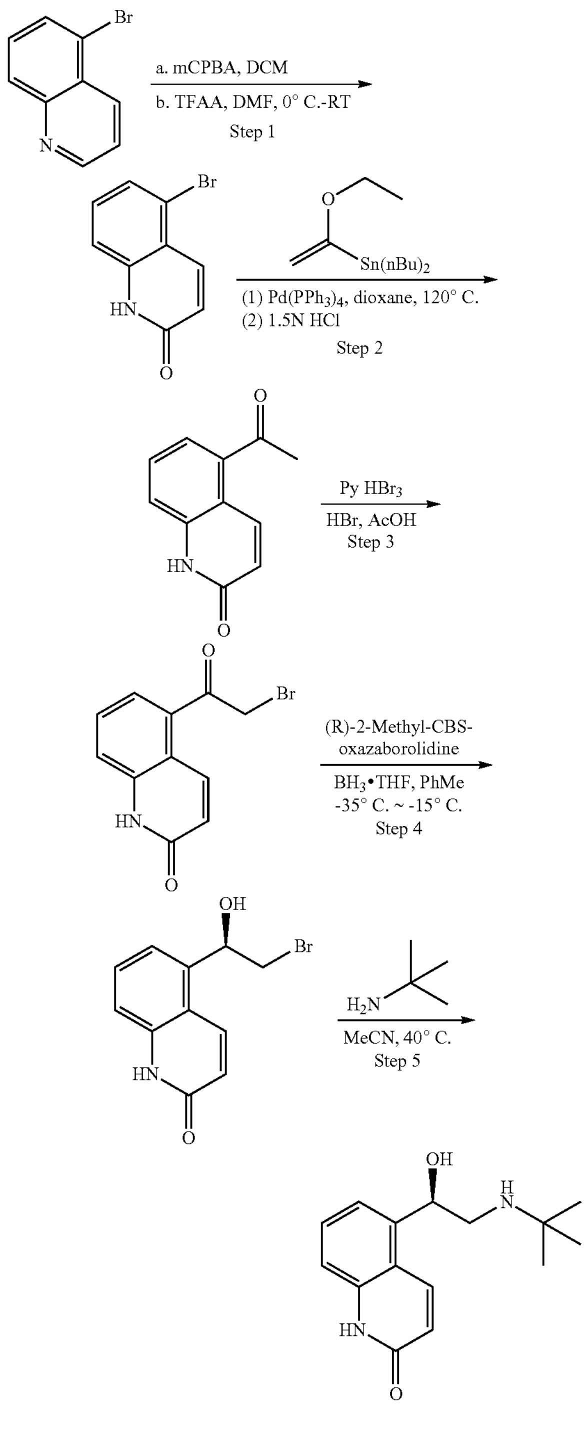

Scheme 5 illustrates the synthesis of compound 04-1.

Step 1: Synthesis of 5-bromoquinolin-2(1H)-one. (a) To a solution of 5-bromoquinoline (7.6 g, 36.5 mmol) in DCM (100 mL) was added m-CPBA (8.1 g, 47 mmol) in three portions at room temperature. Upon completion of addition, the reaction mixture was stirred at room temperature for 3 hrs. After this time, 1N NaOH aqueous solution (120 ml) was added to the reaction and the resulting mixture was extracted with DCM (100 mL×3). The combined organic layers were washed with brine, dried over anhydrous $MgSO_4$, filtered and concentrated to afford 5-Bromoquinoline 1-oxide (5.1 g, 63%) as a light-yellow solid. LC-MS: m/z 223.9 $(M+1)^+$. (b) To a solution of 5-bromoquinoline 1-oxide (5.1 g, 23 mmol) in DMF (50 mL) at 0° C. was added trifluoroacetic anhydride (24 g, 115 mmol) in three portions. The reaction was then stirred at room temperature overnight. The reaction mixture was quenched by a saturated aq. $NaHCO_3$ solution (300 mL) and extracted with DCM (100 mL×3). The combined organic layers were washed with brine, dried over anhydrous $MgSO_4$, filtered and concentrated to afford 5-bromoquinolin-2(1H)-one (4 g, 78%) as a yellow solid. LC-MS: m/z 223.9 $(M+1)^+$.

Step 2: Synthesis of 5-acetylquinolin-2(1H)-one. To a stirred solution of 5-bromoquinolin-2(1H)-one and 1-ethoxyvinyltri-n-butyltin (1.1 eq.) in dioxane was added $Pd(PPh_3)_4$ (0.05 eq). The resulting mixture was purged with $N_2$ (3×) before heating to 120° C. for 6 hrs. After cooled down, 1.5N HCl (2 eq.) was introduced to the flask and stirring was continued at rt overnight. The reaction solution was then quenched with saturated $NaHCO_3$ aqueous solution and extracted with EtOAc. The combined organic layers were washed with brine, dried over $Na_2SO_4$ and concentrated. The crude product was purified via flash chromatography to afford 5-acetylquinolin-2(1H)-one. LC-MS: m/z 188.1 $(M+1)^+$.

Step 3: Synthesis of 5-(2-bromoacetyl)quinolin-2(1H)-one. To a stirred solution of 5-acetylquinolin-2(1H)-one and HBr (40%) in AcOH was added pyridinium tribromide (1.2 eq.). The resulting mixture was stirred at 40° C. overnight. After cooling to rt the mixture was quenched with saturated $NaHCO_3$ aqueous solution. The reaction mixture was subsequently extracted with EtOAc. The combined organic layers were washed with brine, dried over $Na_2SO_4$ and concentrated. The crude product was purified via flash chromatography to afford 5-(2-bromoacetyl)quinolin-2(1H)-one. LC-MS: m/z 267.1 $(M+1)^+$.

Step 4: Synthesis of (R)-5-(2-bromo-1-hydroxyethyl)quinolin-2(1H)-one. To a stirred solution of 5-(2-bromoacetyl)quinolin-2(1H)-one in toluene was added (R)-2-methyl-CBS-oxazaborolidine (0.2 eq.) at −35° C. The resulting mixture was stirred at −35° C. for 30 minutes. $BH_3$.THF (1N in THF, 1 eq.) was then introduced dropwise via syringe. After addition, the reaction was warmed up to −15° C. After 2 hrs the reaction mixture was quenched with saturated $NaHCO_3$ aqueous solution (10 mL) and extracted with EtOAc. The combined organic layers were washed with brine, dried over $Na_2SO_4$ and concentrated. The crude product was purified via flash chromatography to afford (R)-5-(2-bromo-1-hydroxyethyl)quinolin-2(1H)-one. LC-MS: m/z 269.1 $(M+1)^+$.

Step 5: Synthesis of (R)-5-(2-(tert-butylamino)-1-hydroxyethyl)quinolin-2(1H)-one (Compound 04-1). To a stirred solution of (R)-5-(2-bromo-1-hydroxyethyl)quinolin-2(1H)-one in MeCN was added tert-butylamine (60 eq.). The resulting mixture was stirred at 40° C. for 48 hrs. The reaction was concentrated, and the residue was re-dissolved with EtOAc. The organic layer was washed with saturated $NaHCO_3$ aqueous solution and brine, dried over $Na_2SO_4$ and concentrated. The crude product was purified via HPLC (C18, $MeCN/H_2O$ (0.1% formic acid), (1%~100%)) to afford (R)-5-(2-(tert-butylamino)-1-hydroxyethyl)quinolin-2(1H)-one (04-1) as a white solid (5-step yield: 12%). $^1H$ NMR (400 MHz, DMSO-$d_6$) δ 11.82 (br, 1H), 8.21 (d, J=9.9 Hz, 1H), 7.52 (t, J=7.9 Hz, 1H), 7.36 (dd, J=7.6, 1.1 Hz, 1H), 7.28 (d, J=8.5 Hz, 1H), 6.57 (d, J=9.9 Hz, 1H), 5.38 (dd, J=9.6, 2.8 Hz, 1H), 3.00-2.85 (m, 2H), 1.24 (s, 9H). LC-MS: m/z 261.2 $(M+1)^+$.

Scheme 6. Synthesis of compound 04-5.

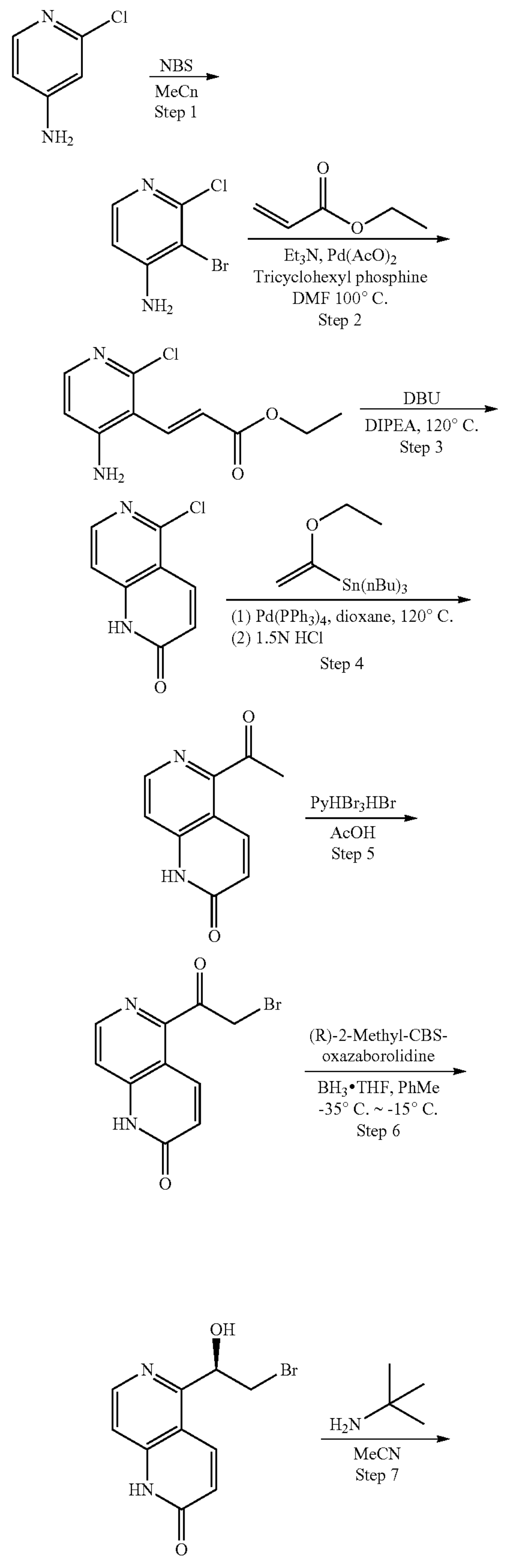

-continued

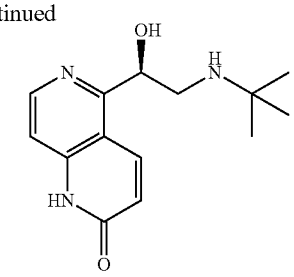

Scheme 6 illustrates the synthesis of compound 04-5.

Step 1: Synthesis of 3-bromo-2-chloropyridin-4-amine. To a stirred solution of 2-chloropyridin-4-amine (10 g, 77.78 mmoL) in MeCN (250 mL) was added N-Bromosuccinimide (13.8 g, 77.78 mmoL). The resulting mixture was stirred at room temperature for 12 hrs. The reaction was concentrated. The crude product was purified by purified via flash chromatography (silica, pet ether/EtOAc: 20/1 to 3/1) to afford 3-bromo-2-chloropyridin-4-amine as a yellow solid (7.1 g, 43.9%). LC-MS: m/z 206.94, 208.97 $(M+1, M+2)^+$.

Step 2: Synthesis of ethyl (E)-3-(4-amino-2-chloropyridin-3-yl)acrylate. To a stirred solution of 3-bromo-2-chloropyridin-4-amine (2 g, 9.6 mmoL), ethyl acrylate (1.9 g, 19.3 mmoL), $Et_3N$ (2.91 g, 28.8 mmoL) and tricyclohexyl phosphine (1.3 g, 4.8 mmol) in DMF (100 mL) was added $Pd(OAc_2)$ (431 mg, 1.9 mmoL, 0.2 eq). The resulting mixture was purged with $N_2$ (3×) before heating to 100° C. for 24 hrs. After cooled down, the reaction mixture was diluted with EtOAc (50 mL). The organic layer was washed with brine (30 mL×3) and dried over $Na_2SO_4$, filtered, and concentrated. The residue was purified by flash chromatography (silica, pet ether/EtOAc: 30/1 to 1/1) to afford ethyl (E)-3-(4-amino-2-chloropyridin-3-yl)acrylate as a yellow solid (1.2 g, 55.3%). LC-MS: m/z 227.1, 229.1 $(M+1, M+2)^+$.

Step 3: Synthesis of Synthesis of 5-chloro-1,6-naphthyridin-2(1H)-one. To a stirred solution of ethyl (E)-3-(4-amino-2-chloropyridin-3-yl)acrylate (2.5 g, 11.01 mmoL) in DIPEA (20 mL) was added DBU (3.3 g, 22.02 mmoL). The resulting mixture was stirred at 120° C. for 8 hrs. The reaction mixture was concentrated. The residue was purified by flash chromatography (silica, DCM/$CH_3OH$: 40/1 to 15/1) to give 5-chloro-1,6-naphthyridin-2(1H)-one (1 g, 50.2%). LC-MS: m/z 181.0, 183.0 $(M+1, M+2)^+$.

Step 4-7: Synthesis of (S)-5-(2-(tert-butylamino)-1-hydroxyethyl)-1,6-naphthyridin-2(1H)-one (Compound 04-5). Procedures similar to the synthesis of Compound 04-1 were employed using 5-chloro-1,6-naphthyridin-2(1H)-one instead of 5-bromoquinolin-2(1H)-one as starting material to obtain (S)-5-(2-(tert-butylamino)-1-hydroxyethyl)-1,6-naphthyridin-2(1H)-one (04-5) as a white solid, 12 mg, 4-step yield: 9.2%). $^1$H NMR (400 MHz, DMSO-$d_6$) δ 12.03 (br, 1H), 8.42 (d, J=5.7 Hz, 1H), 8.34 (d, J=9.9 Hz, 1H), 7.21 (d, J=5.7 Hz, 1H), 6.63 (d, J=9.9 Hz, 1H), 5.25 (t, J=6.3 Hz, 1H), 3.16 (d, J=6.7 Hz, 2H), 1.22 (d, J=12.6 Hz, 9H). LC-MS: m/z 262.2. $(M+1)^+$.

Scheme 7. Synthesis of compound 04-23.

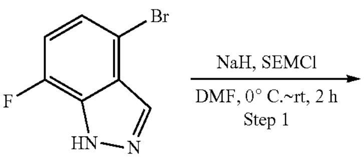

-continued

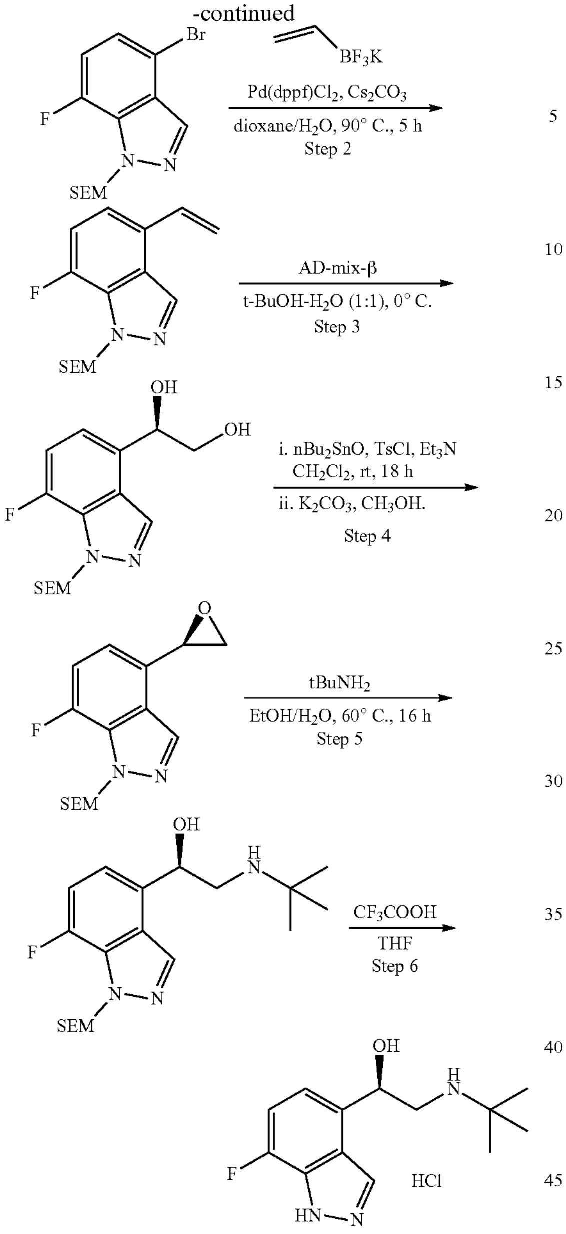

Scheme 7 illustrates the synthesis of compound 04-23.

Step 1: Synthesis of 4-bromo-7-fluoro-1-((2-(trimethylsilyl)ethoxy)methyl)-1H-indazole. To a stirred solution of 4-bromo-7-fluoro-1H-indazolel (2.5 g, 11.62 mmol) in DMF (20 mL) at 0° C. was added NaH (60%, 0.79 g, 19.75 mmol) portion-wise. The resulting mixture was stirred for 1 h, then 2-(trimethylsilyl)ethoxymethyl chloride (3.1 mL, 2.92 g, 17.44 mmol) was added. The mixture was stirred at room temperature for 6 hrs. The reaction was quenched with saturated ammonium chloride solution (20 mL). The mixture was extracted with ethyl acetate (50 mL×3). The combined organic layers were washed with $H_2O$ (100 mL×3), brine, dried over sodium sulfate, filtered, and concentrated under reduced pressure. The residue was purified via column chromatography eluting with 20% EtOAc in Petroleum ether to provide 4-bromo-7-fluoro-1-((2-(trimethylsilyl)ethoxy)methyl)-1H-indazole as a yellow oil (1.9 g, 48%). LC-MS: m/z 346.3 M+1)$^+$.

Step 2: Synthesis of 7-fluoro-1-((2-(trimethylsilyl)ethoxy)methyl)-4-vinyl-1H-indazole. To a stirred solution of 4-bromo-7-fluoro-1-((2-(trimethylsilyl)ethoxy)methyl)-1H-indazole (1.9 g, 5.51 mmol) in dioxane/$H_2O$ (20 mL/2 mL) was added potassium vinyltrifluoroborate (1.47 g, 11.01 mmol), Pd(dppf)$Cl_2$ $CH_2Cl_2$ (0.45 g, 0.55 mmol), $Cs_2CO_3$ (5.38 g, 16.5 mmol) under $N_2$. The mixture was stirred at 100° C. for 16 hrs. The reaction mixture was filtered through a pad of celite and washed with EtOAc (100 mL). The filtrate was washed with $H_2O$, brine, dried over $Na_2SO_4$, filtered, and concentrated under reduced pressure. The residue was purified via column chromatography eluting with 10% EtOAc in petroleum ether to provide 7-fluoro-1-((2-(trimethylsilyl)ethoxy)methyl)-4-vinyl-1H-indazole as an oil (1.6 g, 99%). LCMS: m/z 293.3 (M+1)$^+$.

Step 3: Synthesis of (R)-1-(7-fluoro-1-((2-(trimethylsilyl)ethoxy)methyl)-1H-indazol-4-yl)ethane-1,2-diol. To a stirred solution of 7-fluoro-1-((2-(trimethylsilyl)ethoxy)methyl)-4-vinyl-TH-indazole (1.6 g, 5.47 mmol) in tert-BuOH/$H_2O$ (20 mL/20 mL) at 0° C. was added AD-mix-beta (8.25 g), and then stirred at room temperature for 16 hrs. After the completion of the reaction, the mixture was quenched with saturated $Na_2SO_3$ solution (20 mL) and extracted with EtOAc (100 mL). The organic layer was concentrated under reduced pressure. The residue was purified via column chromatography eluting with 50% EtOAc in petroleum ether to provide (R)-1-(7-fluoro-1-((2-(trimethylsilyl)ethoxy)methyl)-1H-indazol-4-yl)ethane-1,2-diol as a yellow oil (2.1 g, 99%). LCMS: m/z 327.3 (M+1)$^+$.

Step 4: Synthesis of (R)-7-fluoro-4-(oxiran-2-yl)-1-((2-(trimethylsilyl)ethoxy)methyl)-1H-indazole. (i) To a stirred solution of (R)-1-(7-fluoro-1-((2-(trimethylsilyl)ethoxy)methyl)-1H-indazol-4-yl)ethane-1,2-diol (2.1 g, 6.4 mmol) in $CH_2Cl_2$ (20 mL) was added n-$Bu_2SnO$ (0.16 g, 0.64 mmol), p-TsCl (1.4 g, 7.1 mmol), and $Et_3N$ (776 mg, 7.6 mmol). The reaction mixture was then stirred at room temperature for 16 hrs. The reaction was quenched with water. The mixture was extracted with $CH_2Cl_2$ (50 mL×3). The combined organic layers were washed with water, brine, dried over sodium sulfate, filtered, and concentrated under reduced pressure. The residue was purified via column chromatography eluting with 30% EtOAc in petroleum ether to provide (R)-2-(7-fluoro-1-((2-(trimethylsilyl)ethoxy)methyl)-1H-indazol-4-yl)-2-hydroxyethyl 4-methylbenzenesulfonate as a yellow oil (2.76 g, 90%). LCMS: m/z 481.3 (M+1)$^+$. (ii) To a stirred solution of (R)-2-(7-fluoro-1-((2-(trimethylsilyl)ethoxy)methyl)-1H-indazol-4-yl)-2-hydroxyethyl 4-methylbenzenesulfonate (2.76 g, 5.76 mmol) in MeOH (10 mL) was added $K_2CO_3$ (3.97 g, 28.8 mmol). The resulting mixture was stirred at room temperature for 2 hrs. The reaction mixture was concentrated in vacuo to provide a residue, which was re-dissolved in $CH_2Cl_2$. Organic layer was then washed with $H_2O$, dried over $Na_2SO_4$, filtered, and concentrated in vacuo to provide (R)-7-fluoro-4-(oxiran-2-yl)-1-((2-(trimethylsilyl)ethoxy)methyl)-1H-indazole as an oil (2.1 g), which was used for next step without further purifications.

Step 5: Synthesis of (R)-2-(tert-butylamino)-1-(7-fluoro-1-((2-(trimethylsilyl)ethoxy)methyl)-1H-indazol-4-yl)ethan-1-ol. To a stirred solution of (R)-7-fluoro-4-(oxiran-2-yl)-1-((2-(trimethylsilyl)ethoxy)methyl)-1H-indazole (2.1 g, 6.48 mmol) in EtOH/$H_2O$ (4 mL/8 mL) was added tert-Bu$NH_2$ (2.37 g, 32.42 mmol). The reaction mixture was stirred at 60° C. for 18 hrs. The reaction mixture was concentrated in vacuo. The residue was purified by column chromatography eluting with 5% MeOH in dichloromethane to provide (R)-2-(tert-butylamino)-1-(7-fluoro-1-((2-(trimethylsilyl)ethoxy)methyl)-1H-indazol-4-yl)ethan-1-ol as a yellow oil (2 g, 81%). LCMS: m/z 382.3 (M+1)$^+$.

Step 6: Synthesis of (R)-2-(tert-butylamino)-1-(7-fluoro-1H-indazol-4-yl)ethan-1-ol. To a stirred solution of (R)-2-(tert-butylamino)-1-(7-fluoro-1-((2-(trimethylsilyl)ethoxy)methyl)-1H-indazol-4-yl)ethan-1-ol (2 g, 5.24 mmol) in $CH_2Cl_2$ (8 mL) at 0° C. was added $CF_3COOH$ (10 mL). The reaction mixture was stirred at room temperature for 2 hrs and then concentrated in vacuo. The residue was purified by column chromatography eluting with 10% MeOH in $CH_2Cl_2$ (containing 1% $NH_4OH$) to provide (R)-2-(tert-butylamino)-1-(7-fluoro-1H-indazol-4-yl)ethan-1-ol (0.7 g, 90% pure by HPLC). This compound was further purified by reversed-phase HPLC (0.1% TFA in $CH_3CN/H_2O$) and lyophilized with 1 N aqueous HCl (1 mL) to provide (R)-2-(tert-butylamino)-1-(7-fluoro-1H-indazol-4-yl)ethan-1-ol HCl salt as a white solid (0.37 g, 25%). $^1H$ NMR (400 MHz, $CD_3OD$) δ 8.39-9.33 (m, 1H), 7.22-7.17 (m, 1H), 7.12 (dd, J=10.3, 8.0 Hz, 1H), 5.31-5.25 (m, 1H), 3.22 (d, J=9.1 Hz, 2H), 1.39 (s, 9H); HPLC: 99.2% @254 nM; LCMS: m/z 252.3 $(M+1)^+$; SFC: 99% ee [AD-H column, mobile phase: HEP:IPA (0.1% DEA)=95:5].

Scheme 8. Synthesis of compounds 04-144 and compound 04-145.

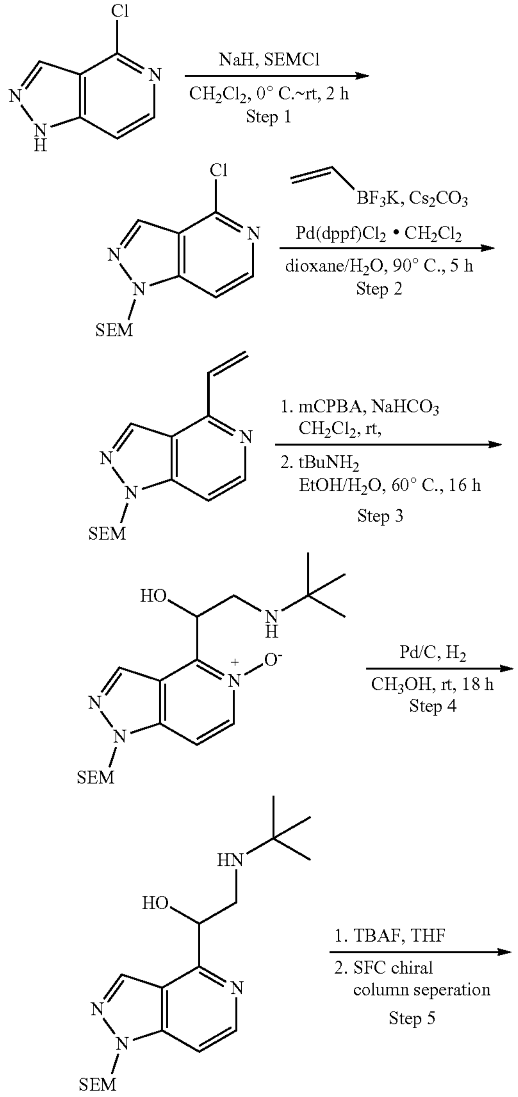

-continued

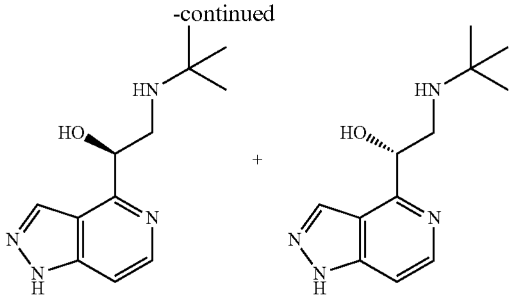

Scheme 8 illustrates the synthesis of compound 04-144 and compound 04-145.

Step 1: Synthesis of 4-chloro-1-((2-(trimethylsilyl)ethoxy)methyl)-1H-pyrazolo[4,3-c]pyridine. To a stirred solution of 4-chloro-1H-pyrazolo[4,3-c]pyridine (4 g, 27.35 mmol) in DMF (25 mL) at 0° C. was added NaH (60%, 1.64 g, 41 mmol). The resulting mixture was stirred for 0.5 h, then SEMCl (5.93 g, 35.55 mmol) was added. The mixture was stirred at room temperature for 2 hrs. The reaction was quenched with saturated ammonium chloride solution (20 mL). The mixture was extracted with ethyl acetate (20 mL×3). The combined organic layers were washed with $H_2O$ (100 mL×3), brine, dried over sodium sulfate, filtered, and concentrated under reduced pressure. The residue was purified via column chromatography eluting with 30% EtOAc in petroleum ether to provide 4-chloro-1-((2-(trimethylsilyl)ethoxy)methyl)-1H-pyrazolo[4,3-c]pyridine as a yellow oil (3 g, 39%). LC-MS: m/z 284.2 $M+1)^+$.

Step 2—Synthesis of 1-((2-(trimethylsilyl)ethoxy)methyl)-4-vinyl-1H-pyrazolo[4,3-c]pyridine. To a stirred solution of 4-chloro-1-((2-(trimethylsilyl)ethoxy)methyl)-1H-pyrazolo[4,3-c]pyridine (3 g, 10.57 mmol) in dioxane/$H_2O$ (20 mL/2 ml) was added potassium vinyltrifluoroborate (2.83 g, 21.14 mmol), Pd(dppf)$Cl_2$ $CH_2Cl_2$ (856 mg, 1.05 mmol), and $Cs_2CO_3$ (10.33 g, 31.71 mmol) under $N_2$. The mixture was stirred at 100° C. for 16 hrs. The reaction mixture was filtered through a pad of celite and washed with EtOAc (100 mL). The filtrate was washed with $H_2O$ (20 mL×2), brine (30 mL), dried over $Na_2SO_4$, filtered, and concentrated under reduced pressure. The residue was purified via column chromatography eluting with 10% EtOAc in petroleum ether to provide 1-((2-(trimethylsilyl)ethoxy)methyl)-4-vinyl-1H-pyrazolo[4,3-c]pyridine as an oil (2.5 g, 81%). LC-MS: m/z 293.3 $M+1)^+$.

Step 3: Synthesis of 4-(2-(tert-butylamino)-1-hydroxyethyl)-1-((2-(trimethylsilyl)ethoxy)methyl)-1H-pyrazolo[4,3-c]pyridine 5-oxide. To a stirred solution of 1-((2-(trimethylsilyl)ethoxy)methyl)-4-vinyl-1H-pyrazolo[4,3-c]pyridine (2.0 g, 7.26 mmol) in $CH_2Cl_2$ (10 mL) at room temperature was added saturated $NaHCO_3$ solution (10 mL) and mCPBA (3.76 g, 21.78 mmol) portion-wise. The resulting mixture was stirred for 10 min before addition of t-$BuNH_2$ (2.5 g, 34.31 mmol) and EtOH (5 mL). The resulting mixture was stirred at 60° C. for 16 hrs. The mixture was concentrated in vacuo. The residue was purified via column chromatography eluting with 10% $CH_3OH$ in $CH_2Cl_2$ to provide 4-(2-(tert-butylamino)-1-hydroxyethyl)-1-((2-(trimethylsilyl)ethoxy)methyl)-1H-pyrazolo[4,3-c]pyridine 5-oxide (1.2 g, 76% HPLC purity), which was used in the next step without further purifications. LC-MS: m/z 381.2 $M+1)^+$.

Step 4: Synthesis of 2-(tert-butylamino)-1-(1-((2-(trimethylsilyl)ethoxy)methyl)-1H-pyrazolo[4,3-c]pyridin-4-yl)ethan-1-ol. A mixture of 4-(2-(tert-butylamino)-1-hydroxyethyl)-1-((2-(trimethylsilyl)ethoxy)methyl)-1H-pyrazolo[4, 3-c]pyridine 5-oxide (0.6 g, 1.58 mmol) and Pd/C (10% on carbon, 0.06 g) under a balloon of hydrogen in EtOH (6 mL) was stirred at room temperature for 24 hrs and then stirred at 60° C. for 48 hrs. The mixture was filtered through a pad of celite and the filtrate was concentrated in vacuo to provide 2-(tert-butylamino)-1-(1-((2-(trimethylsilyl)ethoxy)methyl)-1H-pyrazolo[4,3-c]pyridin-4-yl)ethan-1-ol (0.3 g), which was used directly in the next step without further purification. LC-MS: m/z 365.2 M+1)$^+$.

Step 5: Synthesis of (S)-2-(tert-butylamino)-1-(1H-pyrazolo[4,3-c]pyridin-4-yl)ethan-1-ol and (R)-2-(tert-butylamino)-1-(1H-pyrazolo[4,3-c]pyridin-4-yl)ethan-1-ol. TBAF (1M in THF, 4 ml, 4 mmol) was added to 2-(tert-butylamino)-1-(1-((2-(trimethylsilyl)ethoxy)methyl)-1H-pyrazolo[4,3-c]pyridin-4-yl)ethan-1-ol (0.3 g, 0.82 mmol) and the mixture was stirred at 50° C. for 48 hrs. The mixture was purified by preparative TLC (10% $CH_3OH$ in $CH_2Cl_2$) and further purified via reverse phase chromatography to provide 2-(tert-butylamino)-1-(1H-pyrazolo[4,3-c]pyridin-4-yl)ethan-1-ol as a colorless oil (0.11 g, 57%). LC-MS: m/z 235.2 M+1)$^+$. Racemic 2-(tert-butylamino)-1-(1H-pyrazolo[4,3-c]pyridin-4-yl)ethan-1-ol (0.11 g, 0.47 mmol) was separated via SFC (column: IG-H; mobile phase: HEP/EtOH (0.1% DEA)=70/30) to provide (R)-2-(tert-butylamino)-1-(1H-pyrazolo[4,3-c]pyridin-4-yl)ethan-1-ol (0.02 g, 36%) and (S)-2-(tert-butylamino)-1-(1H-pyrazolo[4,3-c]pyridin-4-yl)ethan-1-ol (0.02 g, 36%) as a white solid. (R)-2-(tert-butylamino)-1-(1H-pyrazolo[4,3-c]pyridin-4-yl)ethan-1-ol: $^1H$ NMR (400 MHz, $CD_3OD$) δ 9.03 (s, 1H), 8.45 (d, J=6.9 Hz, 1H), 8.08 (d, J=6.4 Hz, 1H), 5.95 (d, J=9.4 Hz, 1H), 3.58 (d, J=12.9 Hz, 1H), 3.39 (t, J=11.5 Hz, 1H), 1.43 (s, 9H); LC-MS: m/z 235.3 (M+1)$^+$; SFC: 98.7% ee. (S)-2-(tert-butylamino)-1-(1H-pyrazolo[4,3-c]pyridin-4-yl)ethan-1-ol: $^1H$ NMR (400 MHz, $CD_3OD$) δ 9.03 (s, 1H), 8.45 (d, J=6.9 Hz, 1H), 8.08 (d, J=6.4 Hz, 1H), 5.95 (d, J=9.4 Hz, 1H), 3.58 (d, J=12.9 Hz, 1H), 3.39 (t, J=11.5 Hz, 1H), 1.43 (s, 9H); LC-MS: m/z 235.3 (M+1)$^+$; SFC: 98.3% ee.

Example 2

Evaluation of Synthesized Adrenergic Receptor Agonists cAMP homogeneous time-resolved fluorescence (HTRF): experimental methods. Compound efficacy is determined using the cAMP Gs dynamic HTRF assay (Cisbio, catalog #62AM4PEC) largely following the manufacturer's instructions, also detailed below.

Compound preparation: Candidate beta-adrenergic compounds, dissolved to 10 mM in DMSO, are diluted in 1× stimulation buffer 1 (Cisbio Part #64SB1FDD) containing 1 mM 3-Isobutyl-1-methylxanthene (IBMX; Cayman Chemical Company, catalog #13347). Serial dilutions are made in a 96 well V-bottom polypropylene compound microplate (Corning, catalog #3363) in stimulation buffer containing 1 mM IBMX, to 2× of the final desired concentration. Standard serial dilution curves are 10-point, 5-fold dilutions starting from a highest concentration of 10 μM. Controls present on every assay plate are 0.1% DMSO (vehicle control), 1 μM isoproterenol (full beta-adrenergic agonist control) and 15 μM xamoterol (partial beta-adrenergic agonist control). 5 μL from the 2× compound plate is stamped into a white 384 round well small volume HiBase assay plate (Greiner Bio-One; catalog #784075) to provide 4 technical replicates per concentration, per compound. Assay plates are centrifuged at 500×g for 10 seconds. Compounds and IBMX are prepared at 2× final dose to compensate for addition of cells.

Cell preparation: 1× stimulation buffer, washing PBS (Dulbecco's phosphate-buffered saline, —Mg —Ca; Caisson Labs, catalog #PBL01), assay PBS (Dulbecco's phosphate-buffered saline, +Mg, +Ca; Caisson Labs, catalog #PBL02) and Versene (0.02% EDTA disodium salt solution in PBS without calcium or magnesium; Caisson Labs, catalog #EDL01) are pre-warmed to 37° C. Cells expressing beta-adrenergic receptor were washed in washing PBS to remove growth medium and then released from the surface by incubating with Versene for 5-10 minutes at 37° C. Cells are harvested using assay PBS, counted manually by hemocytometer or by an automated cell counter, pelleted by centrifugation (200×g, 5 minutes) and resuspended in 37° C. 1× stimulation buffer to a final density of 1.5×10≢cells/mL. 5 μL of the suspended cell solution (7500 cell total) are added to all wells of the 384 well assay plate, the assay plate was covered with an Axygen® plate seal (Corning PCR-SP) and incubated in a humidified 37° C. environment supplemented with 5% $CO_2$ for 30 minutes.

HTRF reagent addition, reading and data analysis: After 30 minutes of cell stimulation with test compound, the assay plates are centrifuged at 500×g for 10 seconds, and incubation was stopped with the addition of 5 μL cAMP-D2 acceptor, diluted 1:21 in detection and lysis buffer 2 (Cisbio 62CL2FDF) was added to all cells. Subsequently, 5 μL Anti-cAMP-Eu Donor, diluted 1:21 in detection and lysis buffer 2, was added to cells. Plates were sealed and reactions gently 'vortexed' at 900 rpm on a Heidolph Titramax 1000 for at least 30 minutes at room temperature. Plates are centrifuged again at 500×g for 10 seconds, and HTRF was measured using a Tecan Spark plate reader at 50 flashes per well. HTRF ratios (665 nm/620 nm×10,000) are determined and plotted in GraphPad Prism to generate a concentration-effect curve. Potency estimates ($EC_{50}$ and $pEC_{50}$) are derived from the four-parameter nonlinear regression of the concentration-effect curve and an estimate of relative efficacy is determined by comparing the magnitude of the test compound HTRF signal window (min-max dose) with the signal window of the full agonist control, isoproterenol. The potency data are shown in Table 2 and Table 3 below.

TABLE 2

The pharmacological data of the chemical compounds disclosed herein.

| Compound | β1 $EC_{50}$ (nM) | β2 $EC_{50}$ (nM) |
|---|---|---|
| 02-1 | C | B |
| 02-2 | D | D |

$EC_{50}$ (nM): A < 10 nM; B = 10-100 nM; C = 100 nM-1 μM; D > 1 μM

TABLE 3

The pharmacological data of the chemical compounds disclosed herein.

| Compound | Average $pEC_{50}$ [Receptor subtype: B1-AR; Cell type: CHO-K1 (HitHunter)] | Average $pEC_{50}$ [Receptor subtype: B2-AR; Cell type: CHO-K1 (HitHunter)] | Average $pEC_{50}$ [Receptor subtype: Endogenous; Cell type: 1321N1] |
|---|---|---|---|
| 02-1 | C | B | C |
| 02-2 | D | D | — |

TABLE 3-continued

The pharmacological data of the chemical compounds disclosed herein.

| Compound | Average $pEC_{50}$ [Receptor subtype: B1-AR; Cell type: CHO-K1 (HitHunter)] | Average $pEC_{50}$ [Receptor subtype: B2-AR; Cell type: CHO-K1 (HitHunter)] | Average $pEC_{50}$ [Receptor subtype: Endogenous; Cell type: 1321N1] |
|---|---|---|---|
| 02-3 | D | C | — |
| 02-4 | C | D | — |
| 02-6 | C | B | C |
| 02-7 | D | D | D |
| 02-8 | D | D | D |
| 02-9 | C | B | — |
| 02-10 | D | C | — |
| 02-11 | D | D | — |
| 02-12 | D | D | — |
| 02-13 | B | B | — |
| 02-14 | B | A | — |
| 04-1 | A | A | — |
| 04-2 | B | A | — |
| 04-3 | D | C | — |
| 04-4 | A | A | — |
| 04-5 | D | D | — |
| 04-6 | B | A | — |
| 04-7 | B | B | — |
| 04-8 | B | A | — |
| 04-9 | C | B | — |
| 04-10 | B | B | — |
| 04-11 | B | B | — |
| 04-12 | C | B | — |
| 04-13 | B | A | — |
| 04-14 | C | A | — |
| 04-15 | D | C | — |
| 04-16 | C | B | — |
| 04-17 | C | D | — |
| 04-18 | A | B | — |
| 04-19 | A | A | — |
| 04-24 | B | B | — |
| 04-25 | A | A | — |
| 04-26 | B | B | — |
| 04-27 | A | B | — |
| 04-28 | C | D | — |
| 04-29 | C | D | — |
| 04-30 | D | — | — |
| 04-36 | A | A | — |
| 04-38 | C | A | — |
| 04-39 | A | A | — |
| 04-40 | B | B | — |
| 04-41 | A | A | — |
| 04-42 | C | C | — |
| 04-43 | A | A | — |
| 04-44 | C | A | — |
| 04-45 | A | A | — |
| 04-46 | C | C | — |
| 04-48 | D | D | — |
| 04-49 | D | D | — |
| 04-50 | C | B | — |
| 04-51 | D | D | — |
| 04-52 | C | B | — |
| 04-54 | D | C | — |
| 04-55 | B | A | — |
| 04-56 | A | A | — |
| 04-57 | A | A | — |
| 04-67 | D | D | — |
| 04-68 | D | D | — |
| 04-69 | B | C | — |
| 04-70 | — | A | — |
| 04-71 | C | C | — |
| 04-72 | A | A | — |
| 04-73 | B | B | — |
| 04-74 | D | D | — |
| 04-75 | A | A | — |
| 04-76 | A | A | — |
| 04-77 | — | D | — |
| 04-78 | C | — | — |
| 04-79 | C | C | — |
| 04-80 | A | A | — |
| 04-81 | C | C | — |
| 04-82 | A | A | — |
| 04-83 | C | C | — |
| 04-84 | A | B | — |
| 04-85 | A | A | — |
| 04-86 | C | C | — |
| 04-87 | C | C | — |
| 04-88 | A | A | — |
| 04-89 | D | — | — |
| 04-90 | C | D | — |
| 04-91 | D | — | — |
| 04-92 | D | D | — |
| 04-93 | C | C | — |
| 04-94 | A | A | — |
| 04-96 | B | B | — |
| 04-97 | D | D | — |
| 04-98 | A | B | — |
| 04-102 | C | C | — |
| 04-103 | C | C | — |
| 04-104 | C | A | — |
| 04-105 | D | D | — |
| 04-106 | C | C | — |
| 04-107 | D | C | — |
| 04-108 | A | A | — |
| 04-109 | B | A | — |
| 04-110 | D | D | — |
| 04-111 | D | D | — |
| 04-112 | A | A | — |
| 04-113 | A | A | — |
| 04-114 | D | D | — |
| 04-115 | C | B | — |
| 04-116 | A | A | — |
| 04-117 | C | A | — |
| 04-118 | D | D | — |
| 04-119 | A | A | — |
| 04-120 | D | C | — |
| 04-121 | — | D | — |
| 04-122 | A | A | — |
| 04-123 | D | C | — |
| 04-124 | B | A | — |
| 04-125 | B | A | — |
| 04-126 | D | D | — |
| 04-127 | B | A | — |
| 04-128 | D | C | — |
| 04-129 | D | B | — |
| 04-130 | A | A | — |
| 04-131 | A | A | — |
| 04-133 | A | A | — |
| 04-134 | B | C | — |
| 04-135 | A | A | — |
| 04-136 | D | C | — |
| 04-137 | C | B | — |
| 04-138 | D | C | — |
| 04-139 | D | D | — |
| 04-140 | D | C | — |
| 04-141 | B | A | — |
| 04-142 | A | A | — |
| 04-143 | B | B | — |
| 04-144 | D | D | — |
| 04-145 | D | D | — |
| 04-146 | A | A | — |
| 04-147 | A | A | — |
| 04-148 | A | A | — |
| 04-149 | A | A | — |
| 04-150 | B | A | — |
| 04-151 | A | B | — |
| 04-152 | A | A | — |
| 04-153 | D | B | — |
| 04-154 | C | A | — |
| 04-155 | D | C | — |

TABLE 3-continued

The pharmacological data of the chemical compounds disclosed herein.

| Compound | Average $pEC_{50}$ [Receptor subtype: B1-AR; Cell type: CHO-K1 (HitHunter)] | Average $pEC_{50}$ [Receptor subtype: B2-AR; Cell type: CHO-K1 (HitHunter)] | Average $pEC_{50}$ [Receptor subtype: Endogenous; Cell type: 1321N1] |
|---|---|---|---|
| 04-156 | B | A | — |
| 04-157 | C | B | — |
| 04-158 | B | A | — |

$pEC_{50}$: A > 8; B = 8-7; C = <7-6; D < 6

Those skilled in the art will recognize, or be able to ascertain, using no more than routine experimentation, numerous equivalents to the specific composition and procedures described herein. Such equivalents are considered to be within the scope of this disclosure, and are covered by the following claims.

In addition to the various embodiments described in the specification above, the following additional embodiments are contemplated herein.

Embodiment 1. A compound according to Formula (I) or an optically pure stereoisomer, pharmaceutically acceptable salt, solvate, or prodrug thereof, wherein:

Formula (I)

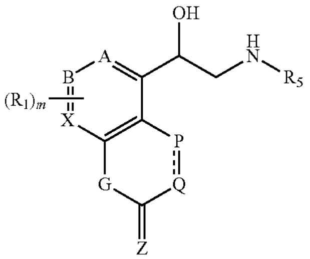

each $R_1$ is independently selected from the group consisting of hydrogen, halogen, cyano, nitro, unsubstituted or substituted amino, pentafluorosulfanyl, unsubstituted or substituted sulfonyl, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl, m is an integer selected from 0 to 3, each A, B, and X is independently a nitrogen or carbon, P is N, O, or $CR_2$, Q is N, O, or $CR_2$, G is $NR_5$ or O, and/or Z is $NR_5$, O, S, or $CR_3R_4$, $R_2$ is selected from the group consisting of hydrogen, halogen, cyano, nitro, hydroxyl, unsubstituted or substituted amino, unsubstituted or substituted alkyl, and unsubstituted or substituted alkoxy, each $R_3$ and $R_4$ is selected from the group consisting of hydrogen, halogen, cyano, nitro, hydroxyl, unsubstituted or substituted amino, unsubstituted or substituted alkyl, and unsubstituted or substituted alkoxy, $R_5$ is one or more selected from the group consisting of H, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

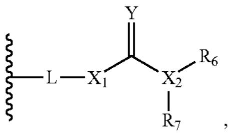
,
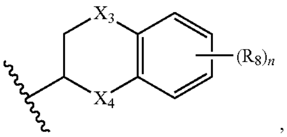
,
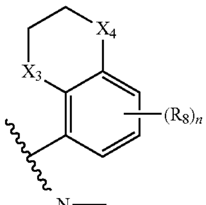
,
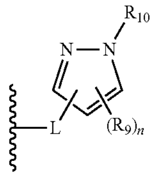
,
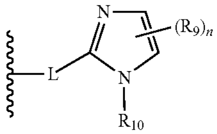
,
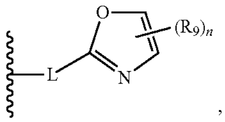
,
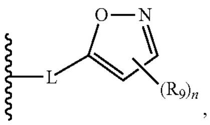
,
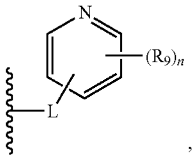
,
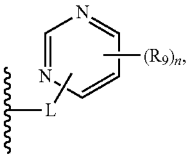
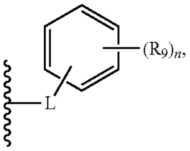
and
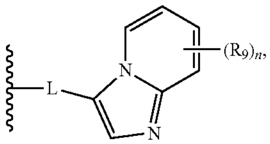

L is a C1-C5 alkyl linker optionally substituted, each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl, Y is O or S, $R_6$ and $R_7$ are independently selected from hydrogen, unsubstituted or substituted alkyl, or $R_6$ and $R_7$ are cyclically linked and together with $X_2$ to form an optionally substituted cycloalkyl or heterocycle, each $R_8$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl, n is an integer selected from 0 to 4, and $R_9$ is selected from the group consisting of hydrogen, halogen, cyano, unsubstituted or substituted alkyl, unsubstituted or substituted alkoxy, and unsubstituted or substituted amino; and $R_{10}$ is selected from the group consisting of hydrogen, cyano, unsubstituted or substituted alkyl, and unsubstituted or substituted alkoxy.

Embodiment 2. A compound according to Formula (II) or an optically pure stereoisomer, pharmaceutically acceptable salt, solvate, or prodrug thereof, wherein:

Formula (II)

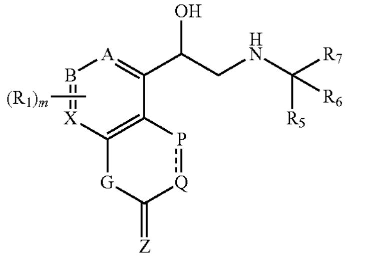

each $R_1$ is independently selected from the group consisting of hydrogen, halogen, cyano, nitro, unsubstituted or substituted amino, pentafluorosulfanyl, unsubstituted or substituted sulfonyl, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl, m is an integer selected from 0 to 3, each A, B, and X is independently a nitrogen or carbon, P is N, O, or $CR_2$, Q is N, O, or $CR_2$, G is $NR_5$ or O, and/or Z is $NR_5$, O, S, or $CR_3R_4$, $R_2$ is selected from the group consisting of hydrogen, halogen, cyano, nitro, hydroxyl, unsubstituted or substituted amino, unsubstituted or substituted alkyl, and unsubstituted or substituted alkoxy, each $R_3$ and $R_4$ is selected from the group consisting of hydrogen, halogen, cyano, nitro, hydroxyl, unsubstituted or substituted amino, unsubstituted or substituted alkyl, and unsubstituted or substituted alkoxy, $R_5$, $R_6$, and $R_7$ are independently selected from the group consisting of H, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

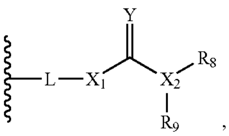
,
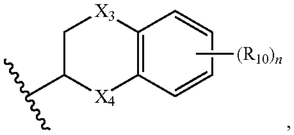
,
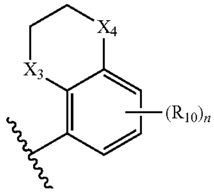
,
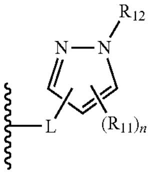
,
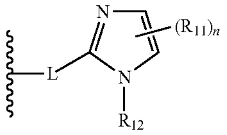
,
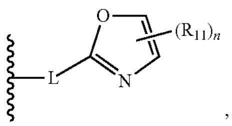
, -continued

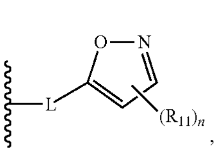
,
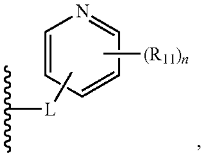
,
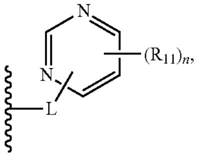
,
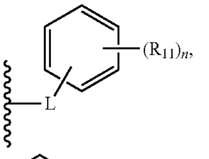
and
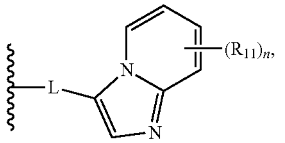

or $R_5$ and $R_6$ together with the carbon form an unsubstituted or substituted 3-7 membered cycloalkyl or heterocycle ring; L is a C1-C5 alkyl linker optionally substituted, each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl, Y is O or S, $R_8$ and $R_9$ are independently selected from hydrogen, unsubstituted or substituted alkyl, or $R_8$ and $R_9$ are cyclically linked and together with $X_2$ to form an optionally substituted cycloalkyl or heterocycle, each $R_{10}$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl, n is an integer selected from 0 to 4, $R_1$ is selected from the group consisting of hydrogen, halogen, cyano, unsubstituted or substituted alkyl, unsubstituted or substituted alkoxy, and unsubstituted or substituted amino, and $R_{12}$ is selected from the group consisting of hydrogen, cyano, unsubstituted or substituted alkyl, and unsubstituted or substituted alkoxy.

Embodiment 3. A compound with the following structure:

Compound 04-1

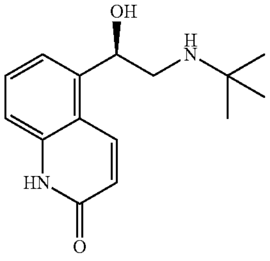

or an optically pure stereoisomer, pharmaceutically acceptable salt, solvate, or prodrug thereof.

Embodiment 4. A compound with the following structure:

Compound 04-2

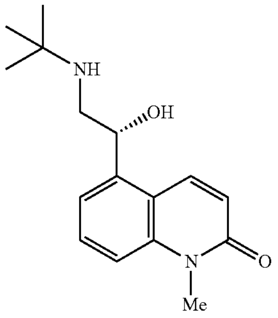

or an optically pure stereoisomer, pharmaceutically acceptable salt, solvate, or prodrug thereof.

Embodiment 5. A compound with the following structure:

Compound 04-3

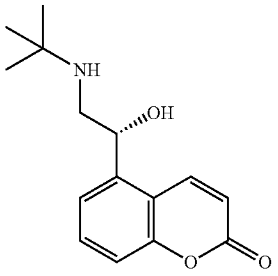

or an optically pure stereoisomer, pharmaceutically acceptable salt, solvate, or prodrug thereof.

Embodiment 6. A compound with the following structure:

Compound 04-4

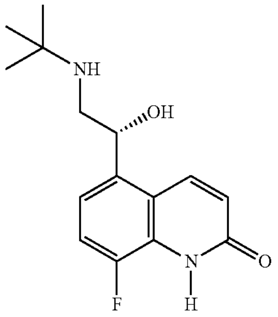

or an optically pure stereoisomer, pharmaceutically acceptable salt, solvate, or prodrug thereof.

Embodiment 7. A compound with the following structure:

Compound 04-5

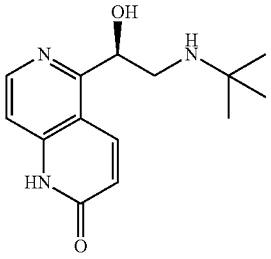

or an optically pure stereoisomer, pharmaceutically acceptable salt, solvate, or prodrug thereof.

Embodiment 8. A pharmaceutical composition including the compound of any one of embodiments 1-2 and a pharmaceutically acceptable excipient.

Embodiment 9. The compound of any one of embodiments 1-7, wherein the compound is an agonist, partial agonist or antagonist of an adrenergic receptor;

Embodiment 10. The compound of any one of embodiments 1-7, wherein the compound is a β1-adrenergic receptor agonist, β2-adrenertic receptor agonist or non-selective β1/β2-adrenergic receptor agonist.

Embodiment 11. The compound of any one of embodiments 1-7, wherein the compound is a β1-adrenergic receptor agonist.

Embodiment 12. The compound of any one of embodiments 1-7, wherein the compound is a β2-adrenergic receptor agonist.

Embodiment 13. The compound of any one of embodiments 1-7, wherein the compound is a non-selective β1/β2-adrenergic agonist.

Embodiment 14. A method of treating a subject with a disease, the method including administering to the subject a therapeutically effective amount of a compound of any one of claims 1-2.

Embodiment 15. The method according to embodiment 14, wherein the disease is a disease associated with an adrenergic receptor.

Embodiment 16. The method according to embodiment 14, wherein the disease is a neurodegenerative disease.

Embodiment 17. The method according to embodiment 14, wherein the subject is a human.

Embodiment 18. The method according to embodiment 14, wherein the disease is selected from myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis.

Embodiment 19. The method according to embodiment 14, wherein the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

Embodiment 20. The method according to embodiment 14, wherein the disease is a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS).

Embodiment 21. The method according to embodiment 14, wherein the disease is a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the subject does not have Alzheimer's disease (AD)

Embodiment 22. The method according to any one of embodiments 14-21, wherein the subject does not have Down Syndrome Embodiment 23. The method of any one of embodiments 14-22, wherein administering to the subject further includes a peripherally acting β-blocker (PABRA) along with the compound.

Embodiment 24. The method of embodiment 23, wherein a peripherally acting β-blocker (PABRA) is administered to the subject prior to administration of the compound.

Embodiment 25. The method of embodiment 23, wherein a peripherally acting β-blocker (PABRA) is administered to the subject concurrently with the administration of the compound.

Embodiment 26. The method of any one of embodiments 14-22, wherein a β1 agonist, a β2 agonist, or a non-selective β1/β2 agonist is administered to the patient in addition to the compound.

What is claimed is:

1. The compound

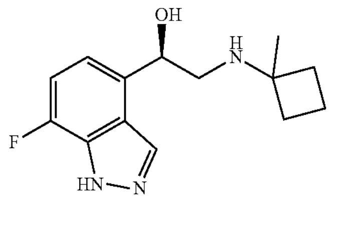 [SMILES: CC1(NC[C@H](O)c2ccc(F)c3[nH]ncc23)CCC1]

or a pharmaceutically acceptable salt thereof.

2. A compound:

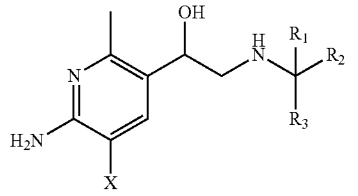

wherein X is selected from H, F, Cl, Br, and I, $R_1$ and $R_2$ are methyl;

$R_3$ is methyl, ethyl, or a hydroxy methyl, or $R_2$ and $R_3$ are optionally taken together with their intervening atoms to form a 4-membered carbocycle or a 3-membered carbocycle.

3. The compound of claim 2, wherein $R_1$, $R_2$ and $R_3$, along with the methylamine group they are attached to, combine to form a group selected from:

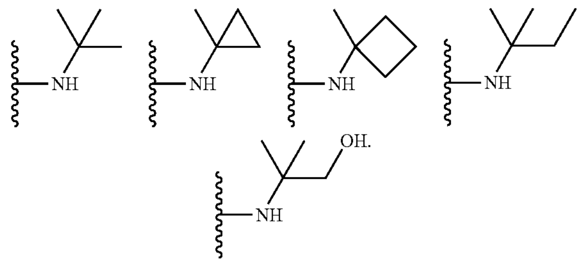

4. A pharmaceutical composition including the compound of claim 1 or 2 and a pharmaceutically acceptable excipient.

5. The compound of claim 1 or 2, wherein the compound is an agonist, partial agonist or antagonist of an adrenergic receptor.

6. The compound of claim 1 or 2, wherein the compound is a β1-adrenergic receptor agonist, β2-adrenergic receptor agonist or non-selective β1/β2-adrenergic receptor agonist.

7. The compound of claim 1 or 2, wherein the compound is a β1-adrenergic receptor agonist.

8. The compound of claim 1 or 2, wherein the compound is a β2-adrenergic receptor agonist.

9. The compound of claim 1 or 2, wherein the compound is a non-selective β1/β2-adrenergic agonist.

* * * * *